United States Patent
Zuscik et al.

(10) Patent No.: US 11,110,147 B2
(45) Date of Patent: Sep. 7, 2021

(54) COLLAGEN HYDROLYSATES AS A BENEFICIAL PREBIOTIC AND THEIR EFFECT ON JOINT INFLAMMATION AND OSTEOARTHRITIS

(71) Applicants: ROUSSELOT B.V., Son (NL); UNIVERSITY OF ROCHESTER, Rochester, NY (US)

(72) Inventors: Michael Zuscik, Rochester, NY (US); Janne Prawitt, Brussels (BE); Eric Schott, Rochester, NY (US); Robert Mooney, Fairport, NY (US); Christopher Farnsworth, Maplewood, MO (US)

(73) Assignees: ROUSSELOT B.V; UNIVERSITY OF ROCHESTER, Rochester, NY (US)

( * ) Notice: Subject to any disclaimer, the term of this patent is extended or adjusted under 35 U.S.C. 154(b) by 0 days.

(21) Appl. No.: 16/489,890

(22) PCT Filed: Mar. 1, 2018

(86) PCT No.: PCT/EP2018/055060
§ 371 (c)(1),
(2) Date: Aug. 29, 2019

(87) PCT Pub. No.: WO2018/166807
PCT Pub. Date: Sep. 20, 2018

(65) Prior Publication Data
US 2020/0069762 A1    Mar. 5, 2020

Related U.S. Application Data

(60) Provisional application No. 62/554,555, filed on Sep. 5, 2017, provisional application No. 62/471,582, filed on Mar. 15, 2017.

(51) Int. Cl.
| | | |
|---|---|---|
| *A61K 38/01* | (2006.01) |
| *A23K 20/147* | (2016.01) |
| *A23L 33/18* | (2016.01) |
| *A61P 19/02* | (2006.01) |
| *A61P 1/00* | (2006.01) |

(52) U.S. Cl.
CPC .......... *A61K 38/014* (2013.01); *A23K 20/147* (2016.05); *A23L 33/18* (2016.08); *A61P 1/00* (2018.01); *A61P 19/02* (2018.01); *A23V 2002/00* (2013.01)

(58) Field of Classification Search
CPC ... A23K 20/147; A23L 33/18; A23V 2002/00; A61K 31/737; A61K 38/01; A61K 38/014; A61K 38/39; A61P 19/02; A61P 1/00
See application file for complete search history.

(56) References Cited

U.S. PATENT DOCUMENTS

2015/0232534 A1* 8/2015 Oesser ............... A61P 3/02
514/16.9
2016/0263176 A1* 9/2016 Serisier ............... A61K 31/198

FOREIGN PATENT DOCUMENTS

| CN | 101455396 A | 6/2009 |
| CN | 101720928 A | 6/2010 |
| EP | 0254289 A2 | 1/1988 |
| WO | WO 96/05851 A1 | 2/1996 |
| WO | WO 98/44929 A1 | 10/1998 |
| WO | WO 2015/177309 A1 | 11/2015 |

OTHER PUBLICATIONS

Iwai et al. Identification of Food-Derived Collagen Peptides in Human Blood after Oral Ingestion of Gelatin Hydrolysates. J Agricultural and Food Chemistry, 2005, 53, pp. 6531-6536. (Year: 2005).*
Dar et al. Daily oral consumption of hydrolyzed type 1 collagen is chondroprotective and antiinflammatory in murine posttraumatic osteoarthritis. PLoS ONE vol. 12, No. 4, pp. 1/24-24/24. (Year: 2017).*
Schadow et al. Metabolic Response of Human Osteoarthritic Cartilage to Biochemically Characterized Collagen Hydrolysates. International Journal of Molecular Sciences, vol. 18, No. 207, pp. 1/20-20/20. (Year: 2017).*
Oesser et al. Stimulation of type II collagen biosynthesis and secretion in bovine chondrocytes cultured with degraded collagen. Cell Tissue Res, vol. 311, pp. 393-399. (Year: 2003).*
Oesser et al. Oral Administration of 14C Labeled Gelatin Hydrolysate Leads to an Accumulation of Radioactivity in Cartilage of Mice (C57/BL). Int J Nutrition, vol. 129, No. 10, pp. 1891-1895. (Year: 1999).*
International Search Report and Written Opinion in related PCT Application No. PCT/EP2018/055060, dated May 15, 2018 (12 pages).
International Preliminary Report on Patentability in related PCT Application No. PCT/EP2018/055060, dated May 21, 2019 (12 pages).

* cited by examiner

*Primary Examiner* — Marcela M Cordero Garcia
(74) *Attorney, Agent, or Firm* — Lathrop GPM LLP; James H. Velema, Esq.; Judith L. Stone-Hulslander, Esq.

(57) ABSTRACT

The invention generally relates to pharmaceuticals and/or nutraceuticals. More particularly, the invention provides compositions of collagen-based peptides and specific digestive tract microbes useful for supporting or promoting joint, skin and/or bone health, and methods of preparation and use thereof. The invention further provides for the use of compositions of collagen-based peptides as a prebiotic for modulating the gut microbiome.

17 Claims, 29 Drawing Sheets
Specification includes a Sequence Listing.

FIG. 1A
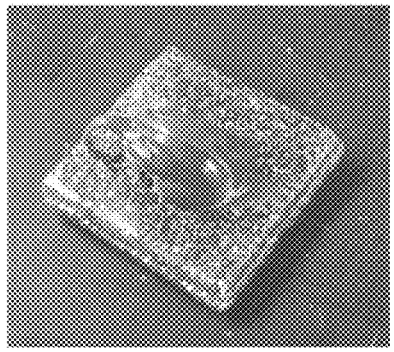
FIG. 1B
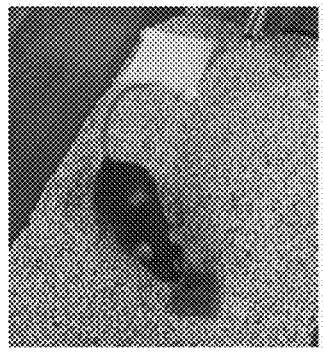
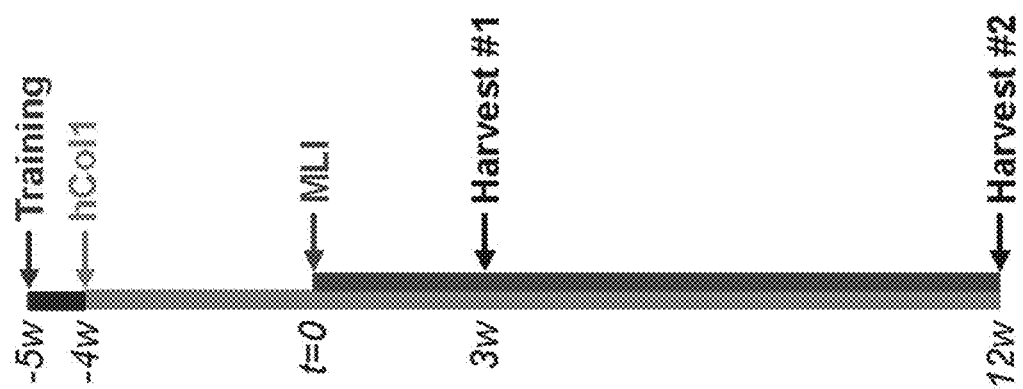
FIG. 1C
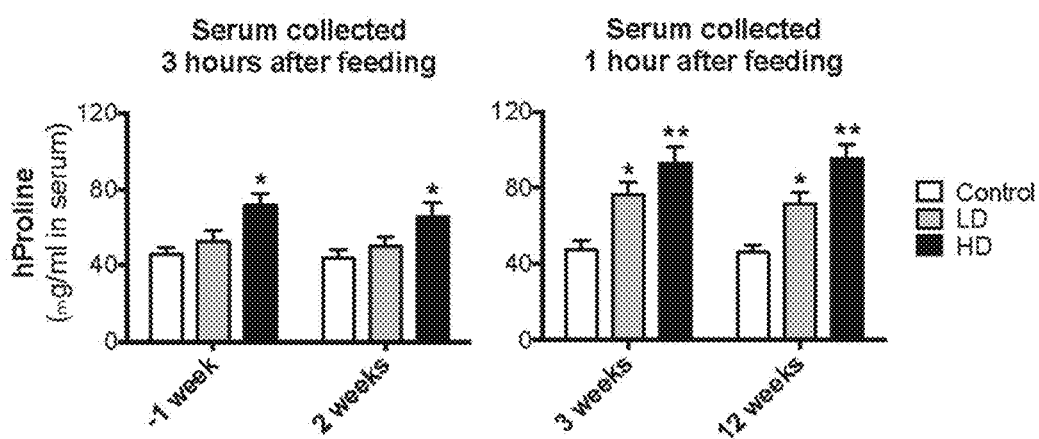
FIG. 1D
FIG. 1E

FIG. 2A
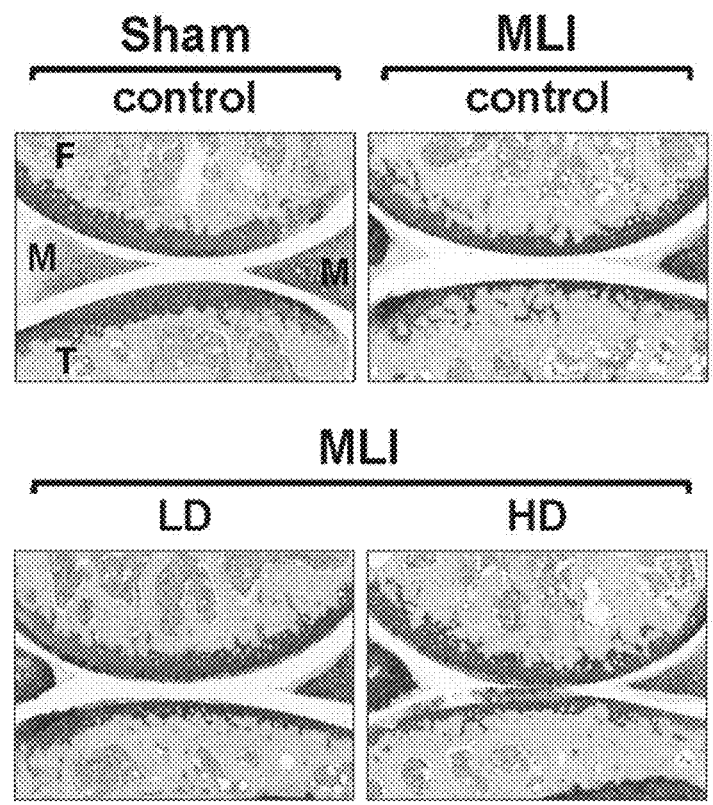
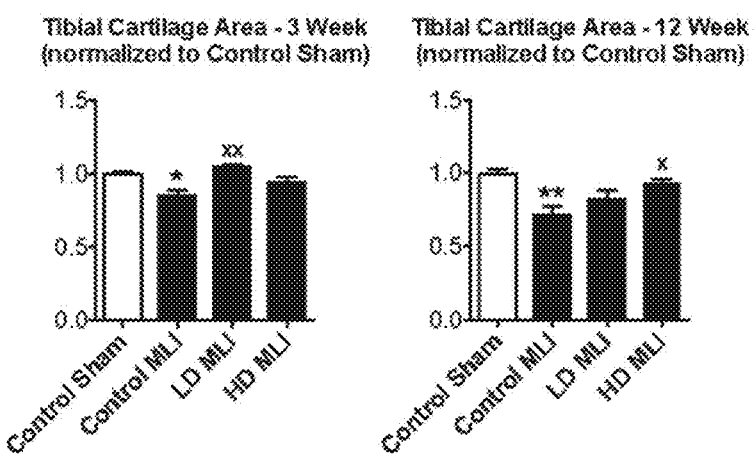
FIG. 2B
FIG. 2C

FIG. 5A
MMP13
FIG. 5B
Col X
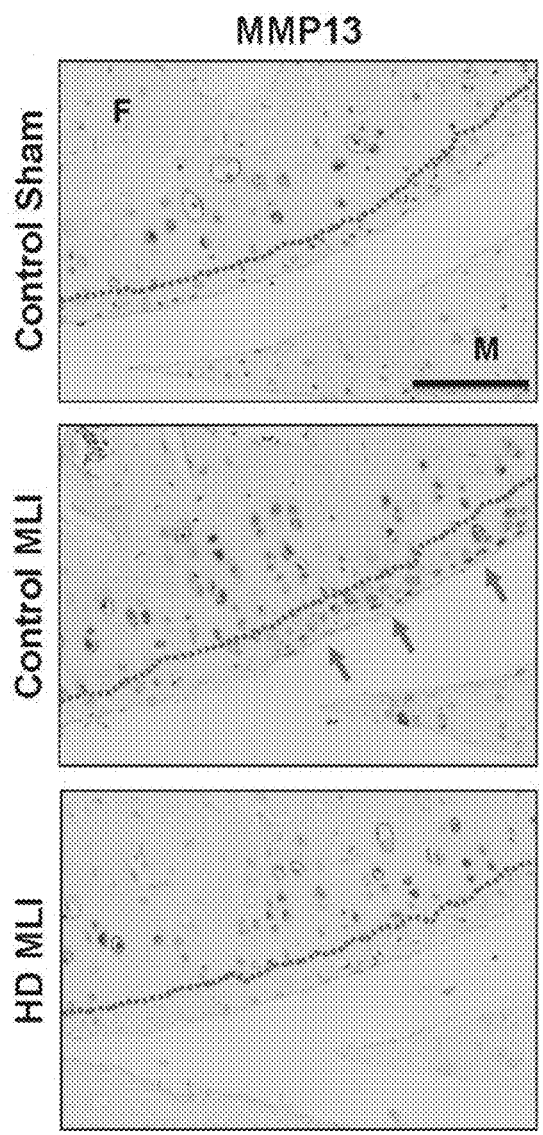
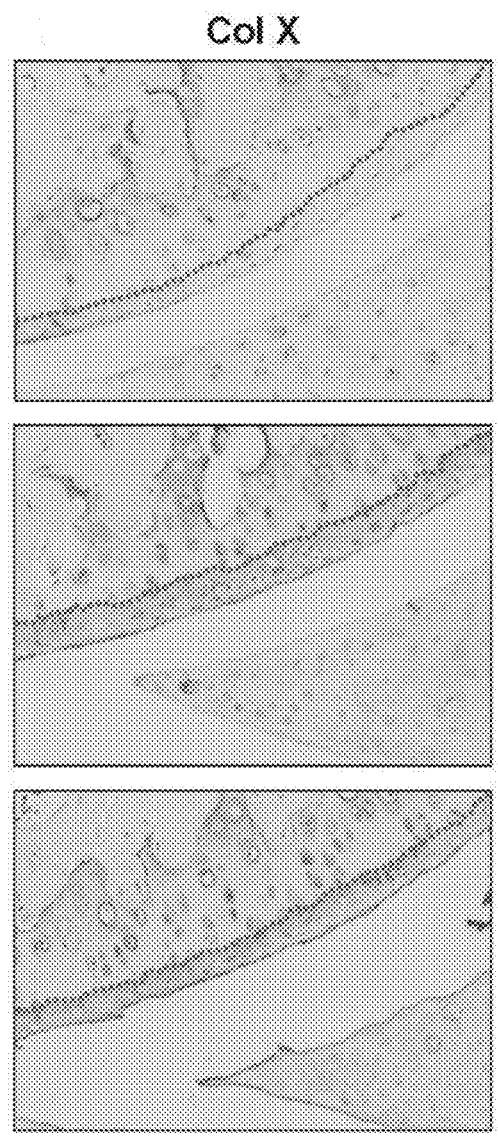

FIG. 8A
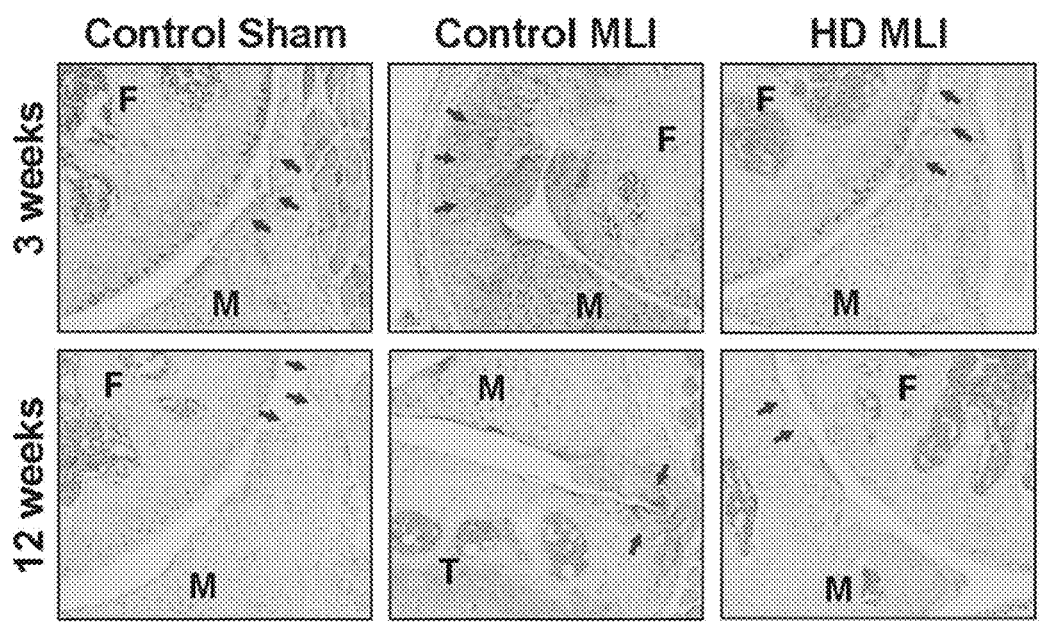
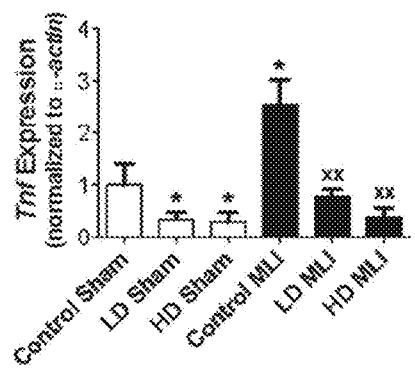
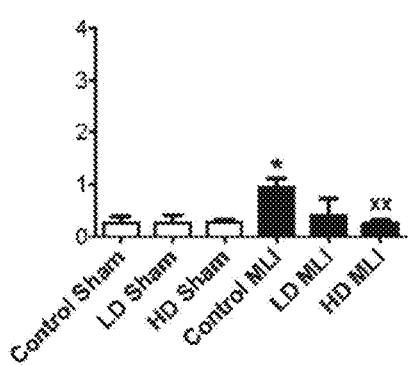
FIG. 8B　　　　　　　　FIG. 8C

FIG. 14A
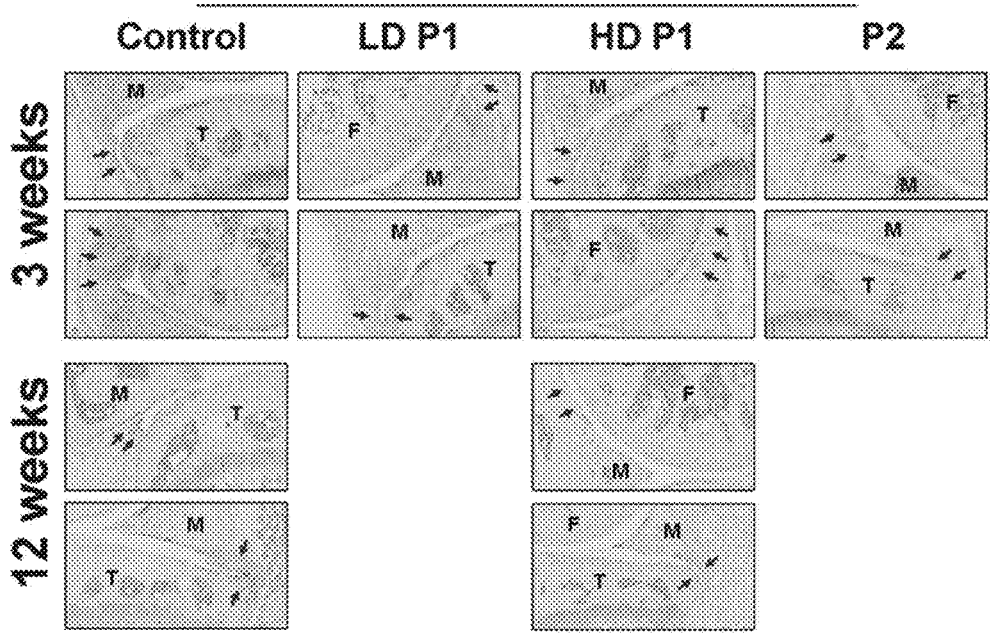
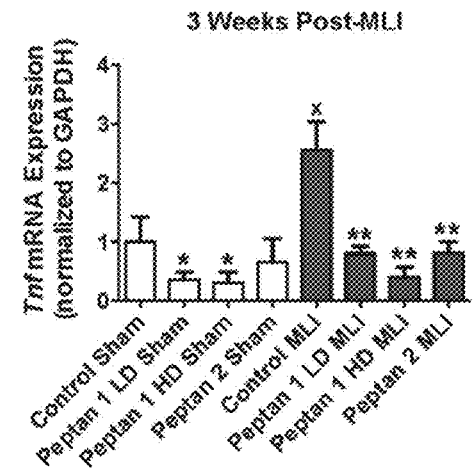
FIG. 14B
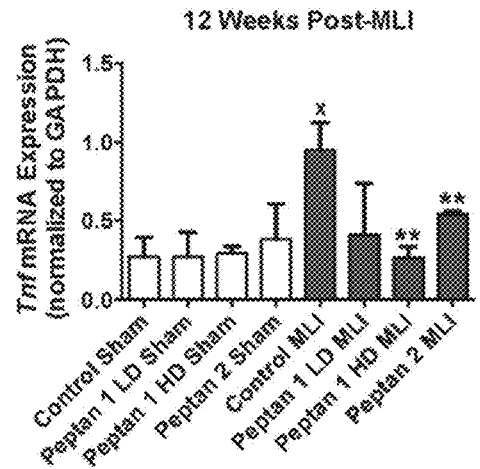
FIG. 14C

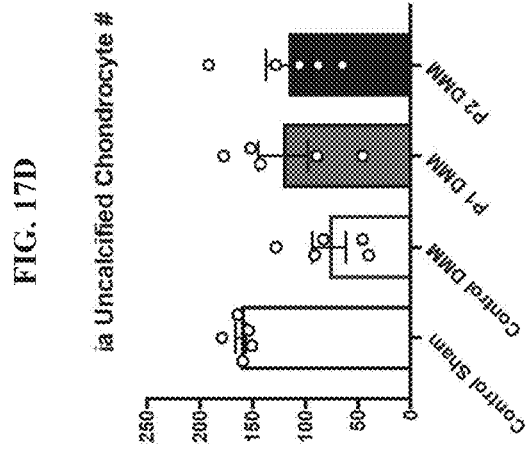
FIG. 17D
FIG. 17C
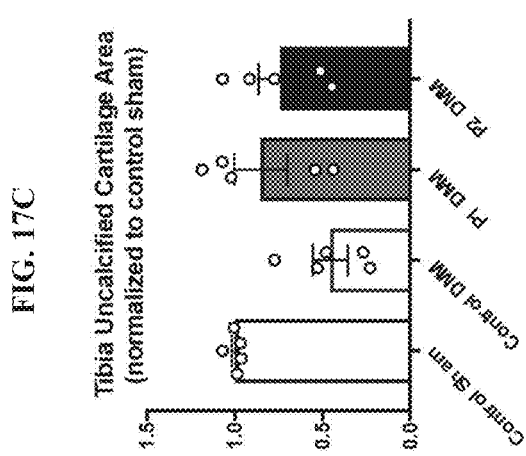
FIG. 17B
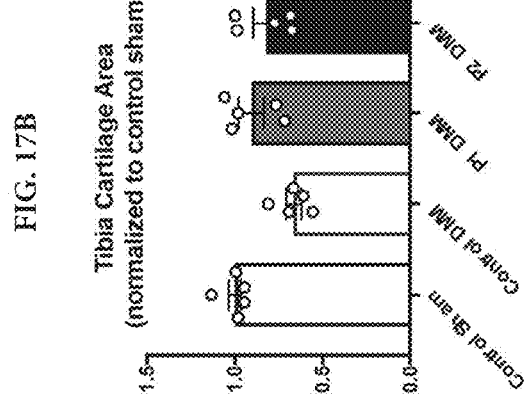

SEQUENCE LISTING

```
<160> NUMBER OF SEQ ID NOS: 12

<210> SEQ ID NO 1
<211> LENGTH: 24
<212> TYPE: DNA
<213> ORGANISM: Artificial Sequence
<220> FEATURE:
<223> OTHER INFORMATION: Tnf forward primer

<400> SEQUENCE: 1
ctcttctgtc tactgaactt cggg                                      24

<210> SEQ ID NO 2
<211> LENGTH: 24
<212> TYPE: DNA
<213> ORGANISM: Artificial Sequence
<220> FEATURE:
<223> OTHER INFORMATION: Tnf reverse primer

<400> SEQUENCE: 2
gagaagatga tctgagtgtg aggg                                      24

<210> SEQ ID NO 3
<211> LENGTH: 20
<212> TYPE: DNA
<213> ORGANISM: Artificial Sequence
<220> FEATURE:
<223> OTHER INFORMATION: Il1-beta forward primer

<400> SEQUENCE: 3
cacagcagca catcaacaag                                           20

<210> SEQ ID NO 4
<211> LENGTH: 20
<212> TYPE: DNA
<213> ORGANISM: Artificial Sequence
<220> FEATURE:
<223> OTHER INFORMATION: Il1-beta reverse primer

<400> SEQUENCE: 4
gtgctcatgt cctcatcctg                                           20
```

```
<210> SEQ ID NO 5
<211> LENGTH: 20
<212> TYPE: DNA
<213> ORGANISM: Artificial Sequence
<220> FEATURE:
<223> OTHER INFORMATION: Mmp13 forward primer

<400> SEQUENCE: 5
aagatgtgga gtgcctgatg                                              20

<210> SEQ ID NO 6
<211> LENGTH: 20
<212> TYPE: DNA
<213> ORGANISM: Artificial Sequence
<220> FEATURE:
<223> OTHER INFORMATION: Mmp13 reverse primer

<400> SEQUENCE: 6
aaggccttct ccacttcaga                                              20

<210> SEQ ID NO 7
<211> LENGTH: 22
<212> TYPE: DNA
<213> ORGANISM: Artificial Sequence
<220> FEATURE:
<223> OTHER INFORMATION: Prg4 forward primer

<400> SEQUENCE: 7
agtgctgtcc tgatttcaag ag                                           22

<210> SEQ ID NO 8
<211> LENGTH: 24
<212> TYPE: DNA
<213> ORGANISM: Artificial Sequence
<220> FEATURE:
<223> OTHER INFORMATION: Prg4 reverse primer

<400> SEQUENCE: 8
ggtgatttgg gtgagcgttt ggta                                         24

<210> SEQ ID NO 9
<211> LENGTH: 20
<212> TYPE: DNA
<213> ORGANISM: Artificial Sequence
<220> FEATURE:
<223> OTHER INFORMATION: beta-actin forward primer

<400> SEQUENCE: 9
tgttaccaac tgggacgaca                                              20

<210> SEQ ID NO 10
<211> LENGTH: 20
<212> TYPE: DNA
<213> ORGANISM: Artificial Sequence
<220> FEATURE:
<223> OTHER INFORMATION: beta-actin reverse primer

<400> SEQUENCE: 10
ctgggtcatc ttttcacggt                                              20

<210> SEQ ID NO 11
<211> LENGTH: 20
<212> TYPE: DNA
<213> ORGANISM: Artificial Sequence
<220> FEATURE:
<223> OTHER INFORMATION: 319F primer
```

```
<400> SEQUENCE: 11
actcctacgg gaggcagcag                                              20

<210> SEQ ID NO 12
<211> LENGTH: 20
<212> TYPE: DNA
<213> ORGANISM: Artificial Sequence
<220> FEATURE:
<223> OTHER INFORMATION: 806R primer

<400> SEQUENCE: 12
tgaggatgcc ctccgtcgtc                                              20
```

COLLAGEN HYDROLYSATES AS A BENEFICIAL PREBIOTIC AND THEIR EFFECT ON JOINT INFLAMMATION AND OSTEOARTHRITIS

RELATED APPLICATIONS

This application is a 35 U.S.C. § 371 filing of International Patent Application No. PCT/EP2018/055060, filed Mar. 1, 2018, which claims the benefit of U.S. Provisional Patent Application No. 62/471,582, filed Mar. 15, 2017; and 62/554,555, filed Sep. 5, 2017, the entire disclosures of which are hereby incorporated herein by reference.

TECHNICAL FIELD OF THE INVENTION

The invention generally relates to pharmaceuticals and/or nutraceuticals. More particularly, the invention provides compositions of collagen-based peptides and specific digestive tract microbes useful for supporting or promoting joint, skin and/or bone health, and methods of preparation and use thereof. The invention further provides for the use of compositions of collagen-based peptides as a prebiotic for modulating the gut microbiome.

BACKGROUND OF THE INVENTION

Osteoarthritis (OA) is one of the most prevalent diseases in the world, with recent estimates projecting that >250 million people are afflicted globally. In the U.S., OA afflicts 35 million people, with diarthrodial and spinal OA being the most prevalent disease, surpassing the next top four causes of disability combined (heart, pulmonary, mental health and diabetic conditions). In a recent analysis, global medical costs for lower extremity OA exceed $350 billion/year, with the reduced quality of life and physical function of OA patients exerting an additional hidden economic impact that surpasses $50 billion/year. (Murray et al. 2010 *Lancet.* 2013; 381(9871):997-102; Lawrence et al. 2008 *Arthritis Rheum.* 58(1):26-35; CDC, Prevalence and most common causes of disability among adults—United States 2005, MMWR MorbMortalWklyRep. 2009; 58(16):421-6; Salmon et al. 2016 *Osteoarthritis Cartilage* 24(9):1500-8.)

OA is a joint disease of multifactorial etiology characterized by degeneration and loss of articular cartilage and meniscus, subchondral bone sclerosis, osteophyte formation, and synovial hyperplasia. Etiologic complexity and 'whole organ' involvement of multiple tissues within the OA joint during the degenerative process represent significant challenges in the development of disease modifying therapeutic strategies. (Buckwalter et al. 2005 *InstrCourse Lect.* 54:465-80; Goldring et al. 2007 *J Cell Physiol.* 213(3):626-34; Loeser et al. 2012 *Arthritis Rheum.* 64(6):1697-707.)

There are no disease-modifying therapies available for OA. Over the past two decades, more than a dozen human clinical trials have been performed to test candidate disease modifying OA drugs (DMOADs), none of which have emerged to be accepted as a bona fide therapeutic agent. (Kraus et al. 2011 *Osteoarthritis Cartilage* 19(5):515-42; Malfait et al. 2015 *Arthritis research & therapy.* 17:225.)

The only treatment options for these patients before total joint arthroplasty (TKA) at end stage disease are pain reduction through palliative care and physical therapy. Palliative management of OA primarily involves nonsteroidal anti-inflammatory drugs, intraarticular injection of corticosteroids or hyaluronic acid, narcotic-based analgesia including opioids, and joint arthroplasty.

Skin dryness and an accelerated fragmentation of the collagen network in the dermis are hallmarks of skin aging. Nutrition is a key factor influencing skin health and consequently its appearance. A wide range of dietary supplements is offered to improve skin health, but none have been established universally as accepted agents that mitigate the effects of aging and rejuvenate skin structure. The nutricosmetic industry seeks to address the unmet need for agents that can preserve and protect skin health, in aging particularly. (Shuster et al. 1975 *The British journal of dermatology* 93(6):639-43; Schagen et al. 2012 *Dermatoendocrinol* 4(3): 298-307; Varani et al. 2006 *The American journal of pathology* 168(6):1861-8; Draelos et al. 2010 *Clin Dermatol.* 28(4):400-8.) Poor bone health, loss of bone mass, and osteoporosis collectively represent a significant clinical challenge and public health burden. In the US alone, associated costs amount to $22 billion. Osteoporosis is found in 70% of the elderly population and especially pronounced in post-menopausal women and in advanced aging in both sexes. It leads to increased risk of fracture and delayed repair. Current treatments have serious side effects. Thus, new and safer therapeutic approaches are an important unmet need. (Briggs et al. 2016 *Gerontologist* 56 Suppl 2:S243-55; Pisani et al. 2016 *World J Orthop.* 7(3):171-81; O'Connor et al. 2016 *The Medical clinics of North America* 100(4): 807-26.)

Thus, the development of therapeutic, nutraceutical and/or preventative strategies that offer protective and/or regenerative capability is a critical unmet need and central pursuit in addressing joint, skin and bone health.

SUMMARY OF THE INVENTION

The invention is based in part on the unexpected discovery that hydrolyzed collagen peptides have effects on the gut microbiome, which are associated with positive effects in OA, joint health, skin health and bone health. This discovery enables the development of health supporting or promoting and disease-mitigating approaches that combine hCol1 and/or hCol2 as prebiotics, optionally with a probiotic mixture of microbes, including those from the phylum Tenericutes and/or the order Anaeroplasmatales and/or the genus *Bifidobacteria* that are orally consumed as dietary supplements. These can be formulated, for example, as a powder or liquid mixture that may be added to food or compressed into a tablet or capsule for direct oral consumption on a daily, thrice weekly, twice weekly, or weekly basis.

The present invention thus may fundamentally alter the treatment protocol for OA, joint health, skin health and bone health and provide a novel approach to improving gut microbiome. The present invention enables a novel approach that utilizes hydrolyzed type 1 and/or type 2 collagen peptides (hCol1/2) as dietary supplements that have a biological effect rooted in distinct and specific changes in the populations of resident intestinal microbes. These changes in gut microbiome in turn influence numerous tissues, with potent joint health potential and therapeutic efficacy in OA, as well as other health-promoting benefits in the integument and skeletal systems. The invention provides a particular capability of preemptive protection and therapeutic efficacy in osteoarthritis (OA), to support or promote skin health, joint health or bone health.

A composition comprising hydrolyzed collagen peptides was shown in the experimental section to act as a prebiotic by improving the gut microbiome in a subject, in particular by increasing the microbial diversity in the gut of said subject. It is generally agreed upon in the literature that a more diverse gut microbiota is beneficial. It is also shown that oral administration of hydrolyzed collagen peptides reduces pro-inflammatory species in the gut, and increases anti-inflammatory species. It has further been shown that said composition comprising hydrolyzed collagen peptides reduces markers for systemic inflammation, in particular circulating TNF-alpha, an effect that is often observed following the administration of prebiotics (Delzenne et al. 2011 *Nat Rev Endocrinol* 7:639-646; O'Connor et al. 2017 *Maturitas* 104:11-18). In addition, beneficial health effects, including joint protective effects and anti-inflammatory effects in joint tissue, were shown for the compositions comprising hydrolyzed collagen peptide, further supporting its use as a prebiotic. Accordingly, in an aspect, the invention provides for the use of a composition comprising hydrolyzed collagen peptides as a prebiotic. Also disclosed herein is the use of hydrolyzed collagen peptides as a prebiotic. In particular embodiments, the composition or the hydrolyzed collagen peptides are used for modulating the gut microbiome in a subject, more particularly for increasing the diversity of the gut microbiome. A related aspect relates to a method for modulating the gut microbiome in a subject, more particularly for increasing the diversity of the gut microbiome, comprising administering to the subject an effective amount of a composition comprising hydrolyzed collagen peptides.

In embodiments, the composition comprises at least 90%, preferably at least 95%, by weight hydrolyzed collagen peptides, based on the dry mass of the composition. In embodiments, the hydrolyzed collagen peptides are type 1 hydrolyzed collagen peptides (hCol1) and/or type 2 hydrolyzed collagen peptides (hCol2). In further embodiments, the hCol1 has a mean molecular weight between about 300 Da and about 7500 Da and/or the hCol2 has a mean molecular weight between about 300 Da and about 7500 Da. In further embodiments, the hCol1 originates from porcine, bovine or fish and/or the hCol12 originates from porcine, bovine or fish. In embodiments, the composition is formulated in a food or feed product, or a food or feed ingredient for oral administration, or as a dietary supplement for oral administration. In embodiments, the composition is administered to a subject each day for at least 7 days, preferably for at least 14 days. In embodiments, the composition is administered to a subject at a daily dosage of between 0.5 g and 15 g. In another aspect, a composition comprising hydrolyzed collagen peptides is provided for use in the prevention or treatment of joint inflammation, in particular a synovial inflammation, in a subject. A related aspect relates to a method for preventing or treating joint inflammation, in particular a synovial inflammation, in a subject, said method comprising administering to the subject an effective amount of a composition comprising hydrolyzed collagen peptides. In embodiments of the composition for use or the method, the composition comprises at least 90%, preferably at least 95%, by weight hydrolyzed collagen peptides, based on the dry mass of the composition. In embodiments, the hydrolyzed collagen peptides are type 1 hydrolyzed collagen peptides (hCol1) and/or type 2 hydrolyzed collagen peptides (hCol2). In further embodiments, the hCol1 has a mean molecular weight between about 300 Da and about 7500 Da and/or the hCol2 has a mean molecular weight between about 300 Da and about 7500 Da. In further embodiments, the hCol1 originates from porcine, bovine or fish and/or the hCol12 originates from porcine, bovine or fish.

A further aspect is directed to a composition comprising hydrolyzed collagen peptides for use in the prevention or treatment of osteoarthritis, in particular posttraumatic osteoarthritis or obesity-induced osteoarthritis, in a subject, wherein the hydrolyzed collagen peptides are type 2 hydrolyzed collagen peptides (hCol2) that originate from porcine, bovine or fish collagen from cartilage. A related aspect is directed to a method for preventing or treating osteoarthritis, in particular posttraumatic osteoarthritis or obesity-induced osteoarthritis, in a subject, said method comprising administering to the subject an effective amount of a composition comprising hydrolyzed collagen peptides, wherein the hydrolyzed collagen peptides are type 2 hydrolyzed collagen peptides (hCol2) that originate from porcine, bovine or fish collagen from cartilage. In embodiments of the composition for use or the method, the composition comprises at least 90%, preferably at least 95%, by weight hydrolyzed collagen peptides, based on the dry mass of the composition. In embodiments, the hCol2 has a mean molecular weight between about 300 Da and about 7500 Da.

Yet another aspect relates to the use of a composition comprising hydrolyzed collagen peptides as a chondroprotective agent, wherein the hydrolyzed collagen peptides are type 2 hydrolyzed collagen peptides (hCol2). A related aspect is directed to a method for providing a chondroprotective effect in a subject, said method comprising administering to the subject an effective amount of a composition comprising hydrolyzed collagen peptides, wherein the hydrolyzed collagen peptides are type 2 hydrolyzed collagen peptides (hCol2). In embodiments, of the use or the method, the composition comprises at least 90%, preferably at least 95%, by weight hCol2, based on the dry mass of the composition. In embodiments, the hCol2 has a mean molecular weight between about 300 Da and about 7500 Da. In embodiments, the hCol12 originates from porcine, bovine or fish collagen from cartilage.

BRIEF DESCRIPTION OF THE DRAWINGS

FIGS. 1A-1E: Effective bolus delivery of hCol1 and experimental timeline. Nutella was used as a vehicle to deliver daily bolus doses of hCol1 to mice such that a delivery of a 150 mg mixture provided a daily bolus dose of either 3.8 mg (LD) or 38 mg (HD) hCol1 (Control=Nutella alone). Experimental mixtures were placed on autoclavable ceramic tiles (FIG. 1A) and presented to individually house mice (FIG. 1B) at the same time daily. After 5-7 days of training with vehicle alone, mice consumed the full amount presented within 2 minutes. Panel (FIG. 1C) depicts the experimental timeline. Mice were presented Nutella daily in the bolus feeding regimen for a 1 week training period, and then Control, LD and HD daily supplements were initiated and continued for the remainder of the experiment. After 4 weeks of supplementation, MLI (right knee) and Sham (left knee) surgery was performed (t=0), followed by tissue harvests at 3 weeks and 12 weeks post-surgery. (FIG. 1D and FIG. 1E) To confirm successful delivery of hCol1, serum hProline levels were quantified via ELISA. Serum samples collected 1 week before (−1) and 2 weeks after surgery were harvested 3 hours after the mice consumed supplements (FIG. 1D). Serum samples collected 3 and 12 weeks after surgery were harvested 1 hour after consumption of the supplements (FIG. 1E). Significant differences between groups were identified via one-way ANOVA with a Tukey's multiple comparisons post-test (*$p<0.05$, **$p<0.01$ compared to Control, N=6). It should be noted, a subset of experiments included delivery of hCol2 as well, at a daily dose of 3.8 mg/day (equivalent to the low dose hCol1) (data not shown).

FIGS. 2A-2C: Cartilage loss following MLI in hCol1-fed mice is reduced. Panel (FIG. 2A) presents an array of representative 40× Toluidine Blue/Fast Green stained sagittal sections from the medial compartment of sham and MLI joints 12 weeks post-injury under various treatment conditions (control=vehicle, LD=3.8 mg hCol1/day, HD=38 mg hCol1/day). Joint structures are labeled (F=femur, M=meniscus, T=tibia) and the black scale bar depicts 100 μm. Total tibial cartilage area was determined in these representative sections as well as a series of similarly stained serial sections from all experimental joints at both 3 weeks (FIG. 2B) and 12 weeks (FIG. 2C) post-MLI using an automated approach (Visiopharm System). Significant differences between experimental groups were identified via one-way ANOVA with a Tukey's multiple comparisons post-test (*$p<0.05$, **$p<0.01$ compared to Control Sham; $^x p<0.05$, $^{xx}p<0.01$ compared to Control MLI, N=6).

FIGS. 5A-5B: hCol1 reduces MMP13 levels in articular cartilage of mice following MLI. 3 weeks post-injury (Sham or MLI), knee joints were harvested from mice and hypertrophic chondrocytes were analyzed by immunohistochemistry of MMP13 and ColX. Representative sagittal sections depict (FIG. 5A) MMP13 and (FIG. 5B) ColX stained chondrocytes ( ) with cell nuclei counterstained with hematoxylin ( ). Dashed lines highlight the tide mark, separating calcified cartilage from uncalcified cartilage. Joint structures are labeled (F=femur, M=meniscus), and the black scale bar depicts 100 μm.

FIGS. 7A-7C: Synovial hyperplasia is reduced in mice supplemented with hCol1. (FIG. 7A) Tissue sections stained with Safranin O/Fast Green were used to examine the synovium. Representative 40× sagittal sections from Sham and MLI joints of mice supplemented with Control (vehicle, Nutella), LD hCol1 or HD hCol1 that were harvested at 3 and 12 weeks post-injury are depicted. Joint structures are labeled (F=femur, M=meniscus, T=tibia), and synovial membranes are demarcated with black arrows. The black line highlights the thickness of hyperplastic synovium in the Control MLI section and the black scale bar depicts 100 μm. A synovial scoring method was also employed to quantify synovial hyperplasia at both 3 weeks (FIG. 7B) and 12 weeks (FIG. 7C) post-injury. Significant differences between experimental groups were identified via a Kruskal-Wallis Test with a Dunn's multiple comparisons post-test (*$p<0.05$, $p<0.01$, *$p<0.001$ compared to Control Sham, N=6).

FIGS. 8A-8C: Post-injury upregulation of TNF in the synovium is reduced in mice supplemented with hCol1. (FIG. 8A) Representative TNF immunostained sagittal sections (100×) from Sham and MLI joints of mice supplemented with Control (vehicle, Nutella), LD hCol1 or HD hCol1 that were harvested at 3 and 12 weeks post-injury are shown. Joint structures are labeled (F=femur, M=meniscus, T=tibia), synovial membranes are demarcated with arrows, and staining of the tissue indicates intensity and location of TNF expression. The black scale bar depicts 100 μm. mRNA was purified from synovial tissue collected from a separate cohort of similarly-treated mice at 3 weeks (FIG. 8B) and 12 weeks (FIG. 8C) post-injury. qRTPCR was performed to quantify Tnf expression level. Significant differences between groups were identified via one-way ANOVA with a Tukey's multiple comparisons post-test (*$p<0.05$ compared to Control Sham, $^{xx}p<0.01$ compared to Control MLI, N=6).

FIG. 10A: Principal coordinate analysis of microbial abundance from obese control Nutella (1), obese glucosamine (2), obese hCol1 (3), lean hCol1 (4), lean glucosamine (5) and lean control Nutella (6) mice. FIG. 10C shows the relative microbial abundance in lean control mice (Actinobacteria: 19.6127%, Bacteroidetes: 9.9887%, Proteobacteria: 0.0113%, Tenericutes: 1.6302%, Firmicutes: 69%, Verrucomicrobia: 0.0435%), lean hCol1 mice (Actinobacteria: 1.2523%, Bacteroidetes: 8.0434%, Proteobacteria: 0.0010%, Tenericutes: 6.998%, Firmicutes: 83.6593%, Verrucomicrobia: 0.0461%), lean glucosamine mice (Actinobacteria: 12.07091%, Bacteroidetes: 13.4103%, Tenericutes: 1.1749%, Firmicutes: 72.6939%, Verrucomicrobia: 0.0119%), obese control mice (Actinobacteria: 1.4051%, Bacteroidetes: 7.9330%, Proteobacteria: 0.0249%, Firmicutes: 90.5756%, Verrucomicrobia: 0.0613%), obese hCol1 mice (Actinobacteria: 0.4546%, Bacteroidetes: 13.7589%, Proteobacteria: 0.0053%, Tenericutes: 0.0206%, Firmicutes: 85.6624%, Verrucomicrobia: 0.0981%) and obese glucosamine mice (Actinobacteria: 0.4928%, Bacteroidetes: 11.2335%, Proteobacteria: 0.0005%, Firmicutes: 88.0274%, Verrucomicrobia: 0.2458%).

(FIG. 13A) Tissue sections stained with Safranin O/Fast Green were used to examine the synovium. Representative 40× sagittal sections from Sham and MLI joints of mice supplemented with Control (vehicle, Nutella), LD hCol1 or HD hCol1 or hCol2 that were harvested at 3 and 12 weeks post-injury are depicted. Joint structures are labeled (F=femur, M=meniscus, T=tibia), and synovial membranes are demarcated with black arrows. The black line highlights the thickness of hyperplastic synovium in the Control MLI section and the black scale bar depicts 100 µm. A synovial scoring method was also employed to quantify synovial hyperplasia at both 3 weeks (FIG. 13B) and 12 weeks post-injury. Significant differences between experimental groups were identified via a Kruskal-Wallis Test with a Dunn's multiple comparisons post-test (*p<0.05, p<0.01, *p<0.001 compared to Control Sham, N=6).

FIGS. 14A-14C: Post-injury upregulation of TNF in the synovium is reduced in mice supplemented with hCol1 or hCol2. (FIG. 14A) Representative TNF immunostained sagittal sections (100×) from Sham and MLI joints of mice supplemented with Control (vehicle, Nutella), LD hCol1 or HD hCol1 or hCol2 that were harvested at 3 and 12 weeks post-injury are shown. Joint structures are labeled (F=femur, M=meniscus, T=tibia), synovial membranes are demarcated with arrows, and staining of the tissue indicates intensity and location of TNF expression. The black scale bar depicts 100 µm. mRNA was purified from synovial tissue collected from a separate cohort of similarly-treated mice at 3 weeks (FIG. 14B) and 12 weeks (FIG. 14C) post-injury. qRTPCR was performed to quantify Tnf expression level. Significant differences between groups were identified via one-way ANOVA with a Tukey's multiple comparisons post-test (*p<0.05 compared to Control Sham, $^{xx}$p<0.01 compared to Control MLI, N=6).

(FIG. 15A) Microbial rDNA analysis was performed on fecal samples collected from chow fed mice supplemented with control Nutella, 38 mg/day hCol1, or 15 mg/day hCol2 for 4 weeks. Bars show relative microbial abundance in the indicated groups. Each bar represents an average of 3 mice. In the chow diet, hCol 1 and 2 tended to have similar effects: Increases in the abundance of Bacteroidales, Lactobacillales, Turicibacterales, and Anaeroplasmatales. These increases were at the expense of the Clostridiales community in both hCol1 and hCol2 supplemented mice, but this effect was marginal, and Clostridiales was the dominant order of all three groups. Panels depicting the tibia uncalcified cartilage area (FIG. 15B), the number of chondrocytes in the tibia uncalcified cartilage (FIG. 15C), the number (FIG. 15D) and percentage (FIG. 15E) of Safranin-O positive (SafO$^+$) chondrocytes in the tibia uncalcified cartilage, the femur uncalcified cartilage area (FIG. 15F), and the number of chondrocytes in the femur uncalcified cartilage (FIG. 15G) in Sham and DMM chow fed mice supplemented with vehicle (Nutella) (Control DMM), hCol1 (P1 DMM) or hCol2 (P2 DMM) at 12 weeks after injury.

(FIG. 16A) Microbial rDNA analysis was performed on fecal samples collected from lean fed mice supplemented with control Nutella, 38 mg/day hCol1, or 15 mg/day hCol2. Bars show relative microbial abundance in the indicated groups. In the lean diet, hCol1 and 2 also tended to have a similar effect: Most striking was the loss of Bifidobacteriales and emergence of Anaeroplasmatales and a minor decrease in Lactobacillales, Turicibacterales, and Anaeroplasmatales. Panels depicting the tibia cartilage area (FIG. 16B), the tibia uncalcified cartilage area (FIG. 16C), the number of chondrocytes in the tibia uncalcified cartilage (FIG. 16D), and the percentage (FIG. 16E) of Safranin-O positive (SafO$^+$) chondrocytes in the tibia uncalcified cartilage in Sham and DMM lean fed mice supplemented with vehicle (Nutella) (Control DMM), hCol1 (P1 DMM) or hCol2 (P2 DMM) at 12 weeks after injury.

FIG. 17A-17H: (FIG. 17A) Microbial rDNA analysis was performed on fecal samples collected from high fat (HF) (60% of caloric energy from saturated fat) fed mice supplemented with control Nutella, 38 mg/day hCol1, or 15 mg/day hCol2 for 4 weeks. Bars show relative microbial abundance in the indicated groups. In the HF diet, hCol1 and 2 again tended to induce the same effect: ablation of Coriobacteriales and reduction of Lactobacillales. Loss of the Lactobacillales community correlated with an increase in the abundance of Clostridiales. Panels depicting the tibia cartilage area (FIG. 17B), the tibia uncalcified cartilage area (FIG. 17C), the number of chondrocytes in the tibia uncalcified cartilage (FIG. 17D), the number of Safranin-O positive (SafO$^+$) chondrocytes in the tibia uncalcified cartilage (FIG. 17E), the femur uncalcified cartilage area (FIG. 17F), the number of chondrocytes in the femur uncalcified cartilage (FIG. 17G), and the number of Safranin-O positive (SafO$^+$) chondrocytes in the femur uncalcified cartilage (FIG. 17H) in Sham and DMM high fat diet-fed mice supplemented with vehicle (Nutella) (Control DMM), hCol1 (P1 DMM) or hCol2 (P2 DMM) at 3 weeks after injury.

DEFINITIONS

Figure 3A:
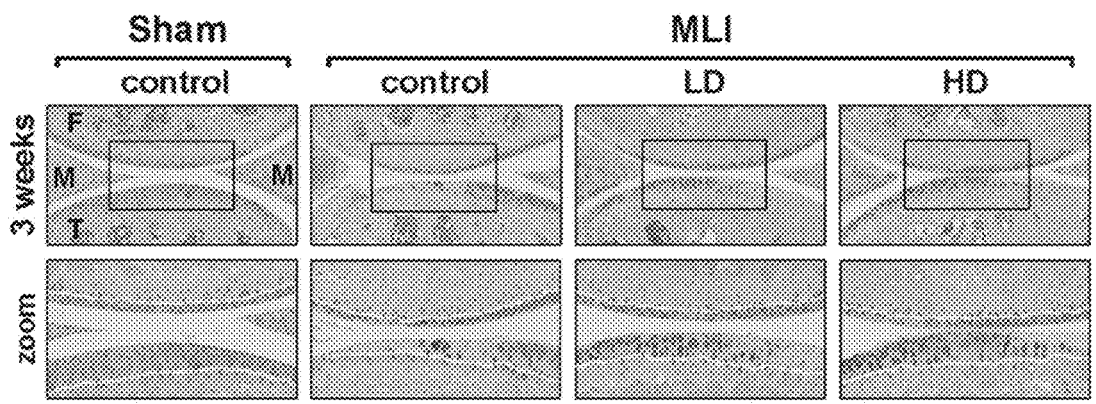
FIGS. 3A-3G: hCol1 is chondroprotective in the early stages of murine PTOA. Panel (FIG. 3A) presents an array of representative 40× Safranin O/Fast Green stained sagittal sections (40×) from the medial compartment of sham and MLI joints 3 weeks post-injury under various treatment conditions (control=vehicle, LD=3.8 mg hCol1/day, HD=38 mg hCol1/day). Joint structures are labeled (F=femur, M=meniscus, T=tibia) and the black box denotes the area shown in the zoomed images, where the tidemarks are denoted with a dashed line. Black scale bars depict 100 μm. Cartilage architecture was evaluated using the Osteomeasure System to determine the tibial uncalcified cartilage area (FIG. 3B), tibial calcified cartilage area (FIG. 3C), the number of chondrocytes in the tibial uncalcified cartilage (FIG. 3D), and the number (FIG. 3E) and percentage (FIG. 3F) of Safranin-O positive (SafO$^+$) chondrocytes in the tibial uncalcified cartilage. OARSI scoring of the sections analyzed by histomorphometry was also performed (FIG. 3G). Significant differences between experimental groups in the histomorphometry data (B-F) were identified via one-way ANOVA with a Tukey's multiple comparisons post-test (*$p<0.05$, $p<0.01$, *$p<0.001$ compared to Control Sham; $^x p<0.05$, $^{xx}p<0.01$ compared to Control MLI, N=6). Significant differences between experimental groups in the OARSI data (G) were identified via a Kruskal-Wallis Test with a Dunn's multiple comparisons post-test (*$p<0.05$, compared to Control Sham, N=6).

Unless defined otherwise, all technical and scientific terms used herein have the same meaning as commonly understood by one of ordinary skill in the art to which this invention belongs.

As used herein, the term "hydrolyzed collagen peptides" refers to fragments of collagen that are prepared from animal tissues. Hydrolyzed collagen is produced from collagen found in the bones, skin, and connective tissue of animals. The process of hydrolysis typically involves breaking down the molecular bonds between individual collagen strands and peptides using combinations of physical, chemical or biological means.

As used herein, the term "type 1 hydrolyzed collagen peptides" or "hCol1" refers to a mixture of type I collagen peptides of different molecular weights that are generated via enzymatic digestion of type I collagen extracted from animal connective tissues. Type 1 collagen is generally sourced from skin, tendon, ligaments, vascular ligature, organs, bone (main component of the organic part of bone).

As used herein, the term "type 2 hydrolyzed collagen peptides" or "hCol2" refers to a mixture of type 2 collagen peptides prepared via enzymatic digestion of animal connective tissues that are rich in type 2 collagen. Type 2 collagen is generally sourced from cartilage (main collagenous component of cartilage). Suitable source of type 1 collagen or type 2 collagen may be but are not limited to the hide, skin or cartilage of vertebrates, including, without limitation, porcine, bovine, horse and fish, or molluscae, including, without limitation, jellyfish. Hydrolyzed collagen is usually referred to with its mean molecular weight, indicating the mean molecular weight of the peptides present in the mixture.

As used herein, the term "Tenericutes" refers to a specific phylum of bacteria that resides in the gastrointestinal tract, and is altered by hydrolyzed collagen peptides.

As used herein, the term "Anaeroplasmatales" refers to a specific order of bacteria that reside in the gastrointestinal tract, and are altered by hydrolyzed collagen peptides.

As used herein, the term "*Bifidobacteria*" refers to a specific genus of bacteria that resides in the gastrointestinal tract, and is altered by oligofructose. Species in the genus *Bifidobacteria* include *bifidum, breve, longum, animalis, pseudolongum, lactis, adolescentis, pseudocatenulatum, infantis, bifidus,* and other species classified in the genus *Bifidobacterium,* including those not identified to date. (Famouri et al. *Pediatric Gastroenterology and Nutrition.* 64(3):p. 413-417; Hughes et al. *Open Bio.* 2017. 7(1); Meng et al. *Gastrointestinal and Liver Physiology.* 2016. 311(4); Sheikhi et al. *Drug Research.* 2016. 66(6): p. 300-305; Cani et al. *Diabetologia.* 2007. 50(11): p. 2374-83; Bernini et al. *Nutrition.* 2016. 32(6): p. 716-719; Reichold et al. *Journal of Nutritional Biochemistry.* 2014. 25(2): p. 118-125; Moratalla et al. *Journal of Hepatology.* 2016. 64(1): p. 135-145; Guo et al. *Journal of Pediatric Gastroenterology and Nutrition.* 2017. 64(3): p. 404-412; Palumbo et al. *Biomedical Papers of the Medical Faculty of the University Palacky.* 2016. 160(3): p. 372-377.

As used herein, the term "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

As used herein, the terms "treatment" or "treating" a disease or disorder refers to a method of reducing, delaying or ameliorating such a condition before or after it has occurred. Treatment may be directed at one or more effects or symptoms of a disease and/or the underlying pathology. The treatment can be any reduction and can be, but is not limited to, the complete ablation of the disease or the symptoms of the disease. As compared with an equivalent untreated control, such reduction or degree of prevention is at least 5%, 10%, 20%, 40%, 50%, 60%, 80%, 90%, 95%, or 100% as measured by any standard technique.

As used herein, the terms "prevent", "preventing", or "prevention" refer to a method for precluding, delaying, averting, or stopping the onset, incidence, severity, or recurrence of a disease or condition. For example, a method is considered to be a prevention if there is a reduction or delay in onset, incidence, severity, or recurrence of a disease or condition or one or more symptoms thereof in a subject susceptible to the disease or condition as compared to a subject not receiving the method. The disclosed method is also considered to be a prevention if there is a reduction or delay in onset, incidence, severity, or recurrence of osteoporosis or one or more symptoms of a disease or condition in a subject susceptible to the disease or condition after receiving the method as compared to the subject's progression prior to receiving treatment. Thus, the reduction or delay in onset, incidence, severity, or recurrence of osteoporosis can be about a 5, 10, 20, 30, 40, 50, 60, 70, 80, 90, 100%, or any amount of reduction in between.

As used herein, the term "pharmaceutically acceptable" excipient, carrier, or diluent refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; phosphate buffer solutions; and other non-toxic compatible substances employed in pharmaceutical formulations. Wetting agents, coloring agents, release agents, coating agents, sweetening, flavoring and perfuming agents, and preservatives can also be present in the compositions.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

As used herein, the term "low dosage" refers to at least 5% less (e.g., at least 10%, 20%, 50%, 80%, 90%, or even 95%) than the lowest standard recommended dosage of a particular compound formulated for a given route of administration for treatment of any human disease or condition. For example, a low dosage of an agent that is formulated for administration by inhalation will differ from a low dosage of the same agent formulated for oral administration.

As used herein, the term "high dosage" is meant at least 5% (e.g., at least 10%, 20%, 50%, 100%, 200%, or even 300%) more than the highest standard recommended dosage of a particular compound for treatment of any human disease or condition.

Any appropriate route of administration can be employed, for example rectal, or oral administration. Most suitable means of administration for a particular patient will depend on the nature and severity of the disease or condition being treated or the nature of the therapy being used and on the nature of the active compound.

Solid dosage forms for oral administration include capsules, tablets, pills, powders, and granules. In such solid dosage forms, the compounds and organisms described herein or derivatives thereof are admixed with at least one inert customary excipient (or carrier) such as dicalcium phosphate or (i) fillers or extenders, as for example, starches, lactose, sucrose, glucose, mannitol, and silicic acid, (ii) binders, as for example, carboxymethylcellulose, alignates, gelatin, polyvinylpyrrolidone, sucrose, and acacia, (iii) humectants, as for example, glycerol, (iv) disintegrating agents, as for example, agar-agar, calcium carbonate, potato or tapioca starch, alginic acid, certain complex silicates, and sodium carbonate, (v) solution retarders, as for example, paraffin, (vi) absorption accelerators, as for example, quaternary ammonium compounds, (vii) wetting agents, as for example, glycerol monostearate, (viii) adsorbents, as for example, kaolin and bentonite, and (ix) lubricants, as for example, talc, calcium stearate, magnesium stearate, solid polyethylene glycols, or mixtures thereof. In the case of capsules, tablets, and pills, the dosage forms may also comprise buffering agents. Solid compositions of a similar type may also be employed as fillers in soft and hard- filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others known in the art.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other bacterial-compatible solvents, for example, oils, in particular, cottonseed oil, groundnut oil, corn germ oil, olive oil, castor oil, sesame oil, glycerol, polyethyleneglycols, and fatty acid esters of sorbitan, or mixtures of these substances, and the like. Besides such inert diluents, the composition can also include additional agents, such as wetting, suspending, sweetening, flavoring, or perfuming agents.

A "prebiotic" generally refers to a substrate that is selectively utilized by host microorganisms to confer a health benefit to the host (Gibson et al. 2017 *Nature Reviews Gastroenterology & Hepatology* 14:491-502).

As used herein, the phrase "improving the gut microbiome" refers to any beneficial effect on the gut microbiome, and may include, without limitation, one or more of enhancing one or more beneficial bacteria in the gut, reducing harmful bacteria in the gut, inhibiting the activity of harmful bacteria in the gut and/or increasing the microbial diversity in the gut.

A "dietary supplement", also known as "food supplement" or "nutritional supplement", is a preparation intended to supplement the diet and provide nutrients that may be missing or may not be consumed in sufficient quantities in a person's diet.

Materials, compositions, and components disclosed herein can be used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

DETAILED DESCRIPTION OF THE INVENTION

The invention provides novel compositions, and methods of use thereof, of collagen-based peptides and key digestive tract microbes combined as a dual orally consumed mixture to support joint, skin and/or bone health. The invention is based in part on the unexpected discovery that hydrolyzed collagen peptides have effects on the gut microbiome, which are associated with positive effects in OA, joint health, skin health and bone health.

The present invention enables a novel approach that utilizes hydrolyzed type 1 and/or type 2 collagen peptides (hCol1/2) as prebiotics alone or in combination with a probiotic mixture (e.g., microbes from the phylum Tenericutes, from the order Anaeroplasmatales or the genus *Bifidobacterium*) as dietary supplements (e.g., oral consumption on a daily, twice weekly, or weekly basis) that have a biological effect rooted in distinct and specific changes in the populations of resident intestinal microbes. The compositions of the invention can be formulated as a mixture that may be added to food or compressed into a tablet or capsule.

Hydrolyzed collagens are fragments of collagen that are prepared from animal tissues for use as food additives or nutraceutical dietary supplements.

hCol1 is a mixture of type I collagen peptides of different molecular weights that are generated via enzymatic digestion of type I collagen extracted from animal connective tissues. hCol1 is considered safe as an oral supplement. The peptide mixture, which contains an abundance of hydroxyproline, proline and glycine, is absorbed dose-dependently following bolus oral delivery, with a series of di- and tri-peptides peaking in the circulation within one hour after consumption in humans. (FDA Database of Select Committee on GRAS Substances (SCGRAS) Opinion: Gelatin 1975 [updated Sep. 29, 2015], http://www.fda.gov/Food/IngredientsPackagingLabeling/GRAS/SCOGS/ucm261307.htm; Shigemura et al. 2014 *Food Chem.* 159:328-32; Ichikawa et al. 2010 *Int J Food Sci Nutr.* 61(1):1-9.)

hCol2 is prepared from animal connective tissues that are rich in type 2 collagen. hCol2 peptide mixtures contain an abundance of hydroxyproline, proline and glycine and glycosaminoglycans. These fragments are absorbed dose-dependently following bolus oral delivery, with a series of di- and tri-peptides peaking in the circulation within one hour after consumption in humans. (Shigemura et al. 2014 *Food Chem.* 159:328-32; Ichikawa et al. 2010 *Int J Food Sci Nutr.* 61(1):1-9.)

The concept that oral consumption of matrix components from cartilage and connective tissue may be effective in treating arthritic conditions has been debated since the mid 1980s. Among these agents, the most widely recognized, heavily studied, and broadly available are glucosamine and chondroitin sulfate, with published evidence suggesting that they are joint protective in OA based on work in animal models and humans. (Deparle et al. 2005 *J Vet Pharmacol Ther.* 28(4):385-90; Christgau et al. 2004 *Clinical and experimental rheumatology* 22(1):36-42; Bruyere et al. 2006 *Annals of the Rheumatic Diseases* 65(8):1050-4; Bruyere et al. 2007 *Drugs & aging* 24(7):573-80; Bruyere et al. 2016 *Seminars in arthritis and rheumatism* 45(4 Suppl): S12-7.)

Fueling the efficacy debate, the widely cited Glucosamine/Chondroitin Sulfate Arthritis Intervention Trial known as GAIT concluded that these agents are not symptom-relieving or disease modifying in human OA. Despite these and other conflicting reports, and without definitive preclinical study of joint tissue effects, glucosamine and chondroitin sulfate have been continued to be widely marketed as nutraceuticals that are joint protective and symptom relieving in various types of arthritis. (Clegg et al. 2006 *New England Journal of Medicine* 354(8):795-808; Deal et al. 1999 *Rheum Dis Clin North Am.* 25(2):379-95; Mevel et al. 2014 *Drug Discov Today* 19(10):1649-58; Bottegoni et al. 2014 *Carbohydr Polym.* 109:126-38).

Figure 19:
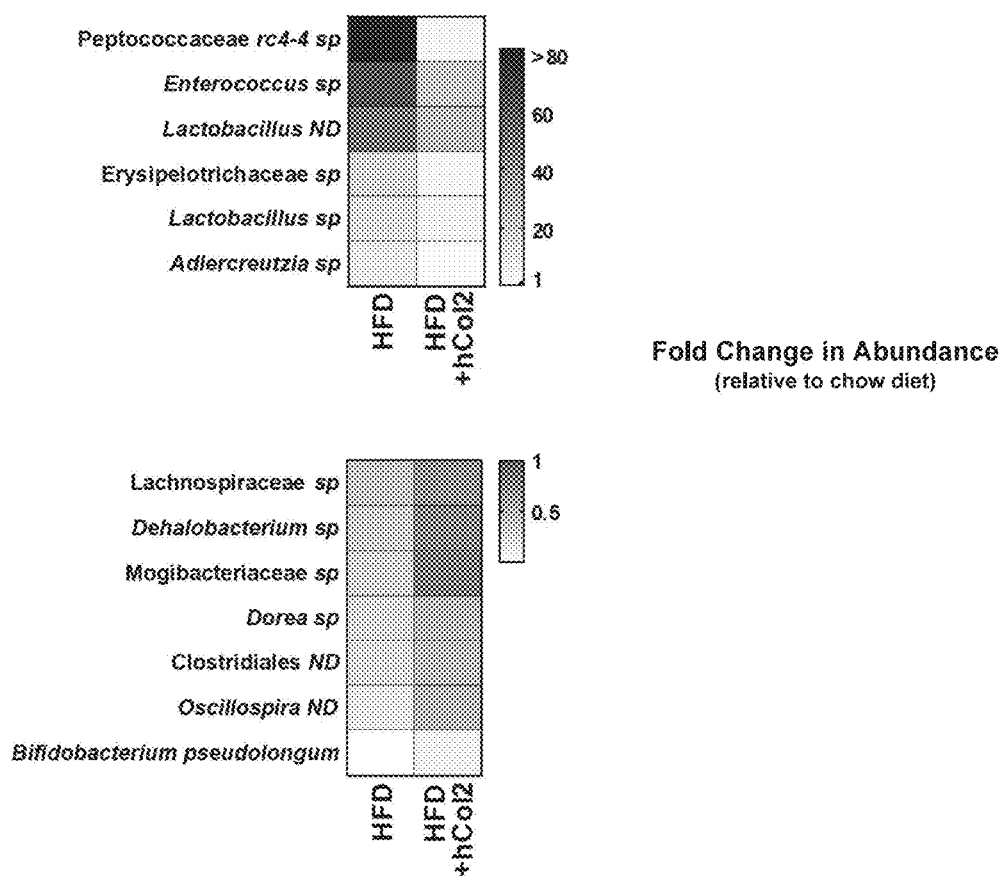
FIG. 19: hCol2 alters the gut microbiome. Mice fed chow or high fat diet for 3 months were supplemented daily with hCol2 (HFD+hCol2) or vehicle (Nutella) (HFD) for 4 weeks. Fecal samples were collected and microbial rDNA analysis was performed. A subset of bacterial species was altered in high fat diet-fed mice compared to chow fed mice, and hCol2 supplementation changed the gut microbiome of these high fat diet-fed mice. Numerous proinflammatory species, particularly *Peptococcaceae* rc4-4 sp, were reduced in hCol2-supplemented mice (top heat map). Conversely, several anti-inflammatory species were enhanced in hCol2-supplemented animals, including *Bifidobacterium pseudolongum* (bottom heat map).

As demonstrated herein, daily oral bolus delivery of hCol1 and hCol2 peptides potently protects against OA progression in an injury model of disease and supports skin health and has beneficial effects in mineralized skeletal tissues that are associated with a robust effect on the gut microbiome characterized primarily by enhancement of microbes in the phylum Tenericutes and in the orders Anaeroplasmatales and Clostridiales (FIGS. 10, 15, 16, 17). Certain proinflammatory species, in particular *Peptococcaceae* rc4-4 sp, were reduced in hCol2-supplemented mice, whereas anti-inflammatory species, including *Bifidobacterium pseudolongum*, were enhanced (FIG. 19). Evidence disclosed herein not only solidly identifies joint protective effects of hCol1 and hCol2 in posttraumatic OA and obesity-induced OA, but it identifies marked effects on the gut microbiome, with specific population expansion of microbes in the phylum Tenericutes and the orders Anaeroplasmatales and Clostridiales, and reduction of pro-inflammatory species and increase of anti-inflammatory species, that are associated with systemic effects that play out in joints, skin and bone.

An experimental protocol was carried out in this study that involved daily oral delivery of hCol1 and hCol2 to mice that were induced to develop PTOA via surgical administration of a meniscal-ligamentous injury (FIG. 1). Two doses of hCol1 were chosen, with the higher dose (38 mg/day) set to be the body weight equivalent to the human dose (7.4 g/day) that was previously employed in a clinical study. (Jiang et al. 2014 *Agro food industry Hi Tech.* 25(2):19-23.)

Figure 6:
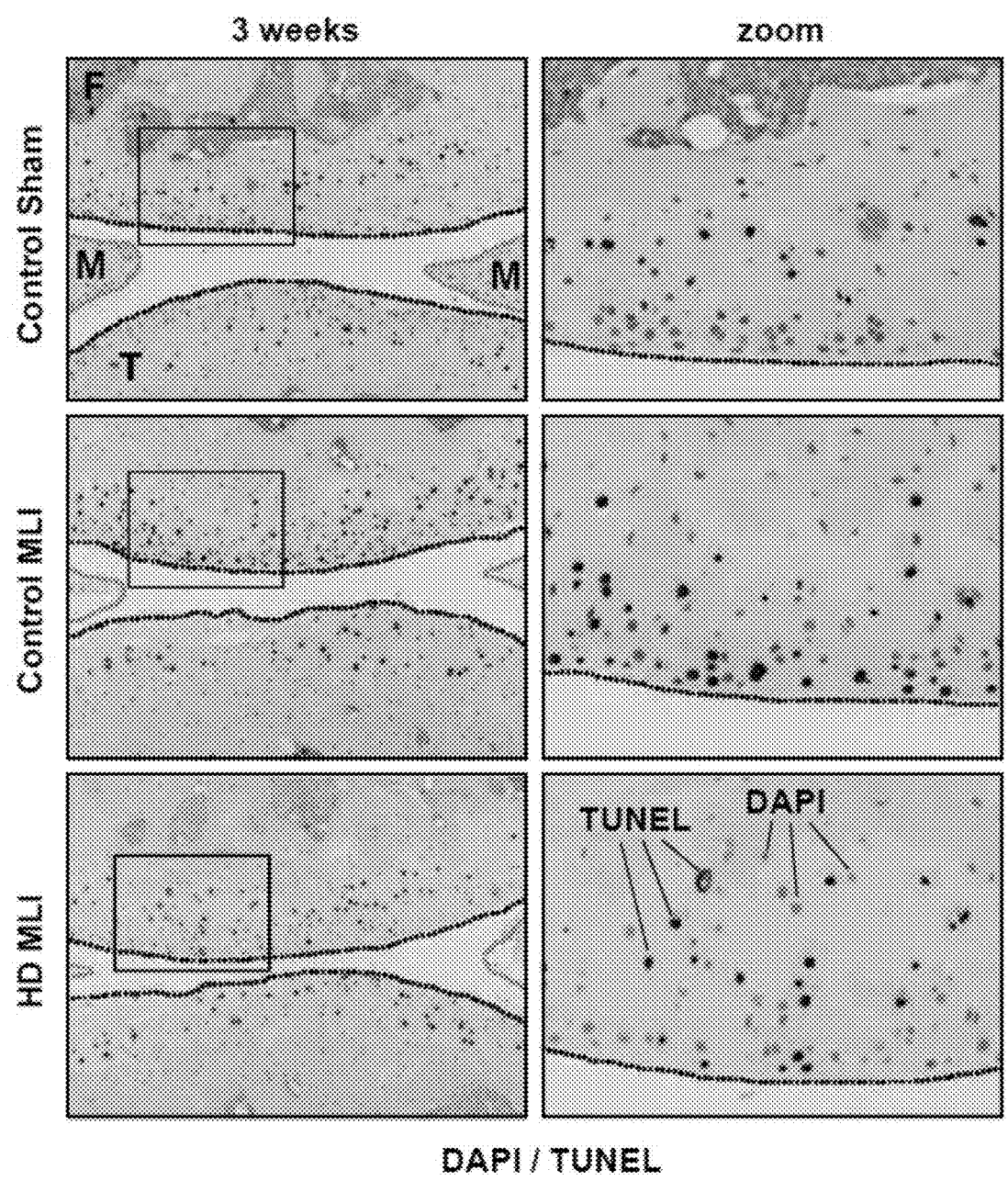
FIG. 6: Chondrocyte apoptosis post-MLI is reduced in hCol1-supplemented mice. Joints were harvested from mice 3 weeks post-injury (Sham or MLI) and apoptotic cells were identified via TUNEL staining. Representative 100× sagittal sections (right column of panels) show the overall scope of cellular apoptosis (green), with all cell nuclei DAPI labeled (blue). The yellow dashed lines depict the articular cartilage surface and the red dashed lines outline the anterior and posterior horns of the meniscus. The region demarcated with the white box is magnified in the right column (zoom). White scale bars depict 100 μm.

To investigate the hypothesized joint-protective impact of long-term use, mice were supplemented with hCol1 for a one-month pre-treatment period, followed by administration of MLI surgery and subsequent assessment of joints. Structural and cellular evaluation of the articular cartilage of sham and injured knee joints using both automated and manual histomorphometric methods revealed that while there were no discernable cartilage effects in the sham/normal joints, at early and later time points in the development of OA, mice administered hCol1 were chondroprotected, particularly at 12 weeks post-injury. Uncalcified tibial articular cartilage was preserved and the articular chondrocyte population was maintained (FIGS. 2, 3, 4), possibly via reduction of MMP13 and inhibition of chondrocyte apoptosis (FIGS. 5 and 6, respectively). Regarding apoptosis specifically, its inhibition was particularly apparent on the femoral condyles (FIG. 6), which correlated with the complete protection from cartilage loss in this region of the joint (FIG. 4). Interestingly, chondrocyte populations were not only preserved, but the number of cells actively producing Safranin O stained proteoglycan matrix was increased significantly in the hCol1-treated groups at both time points.

In addition to the remarkable cartilage and chondrocyte effects observed in the degenerating knee of mice supplemented with hCol1, significant changes were also observed in the synovium. While there were no discernable synovial effects of the supplements in sham operated joints, synovial hyperplasia was evident at both early and late time points following injury (3 and 12 weeks respectively), with semi-quantitative scoring revealing significant protection from this hyperplasia in mice supplemented with hCol1 (FIG. 7).

This protection was accompanied by reduced TNF protein and mRNA expression, suggesting an anti-inflammatory effect of hCol1 on the OA joint (FIG. 8). This protection seemed to be restricted to TNF; synovial mRNA expression of other cytokines and catabolic factors known to participate in articular cartilage degeneration, including Il1b, Mmp13 and ADAMTS5, were not affected in the hCol1 supplemented groups (data not shown).

While hCol1 and other similar collagen-based supplements have not been shown to protect against the production of inflammatory mediators in joint tissue, there is evidence of anti-inflammatory effects of type 1 collagen hydrolysate and peptides in cardiovascular disease and in ulcerative colitis. Of note, the anti-inflammatory effects of oral hCol1 in the synovium described herein parallel the anti-inflammatory effects that have been reported for glucosamine, chondroitin sulfate and glycosaminoglycans. Overall, when considered in conjunction with the observed cartilage structure modifications, daily oral supplementation with hCol1 has significant potential as a cartilage protective and anti-inflammatory agent in the treatment of OA. (Bottegoni et al. 2014 *Carbohydr Polym.* 109:126-38; Zhang et al. 2010 *J Nutr Sci Vitaminol (Tokyo)* 56(3):208-10; Ramadass et al. 2016 *Eur J Pharm Sci.* 91:216-24; Henrotin et al. 2014 *Seminars in arthritis and rheumatism* 43(5):579-87.)

It is further shown herein that oral administration of both hCol1 and hCol2 improves bone health (FIG. 20).

The detailed analysis of joint structure that was disclosed herein, showing positive effects of hCol1 on articular cartilage architecture and synovial hyperplasia, clearly establishes a disease modifying approach by which to address OA joint degeneration via a dietary supplement. Missing from many prior studies is the direct examination of the impact of these agents on cartilage architecture, chondrocyte populations and synovial status in animal models of disease.

With regard to the mechanism of action of hCol1 and other nutraceuticals including type 2 collagen-based preparations and hCol1, and without wishing to be bound by the theory, a hypothesis is that these agents, or their digested fragments, are absorbed across the intestinal lumen, enter the blood stream and have direct effects on articular chondrocytes or other cells in the joint and/or influence the microbial profile in the colon that prevents inflammation both locally and systemically, with implications in joints, skin and bone.

Figure 12:
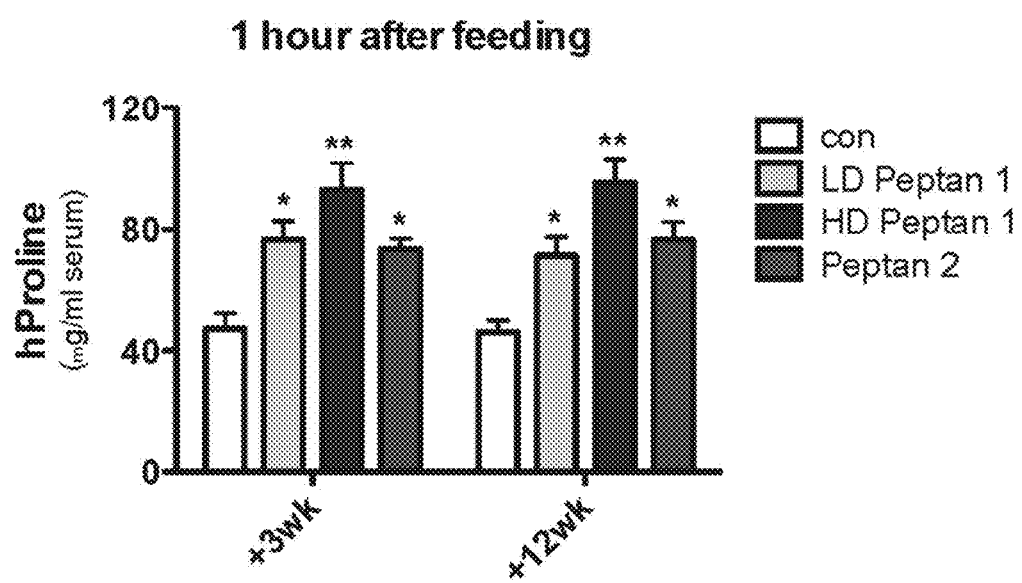
FIG. 12: Like hCol1 (FIG. 1), successful delivery of hCol2 was confirmed by quantifying serum hProline via ELISA. Serum samples collected 1 week before (−1) and 2 weeks after surgery were harvested 3 hours after the mice consumed supplements (not shown). Serum samples collected 3 and 12 weeks after surgery were harvested 1 hour after consumption of the supplements. Significant differences between groups were identified via one-way ANOVA with a Tukey's multiple comparisons post-test (*p<0.05, **p<0.01 compared to Control, N=6).

Consistent with this theory, a significant dose dependent surge was detected in serum hydroxyproline levels in mice that were supplemented with hCol1 (FIG. 1). Serum hydroxyproline was highest when blood was sampled within 1 hour of consumption (FIG. 1E), although the surge was still detectable at 3 hours in the high dose hCol1 group (FIG. 1D). This effect was also observed in mice presented hCol2 as a supplement, with significant impact on circulating hydroxyproline levels that paralleled the hCol2 effect (FIG. 12).

Once in the serum, these peptide fragments presumably have access to all organ systems, with one report confirming distribution of a radiolabeled preparation to skeletal elements, muscle, skin and cartilage in rats. Another study performed in rats provides autoradiographic evidence for the presence of radiolabeled proline-hydroxyproline dipeptide in articular cartilage and synovium within 30 minutes of ingestion. (Watanabe-Kamiyama et al. 2010 *Journal of agricultural and food chemistry* 58(2):835-41; Kawaguchi et al. 2012 *Biol Pharm Bull.* 35(3):422-7.)

It was surprisingly found that oral administration of hydrolyzed collagen peptides alters the gut microbiome (FIG. 10, 11, 15-17, 19). To further investigate this effect a series of similar experiments was performed where both hCol1 and hCol2 were compared side by side (FIG. 12-18, 20, 21). It was found that both hCol1 and hCol2 supplementation resulted in altered gut microbiome but also both resulted in an improvement in an osteoarthritis model, resulting in less cartilage degradation, improved chondrocyte viability and matrix-producing activity. Also, both hCol1 and hCol2 demonstrated an anti-inflammatory effect as demonstrated by the reduced synovial hyperplasia (FIG. 13) and Tnf expression data (FIG. 14).

The discovery that oral supplementation with hCol1 and hCol2 alters the gut microbiome, specifically supporting expansion of the Tenericutes community and microbes in the order Anaeroplasmatales, has led to a novel approach to using orally consumed agents like hCol1 and hCol2 to provide health benefits systemically via a diverse array of effects that they provide. The novel approach is exemplified in the combination of the hCol1 and hCol2 supplement (as a prebiotic) with a seed culture of Tenericutes and/or the members of the order Anaeroplasmatales and/or the genus *Bifidobacteria* (as a probiotic), in particular with *Bifidobacterium pseudolongum,* to maximize therapeutic and health promoting effects in joints and in OA, in joint, in skin, and in bone.

For example, typical doses of hCol (0.8-15 gm/day, either hCol1 or hCol2, or a mixture) with $10^7$-$10^{12}$ colony forming units of a mixed culture of Tenericutes and/or members of the order Anaeroplasmatales and/or the genus *Bifidobacteria* that can be delivered as a mixture in a drink, can be combined into a food product (e.g., yogurt), or may be processed into tablet or capsule forms. The supplementation regimen can encompass consuming the combination formulation one time/day, two times per week, or one time per week, etc.

In one aspect, the invention generally relates to a composition for use in preventing or treating a disease or disorder in a subject in need thereof or for providing health-supporting effects or a health benefit to a subject in need thereof, wherein the composition comprises hydrolyzed collagen peptides. In alternative aspects the invention also relates to a therapeutic method comprising administering a composition comprising hydrolyzed collagen peptides to a subject in need thereof. The invention further relates to the use of a composition comprising hydrolyzed collagen peptides for the manufacture of a medicine for a subject in need thereof. Yet an alternative aspect relates to the use of a composition comprising hydrolyzed collagen peptides for providing health-supporting effects or a health benefit. In preferred embodiments, the composition is used for providing a health benefit to skin, joint or bone.

In a preferred embodiment of the invention the composition for use in prevention or treatment, the therapeutic method or the medicine is for preventing or treating a disease or disorder of the joints, skin or bone, preferably wherein the disease is osteoarthritis, or a related disease, or to provide health effects in these organs. In further embodiments, the composition for use, the therapeutic method or the medicine is for preventing or treating inflammation, preferably inflammation in joint or wherein the inflammation is related to synovial hyperplasia.

Diseases or disorders of the joint, skin or bone are known to the skilled person and may relate to but are not limited to: Ambe, Avascular necrosis or Osteonecrosis, Arthritis, Bone spur (Osteophytes), Craniosynostosis, Coffin-Lowry syndrome, Fibrodysplasia ossificans progressiva, Fibrous dysplasia, Fong Disease (or Nail-patella syndrome), Fracture, Giant cell tumor of bone, Greenstick Fracture, Gout, Hypophosphatasia, Hereditary multiple exostoses, Klippel-Feil syndrome, Metabolic Bone Disease, Multiple myeloma, Nail-patella syndrome, Osteoarthritis, Osteitis deformans (or Paget's disease of bone), Osteitis fibrosa cystica (or Osteitis fibrosa, or Von Recklinghausen's disease of bone), Osteitis pubis, Condensing osteitis (or Osteitis condensas), Osteochondritis dissecans, Osteochondroma (bone tumor), Osteogenesis Imperfecta, Osteomalacia, Osteomyelitis, Osteopenia, Osteopetrosis, Osteoporosis, Porotic hyperostosis, Primary hyperparathyroidism, Renal Osteodystrophy, Salter-Harris fractures, Scoliosis. Disease or diorders of the skin or bones may also relate to diseases of the joint or arthropathy, such as but not limited to: Arthritis, Spondylarthropathy, Arthropathy, Reactive arthropathy, Enteropathic arthropathy, Crystal arthropathy, Diabetic arthropathy, Neuropathic arthropathy.

Osteoarthritis (OA) is known to the skilled person as a type of joint disease that results from breakdown of joint cartilage and underlying bone. A related disease may be a disease with similar symptoms or similar underlying causes. A related disease may also refer to secondary osteoarthritis, where the osteoarthritis is caused by other factors such as Alkaptonuria, Congenital disorders of joints, Diabetes, Ehlers-Danlos Syndrome, Hemochromatosis and Wilson's disease, Inflammatory diseases, Injury to joints or ligaments, Marfan syndrome, Obesity, Joint infection. In embodiments, osteoarthritis is posttraumatic osteoarthritis or obesity-induced osteoarthritis.

Inflammation is known to the skilled person, and may be caused by the skin or bone disease or disorder, the osteoarthritis or related disease, or the inflammation may be the cause of the skin or bone disease or disorder, the osteoarthritis or related disease. Preferably the inflammation is caused by or causing synovial hyperplasia.

In one aspect, the invention generally relates to a composition for use in treating a disease or disorder or providing a health benefit, wherein the composition comprises hydrolyzed collagen peptides.

In certain embodiments of the composition, the use is for preventing or treating a disease or disorder in skin, joint or bone or providing a health benefit to skin, joint or bone.

In certain embodiments of the composition, the use is for preventing or treating inflammation, preferably wherein the disease is osteoarthritis, in particular posttraumatic osteoarthritis or obesity-induced osteoarthritis, or a related disease or disorder.

In certain embodiments of the composition, the inflammation is related to synovial hyperplasia.

Any suitable hydrolyzed collagen peptides may be used. Preferably the composition comprising hydrolyzed collagen according to the invention comprises hCol1 or hCol2 or a combination thereof, preferably hCol1 or hCol2 or both are present in the composition according to the invention having a mean molecular weight in a preferred range as mentioned herein.

In certain embodiments of the composition, the hCol1 has a mean molecular weight between about 300 Da and about 7500 Da (e.g., between about 600 Da and about 6000 Da, between about 1000 Da and about 5000 Da, between about 1300 Da and about 4500 Da, between about 1600 and about 4000 Da, between about 1800 Da and about 3500 Da, between about 2000 and about 3000 Da) and/or wherein the hCol2 has a mean molecular weight between about 300 Da and about 7500 Da (e.g., between about 600 Da and about 6000 Da, between about 1000 Da and about 5000 Da, between about 1300 Da and about 4500 Da, between about 1600 and about 4000 Da, between about 1800 Da and about 3500 Da, between about 2000 and about 3000 Da).

In certain embodiments of the composition, the hCol1 originates from bovine, porcine or fish collagen from skin or hide or bone, preferably skin or hide, i.e. the hCol1 is produced by enzymatic hydrolysis of collagen from bovine, porcine or fish skin or hide or bone and/or the hCol12 originates from bovine, porcine or fish collagen from cartilage, i.e. the hCol2 is produced by enzymatic hydrolysis of collagen from bovine, porcine or fish cartilage.

In certain embodiments of the composition, it is suitable for oral administration.

In certain embodiments of the composition, it is suitable for daily, thrice weekly, twice weekly, or weekly administration.

In another aspect, the invention generally relates to a combination for use in preventing or treating a disease or disorder or providing a health benefit, wherein the combination comprises the above composition and microbes from the phylum Tenericutes and/or the order Anaeroplasmatales and/or the genus *Bifidobacteria* in the same composition as the hydrolyzed collagen, or wherein the microbes are present in a separate composition. A related aspect is directed to the use of said combination comprising hydrolyzed collagen peptides and microbes from the phylum Tenericutes and/or the order Anaeroplasmatales and/or the genus *Bifidobacteria* in the same composition as the hydrolyzed collagen peptides, or wherein the microbes are present in a separate composition, for providing a health benefit.

In certain embodiments of the combination, the amount of microbes from the phylum Tenericutes and/or the order Anaeroplasmatales and/or the genus *Bifidobacteria* are present in an amount effective for preventing or treating osteoarthritis or a related disease or disorder.

In certain embodiments of the combination, the amount of microbes from the phylum Tenericutes and/or the order Anaeroplasmatales and/or the genus *Bifidobacteria* are present in an amount effective for preventing or treating inflammation, in particular inflammation related to synovial hyperplasia.

In certain embodiments of the combination, the microbes are from the phylum Tenericutes and/or the genus *Bifidobacteria*. In embodiments of the combination, the microbes are from the genus *Bifidobacteria*, preferably *Bifidobacterium pseudolongum*.

In yet another aspect, the invention generally relates to a composition comprising hydrolyzed collagen peptides and microbes from the phylum Tenericutes and/or the order Anaeroplasmatales and/or the genus *Bifidobacteria*. In embodiments of the composition, the microbes are from the genus *Bifidobacteria*, preferably *Bifidobacterium pseudolongum*. In certain embodiments of the composition, the hydrolyzed collagen peptides are hCol1 and/or hCol2.

In certain embodiments of the combination, the microbes are from the phylum Tenericutes and/or the genus *Bifidobacteria*.

In yet another aspect, the invention generally relates to a unit dosage form comprising a composition disclosed herein, wherein the unit dosage form is a tablet, capsule, powder or liquid.

In yet another aspect, the invention generally relates to a unit dosage form comprising a combination disclosed herein, wherein the unit dosage form is a tablet, capsule, powder or liquid.

More preferably, the composition comprises a unit dosage from about 1.5 grams to about 15, more preferably 2 to 12, more preferably 2.5 to 10, more preferably 3 to 8.5, more preferably 3.5 to 7.5, more preferably 4 to 6.5, most preferably 4.5 to 5.5, hCol1 and/or comprises a unit dosage from about 0.9 grams to about 7.5, more preferably 1.0 to 7.0, more preferably 1.2 to 6.5, more preferably 1.4 to 6.0, more preferably 1.6 to 5.5, more preferably 1.8 to 5.0, more preferably 2.0 to 4.5, more preferably 2.5 to 4.0 most preferably 3.0 to 3.5 grams of hCol2 and/or preferably comprises a unit dosage from about $10^8$ CFU to about $10^{11}$, more preferably about $10^9$ to $10^{10}$ CFU of microbes from the phylum Tenericutes and/or the order Anearoplasmatales, and/or and/or the genus *Bifidobacteria*.

In certain embodiments of the unit dosage, it comprises from about 0.8 grams to about 15 grams (e.g., from about 1.5 to about 15, from about 2 to about 12, from about 2.5 to about 10, from about 3 to about 8.5, from about 3.5 to about 7.5, from about 4 to about 6.5, from about 4.5 to about 5.5, from about 1.0 to about 7.0, from about 1.2 to about 6.5, from about 1.4 to about 6.0, from about 1.6 to about 5.5, from about 1.8 to about 5.0, from about 2.0 to about 4.5, from about 2.5 to about 4.0, from about 3.0 to about 3.5 grams) of hydrolyzed collagen peptides and/or from about $10^7$ CFU to about $10^{12}$ CFU (e.g., from about $10^7$ colony forming units (CFU) to about $10^{11}$ CFU, from about $10^7$ colony forming units (CFU) to about $10^{10}$ CFU, from about $10^7$ colony forming units (CFU) to about $10^9$ CFU, from about $10^8$ colony forming units (CFU) to about $10^{12}$ CFU, from about $10^9$ colony forming units (CFU) to about $10^{12}$ CFU, from about $10^{10}$ colony forming units (CFU) to about $10^{12}$ CFU, from about $10^8$ colony forming units (CFU) to about $10^{11}$ CFU) of microbes from the phylum Tenericutes and/or the order Anaeroplasmatales and/or the genus *Bifidobacteria*.

In certain embodiments of the unit dosage, the hCol1 has a mean molecular weight between about 300 Da and about 7500 Da (e.g., between about 600 Da and about 6000 Da, between about 1000 Da and about 5000 Da, between about 1300 Da and about 4500 Da, between about 1600 and about 4000 Da, between about 1800 Da and about 3500 Da, between about 2000 and about 3000 Da) and/or wherein the hCol2 has a mean molecular weight between about 300 Da and about 7500 Da (e.g., between about 600 Da and about 6000 Da, between about 1000 Da and about 5000 Da, between about 1300 Da and about 4500 Da, between about 1600 and about 4000 Da, between about 1800 Da and about 3500 Da, between about 2000 and about 3000 Da).

In certain embodiments of the unit dosage, the hCol1 originates from bovine, porcine or fish collagen from skin or hide or bone, preferably skin or hide, or from jellyfish and/or the hCol12 originates from bovine, porcine or fish collagen from cartilage.

In certain embodiments of the unit dosage, the microbes are from the phylum Tenericutes and/or the genus *Bifidobacteria*. In embodiments of the unit dosage, the microbes are from the genus *Bifidobacteria*, preferably *Bifidobacterium pseudolongum*.

In yet another aspect, the invention generally relates to a package or kit comprising a composition comprising hydrolyzed collagen peptides and a composition comprising microbes from the phylum Tenericutes and/or the order Anaeroplasmatales and/or the genus *Bifidobacteria*, or a composition comprising both hydrolyzed collagen peptides and microbes from the phylum Tenericutes and/or the order Anaeroplasmatales and/or the genus *Bifidobacteria*.

In certain embodiments of the package or kit, the hydrolyzed collagen peptides are hCol1 and/or hCol2.

In certain embodiments of the package or kit, it comprises from about 0.8 grams to about 15 grams (e.g., from about 1.5 to about 15, from about 2 to about 12, from about 2.5 to about 10, from about 3 to about 8.5, from about 3.5 to about 7.5, from about 4 to about 6.5, from about 4.5 to about 5.5, from about 1.0 to about 7.0, from about 1.2 to about 6.5, from about 1.4 to about 6.0, from about 1.6 to about 5.5, from about 1.8 to about 5.0, from about 2.0 to about 4.5, from about 2.5 to about 4.0, from about 3.0 to about 3.5 grams) of hydrolyzed collagen peptides and/or from about $10^7$ CFU to about $10^{12}$ CFU (e.g., from about $10^7$ colony forming units (CFU) to about $10^{11}$ CFU, from about $10^7$ colony forming units (CFU) to about $10^{10}$ CFU, from about $10^7$ colony forming units (CFU) to about $10^9$ CFU, from about $10^8$ colony forming units (CFU) to about $10^{12}$ CFU, from about $10^9$ colony forming units (CFU) to about $10^{12}$ CFU, from about $10^{10}$ colony forming units (CFU) to about $10^{12}$ CFU, from about $10^8$ colony forming units (CFU) to about $10^{11}$ CFU) of microbes from the phylum Tenericutes and/or the order Anaeroplasmatales and/or the genus *Bifidobacteria*.

In certain embodiments of the package or kit, the hCol1 has a mean molecular weight between about 300 Da and about 7500 Da (e.g., between about 600 Da and about 6000 Da, between about 1000 Da and about 5000 Da, between about 1300 Da and about 4500 Da, between about 1600 and about 4000 Da, between about 1800 Da and about 3500 Da, between about 2000 and about 3000 Da) and/or wherein the hCol2 has a mean molecular weight between about 300 Da and about 7500 Da (e.g., between about 600 Da and about 6000 Da, between about 1000 Da and about 5000 Da, between about 1300 Da and about 4500 Da, between about 1600 and about 4000 Da, between about 1800 Da and about 3500 Da, between about 2000 and about 3000 Da).

In certain embodiments of the package or kit, the hCol1 originates form porcine, bovine or fish collagen from skin or hide or bone, preferably skin or hide, or from jellyfish and/or the hCol12 originates form porcine, bovine or fish collagen from cartilage.

In certain embodiments of the package or kit, the microbes are from the phylum Tenericutes and/or the genus *Bifidobacteria*. In embodiments of the package or kit, the microbes are from the genus *Bifidobacteria*, preferably *Bifidobacterium pseudolongum*.

In yet another aspect, the invention generally relates to use of a composition comprising or consisting essentially of hydrolyzed collagen peptides for modulating or improving the gut microbiome, preferably for increasing the microbial diversity in the gut. A related aspect is directed to a method for modulating or improving the gut microbiome, preferably for increasing the microbial diversity in the gut. The method includes: administering to a subject in need thereof a composition comprising or consisting essentially of hydrolyzed collagen peptides in an amount effective to improve the gut microbiome.

In particular embodiments, the composition comprising hydrolyzed collagen peptides is used for enhancing microbes in the phylum Tenericutes and in the order Anaeroplasmatales and/or the genus *Bifidobacteria*. In embodiments, the composition comprising hydrolyzed collagen peptides is used for enhancing microbes in the order of the Bifidobacterials, the Lactobacillales and/or the Clostridiales.

In yet another aspect, the invention generally relates to use of a composition comprising hydrolyzed collagen peptides as a prebiotic. A related aspect is directed to a method for providing a prebiotic to a subject. The method includes: administering to a subject in need thereof a composition comprising an effective amount of hydrolyzed collagen peptides. In certain embodiments of the use, the hydrolyzed collagen peptides are hCol1 and/or hCol2.

In certain embodiments of the use, it comprises from about 0.8 grams to about 15 grams (e.g., from about 1.5 to about 15, from about 2 to about 12, from about 2.5 to about 10, from about 3 to about 8.5, from about 3.5 to about 7.5, from about 4 to about 6.5, from about 4.5 to about 5.5, from about 1.0 to about 7.0, from about 1.2 to about 6.5, from about 1.4 to about 6.0, from about 1.6 to about 5.5, from about 1.8 to about 5.0, from about 2.0 to about 4.5, from about 2.5 to about 4.0, from about 3.0 to about 3.5 grams) of hydrolyzed collagen peptides.

In certain embodiments of the use, the hCol1 has a mean molecular weight between about 300 Da and about 7500 Da (e.g., between about 600 Da and about 6000 Da, between about 1000 Da and about 5000 Da, between about 1300 Da and about 4500 Da, between about 1600 and about 4000 Da, between about 1800 Da and about 3500 Da, between about 2000 and about 3000 Da) and/or wherein the hCol2 has a mean molecular weight between about 300 Da and about 7500 Da (e.g., between about 600 Da and about 6000 Da, between about 1000 Da and about 5000 Da, between about 1300 Da and about 4500 Da, between about 1600 and about 4000 Da, between about 1800 Da and about 3500 Da, between about 2000 and about 3000 Da).

In certain embodiments of the use, the hCol1 originates form porcine, bovine or fish collagen from skin or hide or bone, preferably skin or hide, or from jellyfish and/or the hCol12 originates form porcine, bovine or fish collagen from cartilage.

In yet another aspect, the invention generally relates to a method for preventing or treating osteoarthritis, in particular posttraumatic osteoarthritis or obesity-induced osteoarthritis, or a related disease or disorder. The method includes: administering to a subject in need thereof a composition comprising hydrolyzed collagen peptides in an amount effective to treat osteoarthritis, or a related disease or disorder thereof. A related aspect is directed to a composition comprising hydrolyzed collagen peptides for use in preventing or treating osteoarthritis, or a related disease or disorder.

In yet another aspect, the invention generally relates to a method for preventing or treating a disease or disorder in the skin, joint or bone. The method includes: administering to a subject in need thereof a composition comprising hydrolyzed collagen peptides in an amount effective to treat the disease or disorder in the skin, joint or bone, or a related disease or disorder thereof. A related aspect is directed to a composition comprising hydrolyzed collagen peptides for use in preventing or treating a disease or disorder in the skin, joint or bone, or a related disease or disorder thereof.

In yet another aspect, the invention generally relates to a method for improving joint health, skin health or bone health. The method includes: administering to a subject in need thereof hydrolyzed collagen peptides and microbes from the phylum Tenericutes and/or the order Anaeroplasmatales and/or the genus *Bifidobacteria*, in a single composition or in separate compositions, in amounts effective improving joint health, skin health or bone health. A related aspect is directed to the use of hydrolyzed collagen peptides and microbes from the phylum Tenericutes and/or the order Anaeroplasmatales and/or the genus *Bifidobacteria*, in a single composition or in separate compositions, for improving joint health, skin health or bone health.

In yet another aspect, the invention generally relates to a method for providing a chondroprotective effect or for protecting cartilage in a subject. The method includes: administering to a subject in need thereof a composition comprising an effective amount of hydrolyzed collagen peptides. In embodiments, the subject is diagnosed with osteoarthritis, preferably posttraumatic osteoarthritis or obesity-induced osteoarthritis. A related aspect is directed to the use of a composition comprising hydrolyzed collagen peptides as described herein as a chondroprotective agent.

In yet another aspect, the invention generally relates to a method for improving gut microbiome and/or for treating a disease or condition related thereto. The method includes: administering to a subject in need thereof a composition comprising hydrolyzed collagen peptides in an amount effective to improve gut microbiome and/or to treat a disease or disorder related thereto.

In certain embodiments of the methods, the hydrolyzed collagen peptides are hCol1 and/or hCol2.

In certain embodiments of the methods, it comprises from about 0.8 grams to about 15 grams (e.g., from about 1.5 to about 15, from about 2 to about 12, from about 2.5 to about 10, from about 3 to about 8.5, from about 3.5 to about 7.5, from about 4 to about 6.5, from about 4.5 to about 5.5, from about 1.0 to about 7.0, from about 1.2 to about 6.5, from about 1.4 to about 6.0, from about 1.6 to about 5.5, from about 1.8 to about 5.0, from about 2.0 to about 4.5, from about 2.5 to about 4.0, from about 3.0 to about 3.5 grams) of hydrolyzed collagen peptides and/or from about $10^7$ CFU to about $10^{12}$ CFU (e.g., from about $10^7$ colony forming units (CFU) to about $10^{11}$ CFU, from about $10^7$ colony forming units (CFU) to about $10^{10}$ CFU, from about $10^7$ colony forming units (CFU) to about $10^9$ CFU, from about $10^8$ colony forming units (CFU) to about $10^{12}$ CFU, from about $10^9$ colony forming units (CFU) to about $10^{12}$ CFU, from about $10^{10}$ colony forming units (CFU) to about $10^{12}$ CFU, from about $10^8$ colony forming units (CFU) to about $10^{11}$ CFU) of microbes from the phylum Tenericutes and/or the order Anaeroplasmatales and/or the genus *Bifidobacteria*.

In certain embodiments of the methods, the hCol1 has a mean molecular weight between about 300 Da and about 7500 Da (e.g., between about 600 Da and about 6000 Da, between about 1000 Da and about 5000 Da, between about 1300 Da and about 4500 Da, between about 1600 and about 4000 Da, between about 1800 Da and about 3500 Da, between about 2000 and about 3000 Da) and/or wherein the hCol2 has a mean molecular weight between about 300 Da and about 7500 Da (e.g., between about 600 Da and about 6000 Da, between about 1000 Da and about 5000 Da, between about 1300 Da and about 4500 Da, between about 1600 and about 4000 Da, between about 1800 Da and about 3500 Da, between about 2000 and about 3000 Da).

In certain embodiments of the methods, the hCol1 originates form porcine, bovine or fish collagen from skin or hide or bone, preferably skin or hide, or from jellyfish and/or the hCol12 originates form porcine, bovine or fish collagen from cartilage.

In certain embodiments of the methods, the hydrolyzed collagen peptides are administered daily, thrice weekly, twice weekly, or weekly.

In certain embodiments of the methods, the microbes from the phylum Tenericutes and/or the order Anaeroplasmatales and/or the genus *Bifidobacteria* are administered daily, thrice weekly, twice weekly, or weekly.

In certain embodiments of the methods, the microbes are from the phylum Tenericutes and/or the genus *Bifidobacteria*. In embodiments of the method, the microbes are from the genus *Bifidobacteria*, preferably *Bifidobacterium pseudolongum*.

In certain embodiments of the methods, administration is performed via oral administration.

In the compositions of hydrolyzed collagen peptides disclosed herein, the hydrolyzed collagen peptides make up the essential proportion of the composition. Accordingly, in particular embodiments, the composition of hydrolyzed collagen peptides comprises at least 50% by weight, such as at least 60% or 70% by weight, preferably at least 80% by weight, more preferably at least 85% or 90%, even more preferably at least 95%, 96% or 97% by weight hydrolyzed collagen peptides, based on the dry mass of the composition.

In the compositions of hydrolyzed collagen peptides disclosed herein, the hydrolyzed collagen peptides are type 1 hydrolyzed collagen peptides (hCol1) and/or type 2 hydrolyzed collagen peptides (hCol2). In embodiments, the hCol1 has a mean molecular weight between about 300 Da and about 7500 Da (e.g., between about 600 Da and about 6000 Da, between about 1000 Da and about 5000 Da, between about 1300 Da and about 4500 Da, between about 1600 and about 4000 Da, between about 1800 Da and about 3500 Da, between about 2000 and about 3000 Da) and/or the hCol2 has a mean molecular weight between about 300 Da and about 7500 Da (e.g., between about 600 Da and about 6000 Da, between about 1000 Da and about 5000 Da, between about 1300 Da and about 4500 Da, between about 1600 and about 4000 Da, between about 1800 Da and about 3500 Da, between about 2000 and about 3000 Da). In further embodiments, the hCol1 is produced by enzymatic hydrolysis of collagen from vertebrates, in particular porcine, bovine or fish, or from molluscae, in particular jellyfish and/or hCol2 is produced by enzymatic hydrolysis of collagen from vertebrates, in particular porcine, bovine or fish. In still further embodiments, the hCol1 is produced by enzymatic hydrolysis of collagen from porcine, bovine or fish skin or hide or bone, preferably skin or hide and/or hCol2 is produced by enzymatic hydrolysis of collagen from form porcine, bovine or fish cartilage. In certain embodiments, the composition of hydrolyzed collagen peptides is incorporated or formulated into a food or feed product, preferably a food or feed product for oral administration, a food or feed ingredient. In some embodiments, the food or feed product is a drink, preferably a drink for oral administration. Non-limiting examples of suitable drinks include fruit juice, a fruit drink, an artificially flavored drink, an artificially sweetened drink, a carbonated beverage, a sports drink, a liquid diary product, a shake, an alcoholic beverage, a caffeinated beverage, infant formula and so forth. In some embodiments, the food or feed product is a solid foodstuff or feedstuff. Suitable examples of a solid foodstuff include without limitation yoghurt, a food bar, a snack bar, and the like. In certain embodiments, the composition of hydrolyzed collagen peptides is formulated as a dietary supplement. The hydrolyzed collagen peptides can be present in the form, for example, of a powder, a granulate, a solution or a suspension or in the form of tablets, capsules, pills, dragees, caplets or sachets, syrups, elixirs, if appropriate, in combination with suitable additives or inactive ingredients as described elsewhere herein. The composition comprising hydrolyzed collagen peptides disclosed herein may be administered for at least 1 week, at least 2, 3, 4, 5, 6, 7, 8, 9, 10, 11, 12, 13, 14, 15 or 16 weeks. The composition may be administered daily, thrice weekly, twice weekly, or weekly. Preferably, the composition comprising hydrolyzed collagen peptides is administered daily for at least 1 week, preferably for at least 2 weeks.

The daily oral intake of the composition comprising hydrolyzed collagen peptides disclosed herein is preferably in the range from 0.5 g to 15 g of the composition, preferably from 1 g to 10 g, more preferably from 2 g to 10 g, even more preferably from 5 g to 10 g, and particularly preferably in the range from 6.0 g to 8.0 g such as about 7.5 g.

The following examples are meant to be illustrative of the practice of the invention, and not limiting in any way.

EXAMPLES

Bolus Delivery of hCol

Daily bolus delivery of hCol1 and hCol2 over the course of the 16 week experimental time line (FIG. 1C) was used to investigate joint protective effects of long term daily consumption of hCol1 and hCol2. To support the daily bolus delivery strategy, hCol1 and hCol2 were incorporated into Nutella such that a 150 mg amount of the experimental mixtures would support delivery of 3.8 mg (LD) or 38 mg (HD) of hCol1 or 3.8 mg (LD) hCol2. Once prepared, 150 mg aliquots of Control (Nutella vehicle alone), LD and HD hCol1 and LD hCol2 were deposited onto sterile ceramic tiles (FIG. 1A) and presented to each individually housed mouse at the same time in the morning daily (FIG. 1B). Mice typically consumed the entire supplement within 2 minutes, supporting bolus delivery. To confirm successful absorption of the hCol1 supplements into the circulation, blood samples were collected from mice 1 week before and 2, 3, and 12 weeks after surgery (sham or MLI, FIG. 1C). For the first two time points, the blood draw was collected 3 hours after consumption of the supplements, while the second two time points involved a blood draw 1 hour after consumption. As expected, serum levels of hProline were increased following delivery of the hCol1 supplements. When collected 3 hours after bolus delivery, only the HD hCol1 group displayed a significant increase in serum hProline levels (FIG. 1D).

Comparatively, when blood draws were collected 45 minutes after bolus delivery, both LD and HD groups displayed significant increases in serum hProline levels, with apparent dose dependency (FIG. 1E). These results confirm that the bolus delivery regimen was effective, with increased serum levels of hProline establishing increased absorption of hCol1 following both LD and HD hCol1 supplementation. Notably, similar analysis of samples from mice administered hCol2 confirmed effective oral delivery based on measured hydroxyproline levels in circulating serum (FIG. 12)

Impact of hCol1 Supplements on Cartilage Structure

Initial analysis of the knee joint articular cartilage involved automated histomorphometry to determine total cartilage area in sagittal sections stained with Toluidine Blue and Fast Green. Stained sections were digitized to images and an 'Articular Cartilage Application' was developed on the Visiopharm Platform to streamline the determination of total cartilage area on the femoral condyle and tibial plateau. The main cartilage changes played out on the tibial plateau, where there was significant total cartilage loss detectable at both 3 weeks (FIG. 2B) and 12 weeks (FIGS. 2A and 2C) post injury. No changes in femoral condyle articular cartilage area were detected at either 3 or 12 weeks after injury or in any of the experimental groups (data not shown). Suggesting possible chondroprotective effects of hCol1 supplementation, total tibial cartilage area loss 3 weeks after MLI was prevented in the LD hCol1 group, with the HD group trending toward improvement but missing significance (FIG. 2B). At the 12 weeks post-MLI time point, hCol1 was dose-dependently protective, with total tibial cartilage area loss mitigated significantly in the HD group, and the LD group trending toward significance (FIG. 2C). It should be noted that there were no discernable effects of hCol1 supplementation on baseline (Sham-operated) articular cartilage area (data not shown). Overall, these results provide the first indication that dietary supplementation with hCol1 could be protective in the development and progression of PTOA.

Figure 3B:
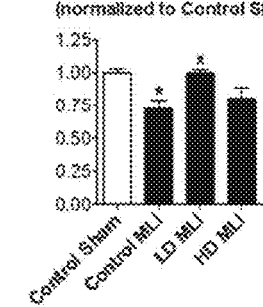
Figure 3C:
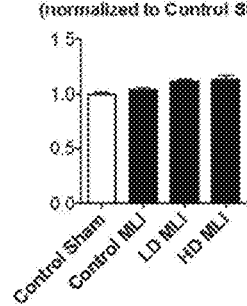
Figure 3D:
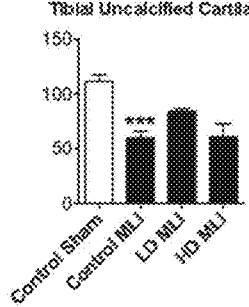
Figure 3E:
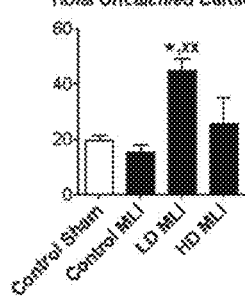
Figure 3F:
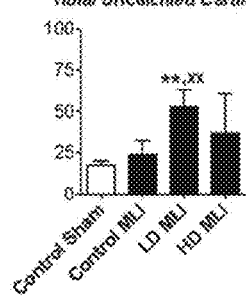
Figure 3G:
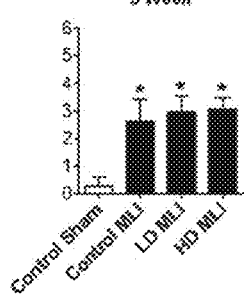

While the automated histomorphometry approach was useful in identifying protective effects of hCol1 in PTOA, the underlying changes in cartilage architecture and cellularity that contributed to the overall preservation of total tibial cartilage were not discernable using this method. Thus, additional analyses were performed on Safranin O/Fast Green- or Alcian Blue Hematoxylin/Orange G-stained sections using a manual histomorphometry approach (Osteomeasure system) as well as standardized OARSI cartilage scoring. At 3 weeks post-MLI, there were observable differences in cartilage architecture between experimental groups, including apparent preservation of tibial uncalcified cartilage and cellularity in this zone in mice supplemented with hCol1. Consistent with the automated analysis (FIG. 2B), reduction of tibial uncalcified cartilage area following MLI was mitigated significantly by hCol1 supplementation, with the LD group showing significant effects and the HD trending in that direction (FIG. 3B). Regarding calcified cartilage area (tide mark to osteochondral junction), MLI had no effect and neither did hCol1 supplementation (FIG. 3C). Loss of chondrocytes from the tibial uncalcified zone following MLI appeared to be reduced in LD and HD hCol1 fed animals (FIG. 3A), but this trend failed to achieve statistical significance (FIG. 3D). Suggesting that hCol1 supports chondrocyte proteoglycan matrix production at the 3 week time point post-MLI, the number and percentage of Safranin O-positive chondrocyte lacunae were significantly increased in LD hCol1-supplemented mice, with the HD group trending in that direction (FIGS. 3E and 3F). Finally, the impact of MLI on the joint cartilage 3 weeks post injury was significant based on OARSI scoring, but the generalized analysis of cartilage content using this scoring system was not sensitive enough to identify any improvement in the hCol1 supplemented groups (FIG. 3G). It should be noted that there were no significant differences between experimental groups in other structural analyses performed, including uncalcified and calcified cartilage area on the femoral condyles and the number of hypertrophic chondrocytes, and in any zone of the cartilage on the femoral condyles and tibial plateaus (data not shown). Also of note, the apparent inability of HD hCol1 to match the efficacy of LD hCol1 in preserving uncalcified cartilage and Safranin O-positive chondrocyte populations at 3 weeks post-MLI may be due to two outlier samples in the HD group that caused a large error (FIGS. 2B, 2E and 2F).

For the sake of comparison, FIG. 9 depicts similar analyses for mice that were administered hCol2. Like hCol1, a chondroprotective effect was observed 3 weeks post-MLI in mice that were supplemented with hCol2 (FIG. 9A-9E). These hCol2 effects were at the LD hCol2, and notably were equally potent compared to effects elicited by HD hCol1, suggesting the hCol2 elicits a more potent chondroprotective effect.

Figure 4A:
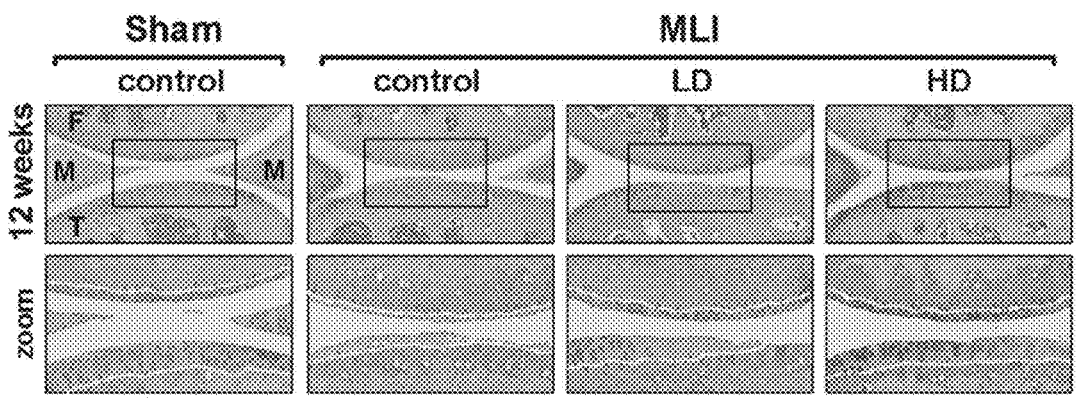
FIGS. 4A-4G: hCol1 protects against cartilage loss in mid to late stage murine PTOA. Panel (FIG. 4A) presents an array of representative 40× Safranin O/Fast Green stained sagittal sections from the medial compartment of sham and MLI joints 12 weeks post-injury under various treatment conditions (control=vehicle, LD=3.8 mg hCol1/day, HD=38 mg hCol1/day). Joint structures are labeled (F=femur, M=meniscus, T=tibia) and the tidemarks are denoted with a dashed line in the zoomed images. Black scale bars depict 100 μm. Cartilage architecture was evaluated using the Osteomeasure System to determine the tibial uncalcified cartilage area (FIG. 4B), the tibial calcified cartilage (FIG. 4C), the number of chondrocytes in the tibial uncalcified cartilage (FIG. 4D), and the number (FIG. 4E) and percentage (FIG. 4F) of Safranin-O positive (SafO$^+$) chondrocytes in the tibial uncalcified cartilage. OARSI scoring of the sections analyzed by histomorphometry was also performed (FIG. 4G). Significant differences between experimental groups in the histomorphometry data (B-F) were identified via one-way ANOVA with a Tukey's multiple comparisons post-test (*$p<0.05$, $p<0.01$, *$p<0.001$ compared to Control Sham; $^x p<0.05$, $^{xx}p<0.01$ compared to Control MLI, N=6). Significant differences between experimental groups in the OARSI data (FIG. 4G) were identified via a Kruskal-Wallis Test with a Dunn's multiple comparisons post-test (*$p<0.05$, **$p<0.01$ compared to Control Sham, N=6).
Figure 4B:
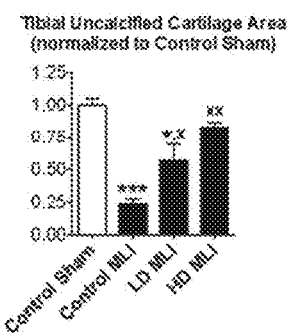
Figure 4C:
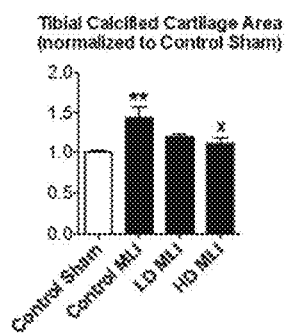
Figure 4D:
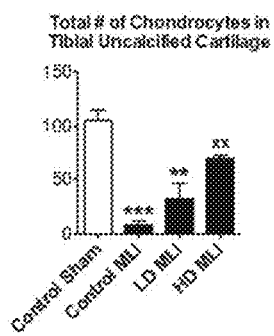
Figure 4E:
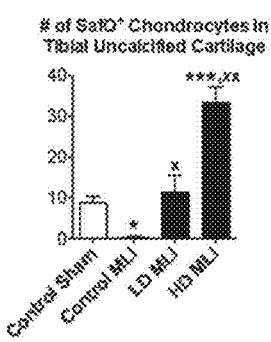
Figure 4F:
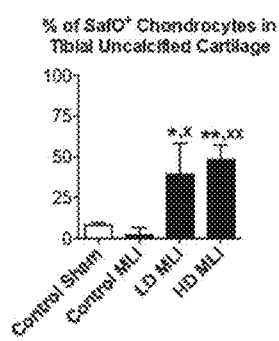
Figure 4G:
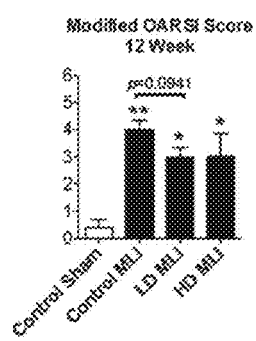

A similar set of manual histomorphometric analyses were performed in Safranin O/Fast Green-stained sagittal joint sections harvested 12 weeks post-MLI. At this time point, hCol1 appeared to provide more significant protection than at 3 weeks, with representative sections depicting apparent preservation of articular cartilage area and cellularity (FIG. 4A). Use of Osteomeasure again facilitated quantification of key cartilage structural elements, with clear hCol1 dose-dependent preservation of uncalcified tibial cartilage following MLI (FIG. 4B). Complimenting this effect was a protection against MLI-induced expansion of the tibial calcified cartilage zone, with joints from HD hCol1-treated mice showing a significant reduction in calcified cartilage area (FIG. 4C). Regarding cellularity, MLI-induced nearly complete loss of chondrocytes in the uncalcified tibial cartilage by 12 weeks, with hCol1 dose dependently protecting against this effect (FIG. 4D). Remarkably, chondrocyte number in the HD hCol1 group was not significantly different from sham operated control group, indicating substantial efficacy of the supplement in preserving cartilage cellularity. Regarding the number and percentage of Safranin O-positive chondrocyte lacunae in the tibial uncalcified cartilage, the nearly complete loss of cells producing proteoglycan matrix 12 weeks post-MLI was fully rescued in mice supplemented with hCol1 (FIGS. 4E and 4F). In fact, suggestive of a chondroregenerative effect, both LD and HD hCol1 groups displayed both a greater number and greater percentage of Safranin O-stained lacunae in tibia uncalcified cartilage compared to Control Sham joints (FIGS. 4E and 4F). While, as expected, the OARSI score was significantly increased 12 weeks post-MLI, hCol1 supplemented mice only showed modest improvement of the score, with the LD group trending toward significance (FIG. 4G). As discussed for analytics performed on joints at the 3 week time point, it should be noted that there were no significant differences between experimental groups in uncalcified and calcified cartilage area on the femoral condyles, and in the number of hypertrophic chondrocytes in any zone of the cartilage on the femoral condyles and tibial plateaus (data not shown).

PTOA-Induced Upregulation of MMP13 is Ameliorated by hCol1

An important step in cartilage degeneration is the aberrant transition of articular chondrocytes into the hypertrophic state, an event marked by the expression of catabolic enzymes such as MMP13, and the marker of terminal hypertrophy, Type 10 Collagen (ColX). Accordingly, it is possible that the chondroprotective action of hCol1 documented in FIG. 2-4 is associated with an inhibition of chondrocyte hypertrophy. To address this question, immunohistochemistry was performed to evaluate MMP13 and ColX protein levels in the articular cartilage. As expected, and indicative of chondrocyte hypertrophy, Control MLI mice had elevated levels of both MMP13 and ColX in the uncalcified cartilage compared to Control Sham mice at the 3 week time point (FIGS. 5A and 5B). Mice supplemented with HD hCol1 were protected from the MLI induced MMP13 staining in the uncalcified cartilage, suggesting that preservation of cartilage architecture in this group could in part be due to inhibion of matrix degeneration (FIG. 5A). In contrast, ColX staining was not reduced in MLI mice supplemented with hCol1, indicating that hCol1 did not impact terminal chondrocyte hypertrophy (FIG. 5B). Overall, no differences were observed in the calcified cartilage, as chondrocytes in this zone were all actively producing similar levels of both MMP13 and ColX (FIGS. 5A and 5B). It should be noted that at the 12 week time point, MLI joints from control-supplemented mice had lost most of the uncalcified cartilage and associated chondrocytes, making comparisons with the treated groups uninformative (data not shown). Together, these data suggest that mice supplemented with the HD hCol1 may have been protected from cartilage degeneration in part due to reduced MMP13 production by chondrocytes residing in the uncalcified cartilage.

Impact of hCol1 Supplements on Articular Chondrocyte Life Cycle

The remarkable ability of hCol1 supplementation to protect against chondrocyte loss in murine PTOA (FIG. 4D) could be a key driver of its chondroprotective effect by setting the stage for persisting chondrocytes to produce matrix molecules (FIGS. 4E and 4F). To determine if the protection against MLI-induced chondrocyte loss was due to stimulation of proliferation or inhibition of apoptosis, representative tissue sections were analyzed via PCNA and TUNEL staining. While there was no detectable difference in the number of proliferative chondrocytes between experimental groups at 3 weeks post-MLI based on PCNA immunodetection (data not shown), MLI-induction of broad chondrocyte apoptosis was reduced 3 weeks post-MLI in mice supplemented with hCol1 (FIG. 6). Representative TUNEL-stained sections showed a marked reduction in the number of apoptotic chondrocytes in superficial-to-middle layer cartilage zones (zoom panels in FIG. 6). It should be noted that analysis was not informative at the 12 week time point because MLI joints in the control-supplemented mice were TUNEL-negative due to broad apoptotic loss of chondrocytes that had occurred prior to the harvest. Overall, these data suggest that the significantly larger number of chondrocytes seen in the uncalcified cartilage of hCol1 supplemented mice at 12 weeks post-MLI (FIG. 4D) could be due to protection from apoptosis earlier in the disease process.

Oral Delivery of hCol1 Protects Against PTOA-Induced Synovial Change

The marked preservation of matrix-producing chondrocytes post-MLI in hCol1 supplemented mice begged for subsequent investigation of the impact of hCol1 on inflammatory synovial changes that are known to contribute to chondrocyte death following joint injury. (Goldring et al. 2011 *Curr Opin Rheumatol.* 23(5):471-8; Goldring et al. 2011 *European cells & materials* 21:202-20.)

Figure 7B:
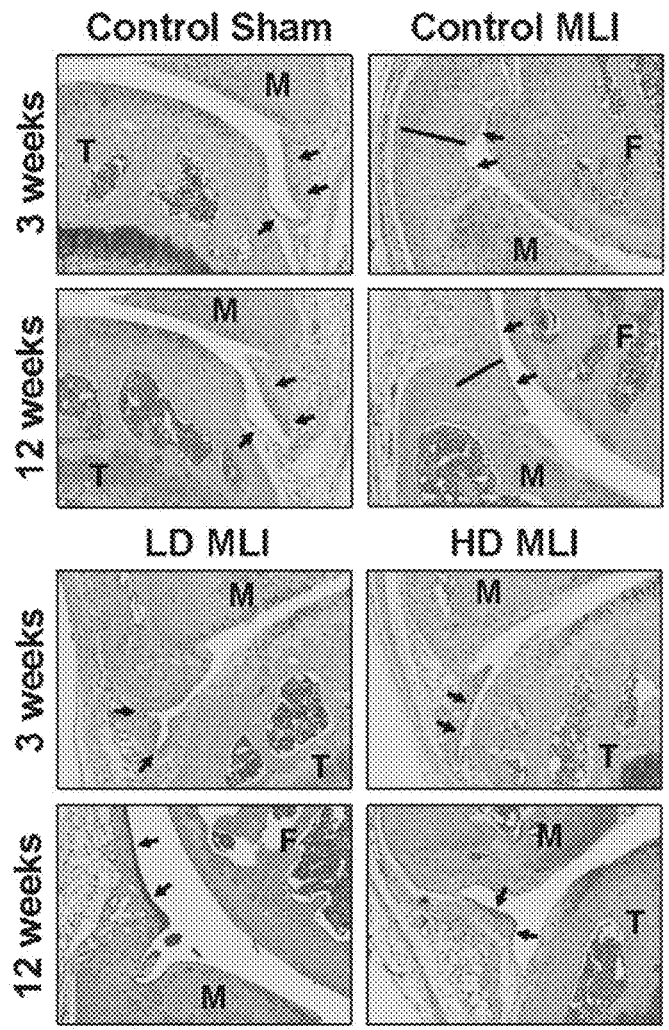
Figure 7C:
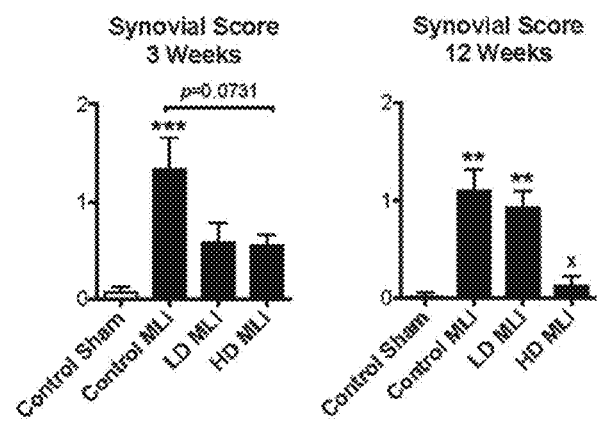
Figure 9A:
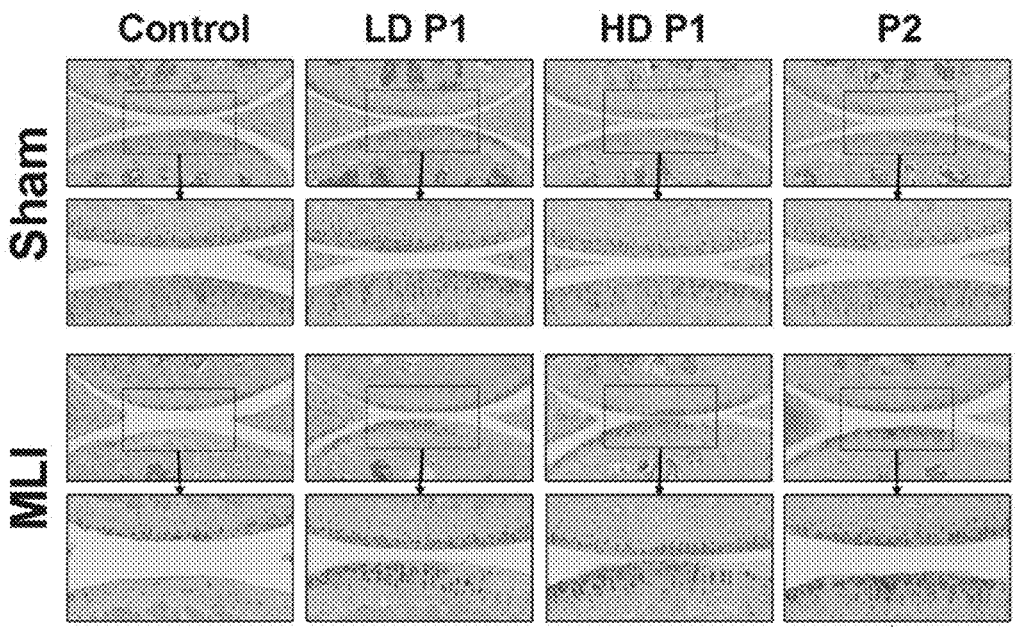
FIGS. 9A-9E: Like hCol1, hCol2 demonstrates robust chondroprotection 3 weeks post-MLI. Safranin O/Fast Green staining of knee joints 3 weeks after MLI reveals enhanced pericellular proteoglycan content in hCol-treated groups (FIG. 9A). Manual evaluation of cartilage tissue parameters via histomorphometry revealed no significant effects of hCol1 (P1) and hCol2 (P2) treatments on tibial uncalcified cartilage area or total cell (chondrocyte) counts in the uncalcified cartilage in Sham or injured joints (FIG. 9B and FIG. 9C). However, hCol1 and hCol2-fed groups showed an increased number (FIG. 9D) and percentage (FIG. 9E) of SafO+ cells, indicating increased proteoglycan production. (x,*=p<0.05, 2 way ANOVA with Bonferroni-Dunn multiple comparison, N=6; x denotes differences between sham and MLI within each experimental group).
Figure 9B:
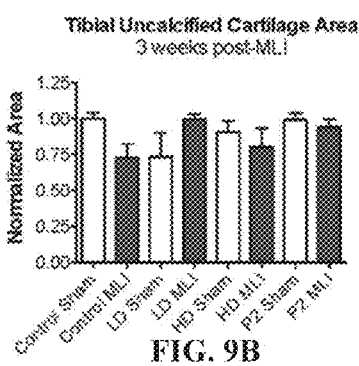
Figure 9C:
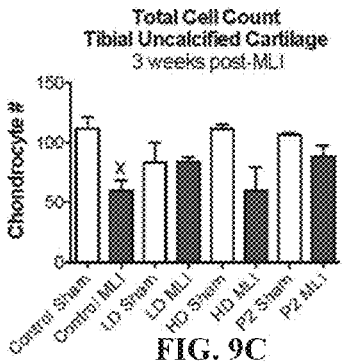
Figure 9D:
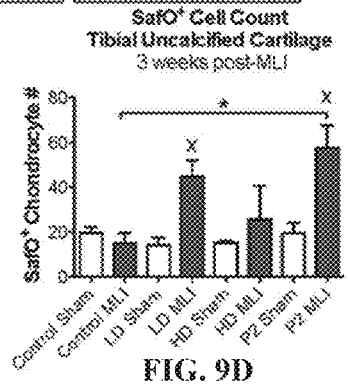
Figure 9E:
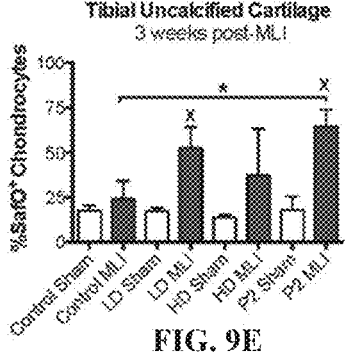
Figure 10A:
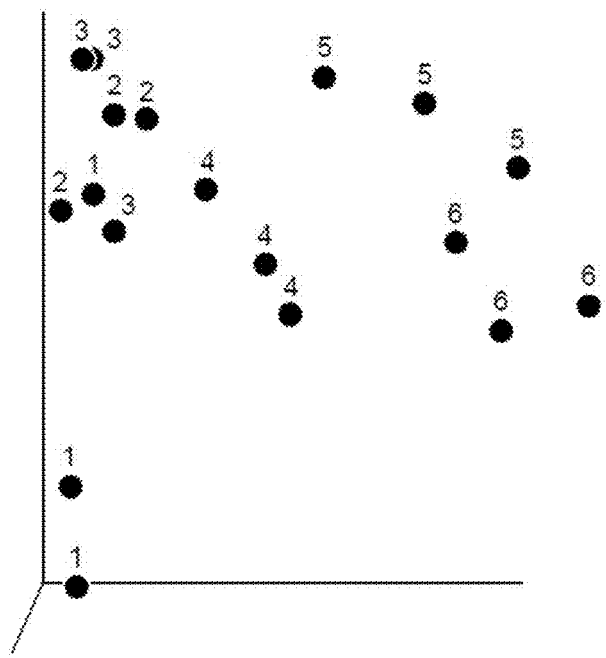
FIGS. 10A-10C: hCol1 supplementation induces significant change in the gut microbiome. Microbial rDNA analysis was performed on fecal samples collected from lean and obese mice supplemented with control Nutella, 38 mg/day hCol1, or glucosamine. Of note, PCoA plots reveal a significant effect of hCol1 on microbial diversity in lean mice (FIG. 10A-10C), characterized by a significant increase in the abundance of Tenericutes (FIGS. 10B and 10C).
Figure 10B:
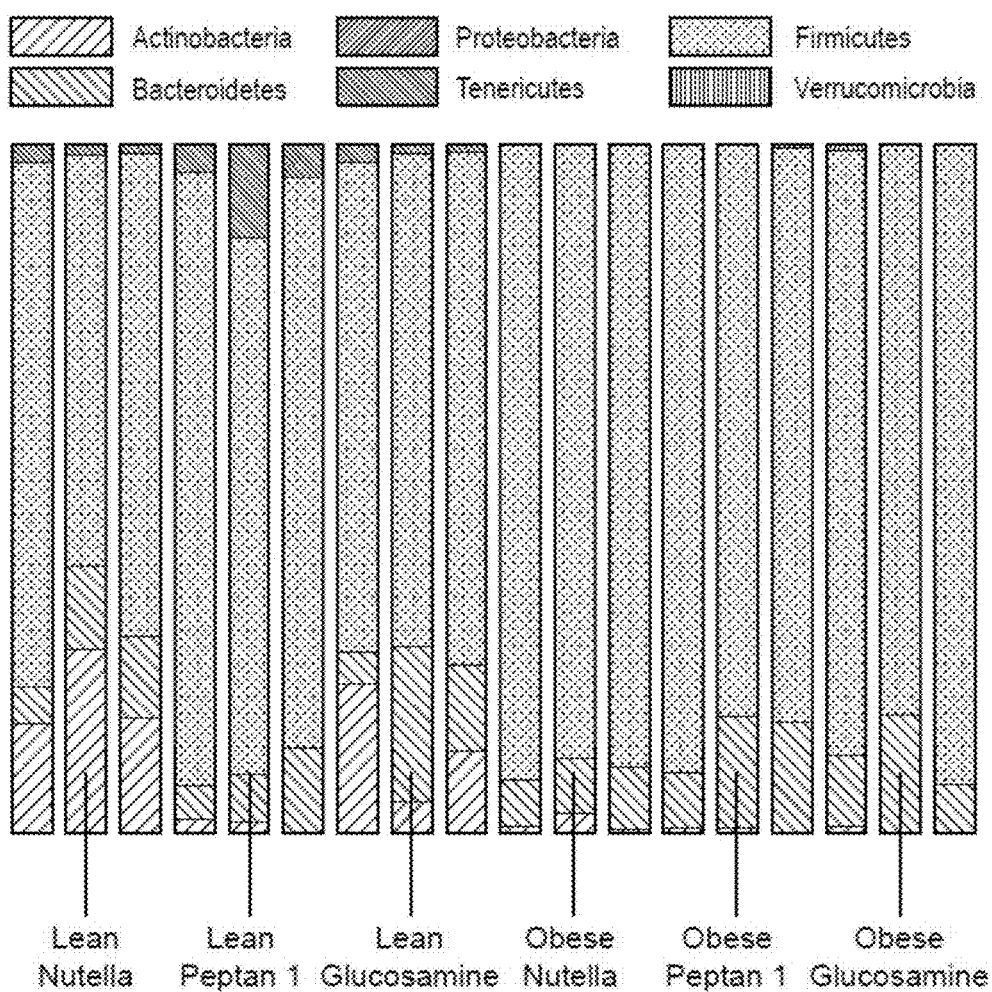
Figure 10C:
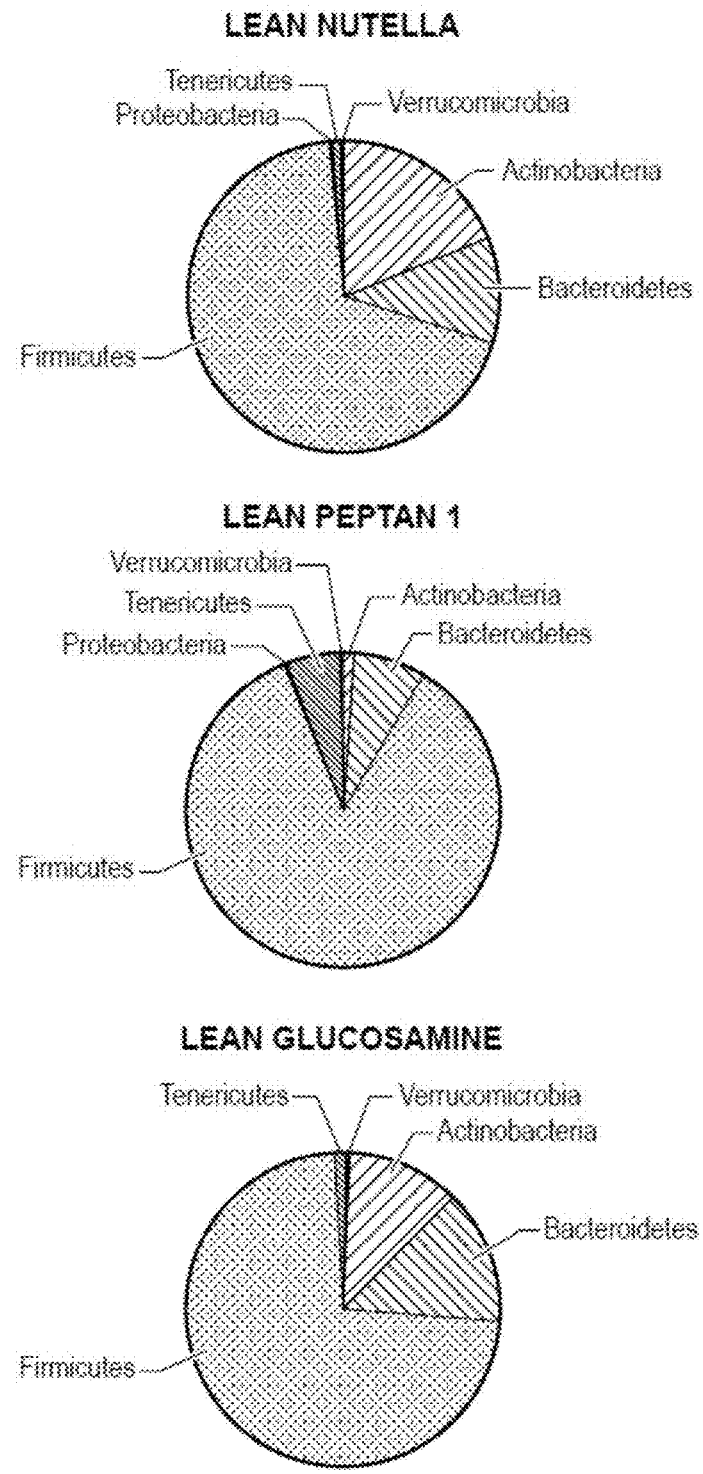
Figure 10C:
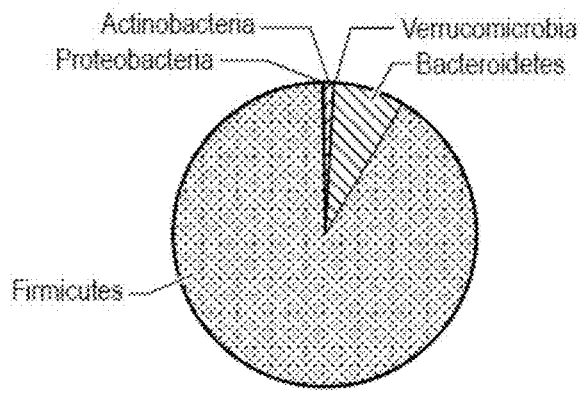
Figure 10C:
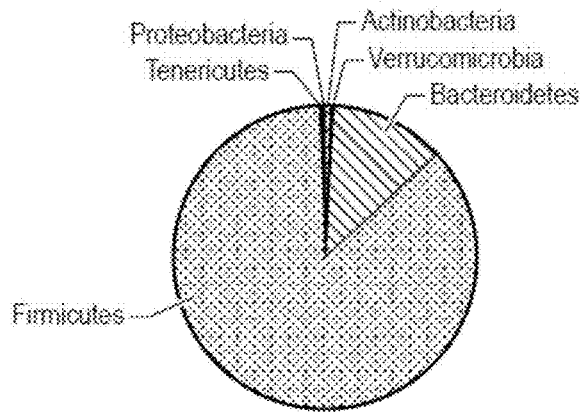
Figure 10C:
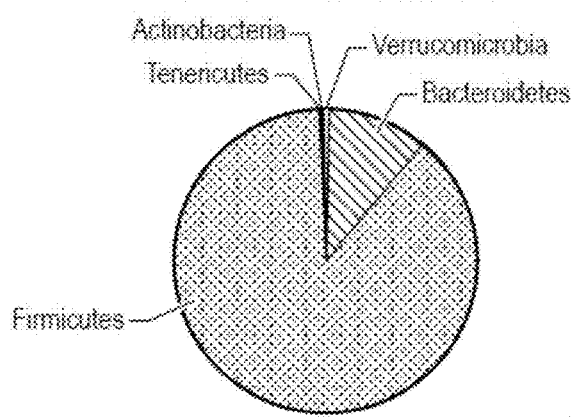

Comparison of representative Safranin O/Fast Green stained sagittal knee joint sections revealed an apparent reduction in the severity of synovial hyperplasia in mice provided the hCol1 supplements. At both 3 and 12 weeks post-MLI, synovial thickness was increased compared to Control Sham joints, while mice provided hCol1 were protected from MLI-induced hyperplastic synovial change (FIG. 7A). Synovial phenotypes were further investigated using a synovial scoring method, revealing significant effects in mice provided hCol1 supplements that were consistent with the representative histology. As expected, MLI induced a significant increase in synovial score (i.e., more robust synovial hyperplasia) at both 3 weeks (FIG. 7B) and 12 weeks (FIG. 7C) post-MLI. At 3 weeks, synovial scores trended toward a reduction (improvement) in the MLI groups that were supplemented with hCol1 (FIG. 7B). Comparatively, at 12 weeks post-MLI, the synovium in mice from the HD hCol1 group was significantly less hyperplastic, suggesting that hCol1 supplements effectively reduced synovial/joint inflammation that is present in PTOA.

Among several cytokines implicated in diarthrodial joint degeneration, TNF is established as a central inflammatory mediator that is present in synovial fluid and upregulated in hyperplastic synovium in PTOA, particularly in the early post-trauma time frame. (Goldring M B, *Potential Mechanisms of PTOA: Inflammation,* In: Olson et al., editors. Post-Traumatic Arthritis: Pathogenesis, Diagnosis and Treatment, New York: Springer; 2015, p. 201-8; Golightly et al., *Biomarkers of PTA,* In: Olson et al., editors. Post-Traumatic Arthritis: Pathogenesis, Diagnosis and Management, New York: Springer; 2015, p. 317-30.)

To investigate the impact of hCol1 supplementation on TNF expression post-MLI, both immunohistochemical staining and mRNA analysis of synovial membranes were performed. Representative immunostained sagittal sections revealed increased TNF expression at both 3 and 12 weeks post-MLI, with mice from the HD hCol1 cohort substantially protected from this effect (FIG. 8A). This was confirmed via quantitative analysis of Tnf mRNA levels in synovial membranes harvested from the various experimental groups. Specifically, 3 weeks post-injury, both LD and HD hCol1 supplementation significantly reduced Tnf levels in synovium from both the sham and MLI cohorts (FIG. 8B). While the overall synovial level of Tnf was lower 12 weeks post-injury, hCol1 still effectively reduced synovial Tnf in MLI joints, with the HD group achieving statistical significance (FIG. 8C). It should be noted that while the synovial expression of other genes, including Il1β, Prg4 and Mmp13, was increased following injury, particularly at 12 weeks post-MLI, hCol1 supplementation did not have a significant impact on expression level (data not shown). Overall, these findings suggest that dietary supplementation with hCol1 reduces synovial hyperplasia and mitigates synovial Tnf expression in both early and mid-stage PTOA.

Protocol for Delivery of hCol1 Supports Changes in Gut Microbiome of Mice

Figure 11A:
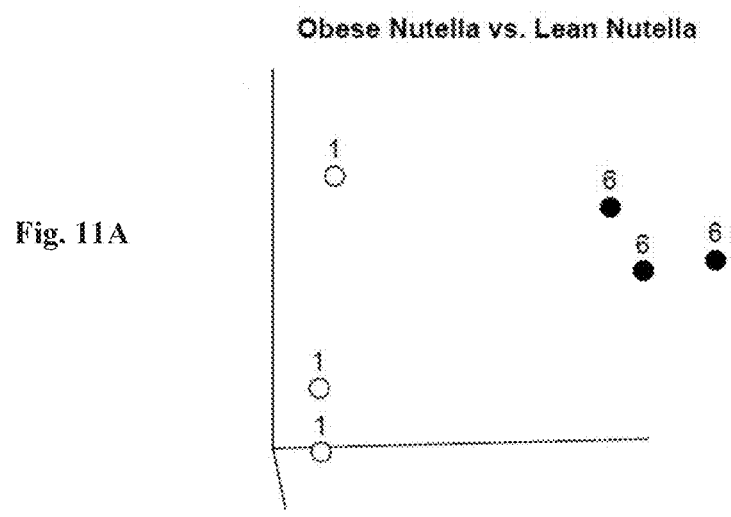
FIGS. 11A-11E: hCol1 and glucosamine elicit different effects on the gut microbiome. Principal coordinate analysis of microbial abundance from lean and obese mice supplemented with control Nutella, 38 mg/day hCol1, or glucosamine. 1: obese control Nutella, 2: obese glucosamine, 3: obese Peptan 1, 4: lean Peptan 1, 5: lean glucosamine, 6: lean control Nutella. Comparisons between groups show distinct differential effects of each treatment on microbial compositions: obese Nutella vs. lean Nutella (FIG. 11A); lean glucosamine vs. lean Nutella (FIG. 11B); lean Peptan 1 vs. lean Nutella (FIG. 11C); obese glucosamine vs. obese Nutella (FIG. 11D); and obese Peptan 1 vs. obese Nutella (FIG. 11E).
Figure 11B:
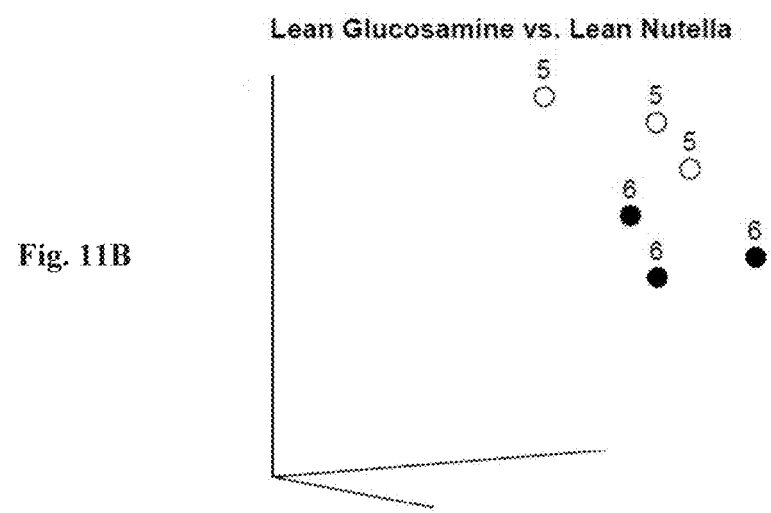
Figure 11C:
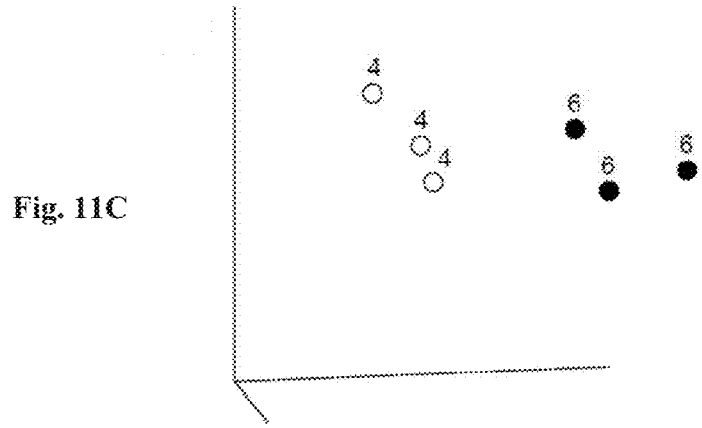
Figure 11D:
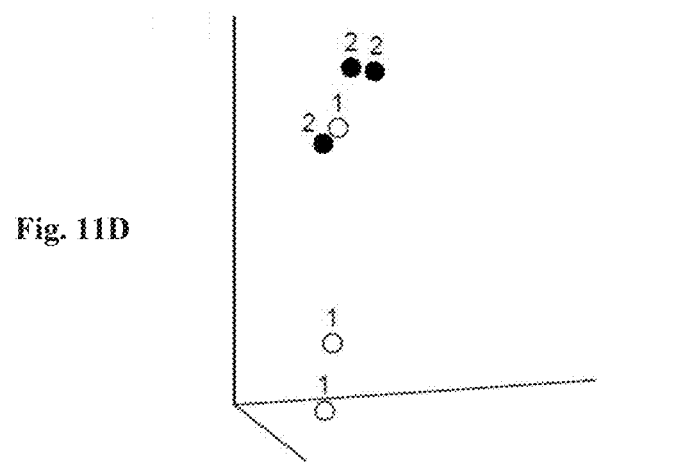
Figure 11E:
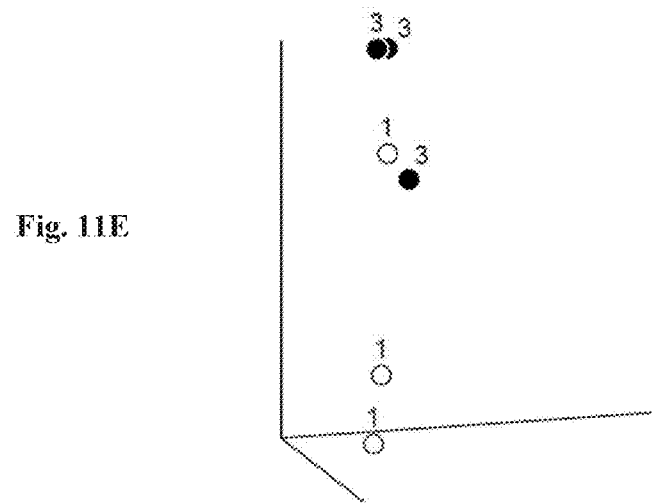

The data presented thus far substantiate the ability of hCol1 to provide robust chondroprotection in OA and additional beneficial effects in bone and skin. Now it is claimed that these effects are associated with seminal changes in the gut microbiome. Supporting this idea, rDNA sequencing analysis of DNA extracted from feces of mice provided hCol1 revealed microbial population changes in the of the lumen of the intestines, with microbes from the phylum Tenericutes showing a significant increase in abundance. In FIG. 10A and FIG. 11A-11E, Principal Coordinate Analyses (PCoA) are shown that were based on data collected from various groups of mice provided several different dietary supplements, one of which was hCol1 at the dosage used to study chondroprotection in FIGS. 1-9. The PCoA plot in FIG. 11A particularly shows that obese and lean Nutella-fed mice are completely different from each other, with a robust difference in microbial diversity between the groups. In FIGS. 11E and 11C, hCol1 fed lean mice were distinct from the controls suggesting that the hCol1 supplement is shifting the microbiome. The relative abundance plot in FIG. 10B and percentage breakdown in FIG. 10C reveal that the Lean Nutella group has more Actinobacteria (19.6127%) compared to the Lean hCol1 (1.2523%) and Lean Glucosamine (12.7091%) groups. A key observation, seminal to the described technology in this application, is that lean mice harbor a small population of Tenericutes (less than 0.8% on average), but this population is significantly increased in mice supplemented with hCol1 (6.998%). This hCol1 induction of Tenericutes represents the basis for suggesting that the Tenericute population is associated with the biological effects of hCol1 peptides on joint, skin and bone.

Figures 13A, 13B:
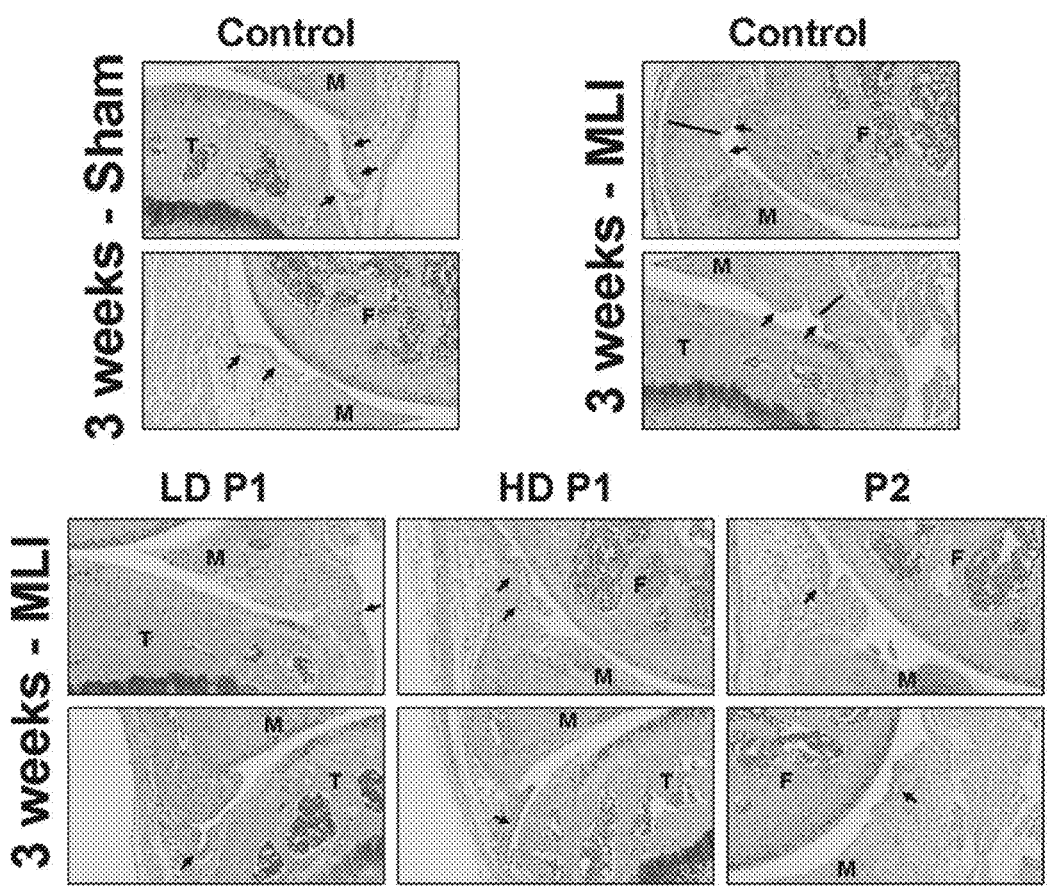
FIGS. 13A-13B: Synovial hyperplasia is also reduced in mice supplemented with hCol2.
Figure 15A:
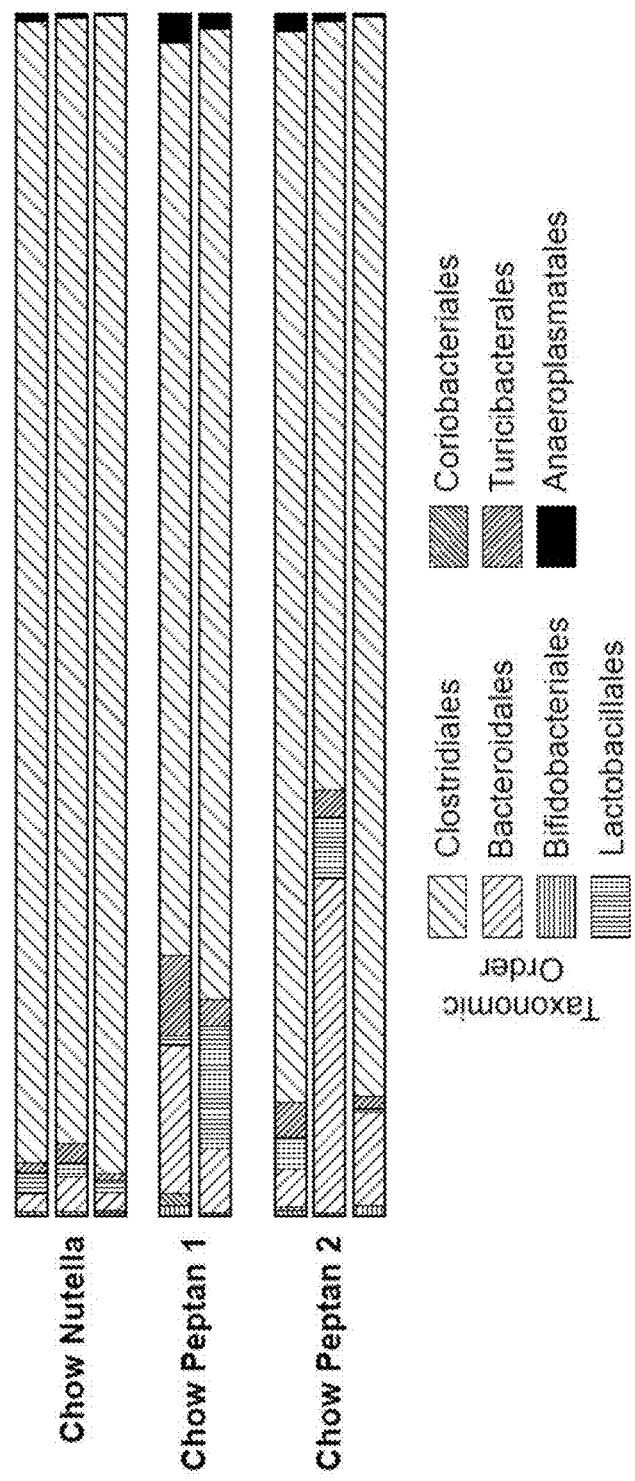
FIGS. 15A-15G: hCol1 and hCol2 supplementation induces significant change in the gut microbiome and provides protective effects in post-traumatic osteoarthritis.
Figure 15B:
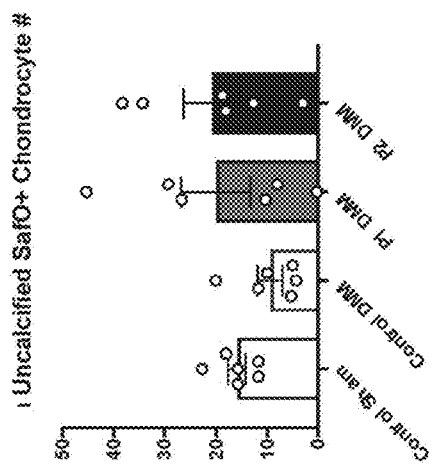
Figure 15C:
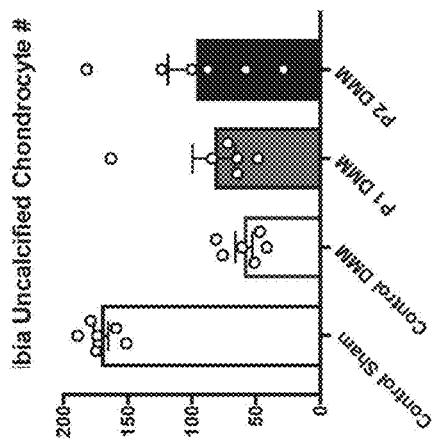
Figure 15D:
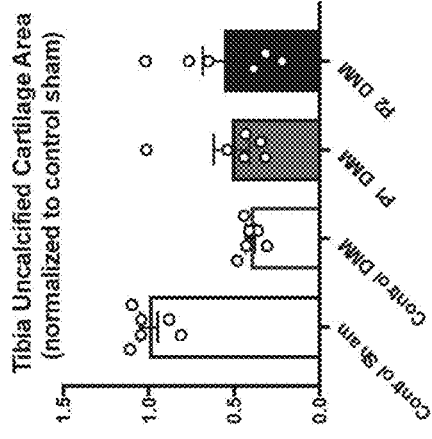
Figure 15E:
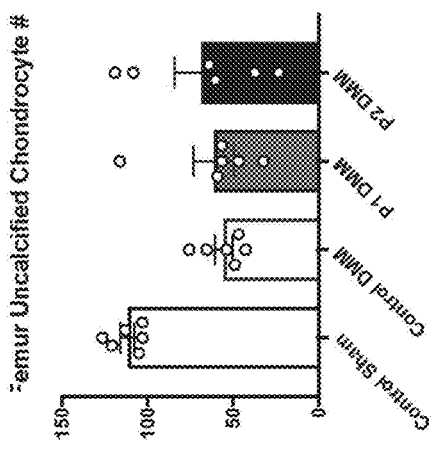
Figure 15F:
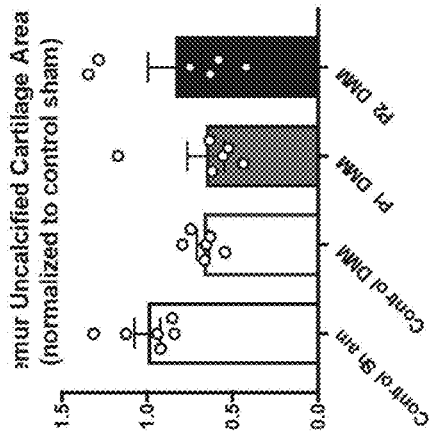
Figure 15G:
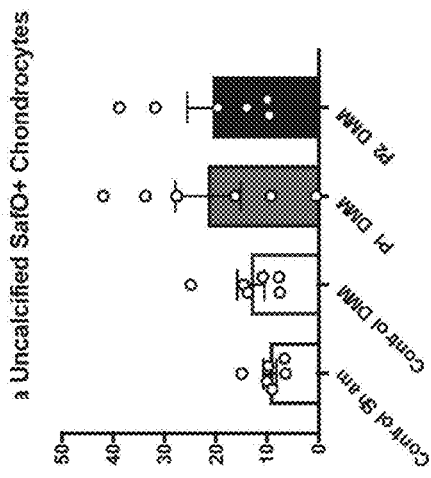
Figure 16A:
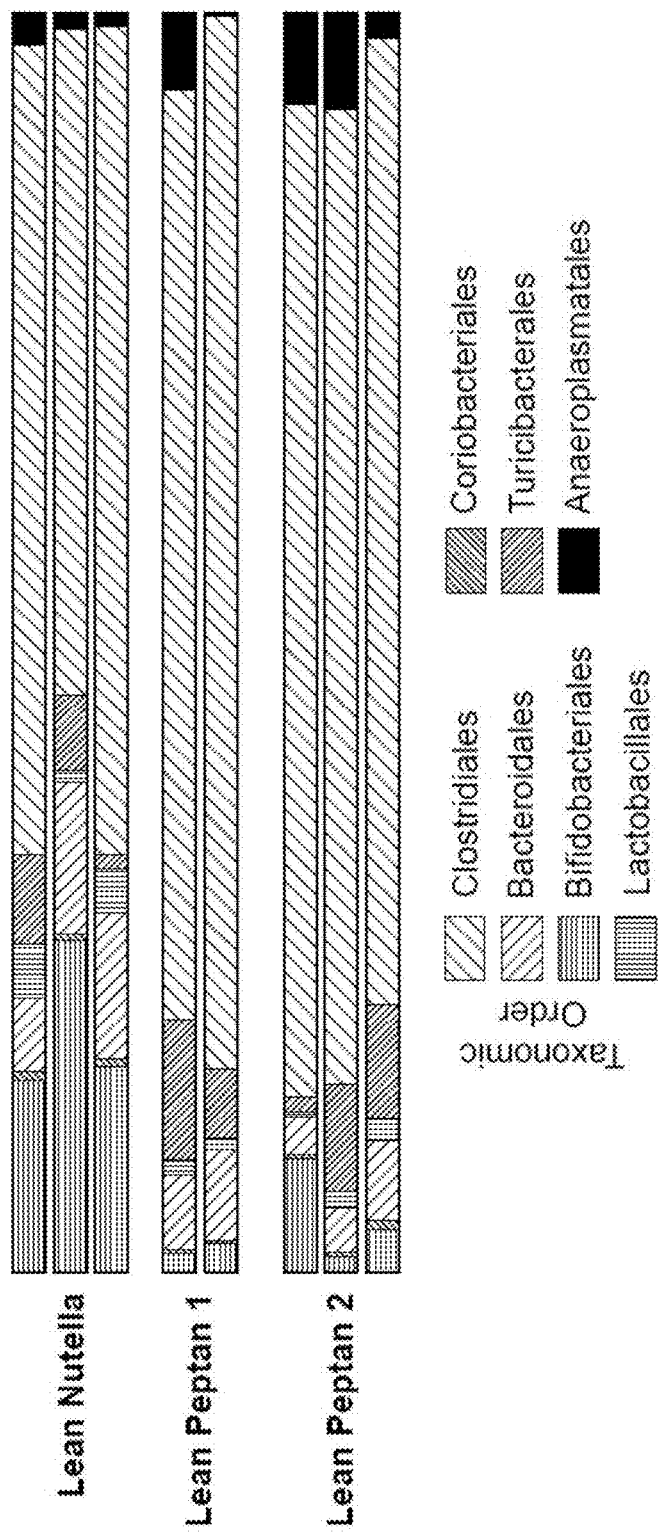
FIGS. 16A-16E.
Figure 16D:
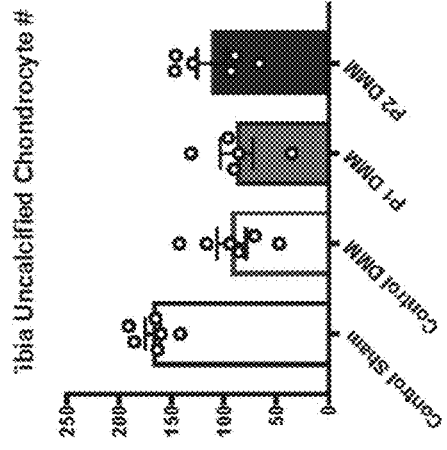
Figure 16C:
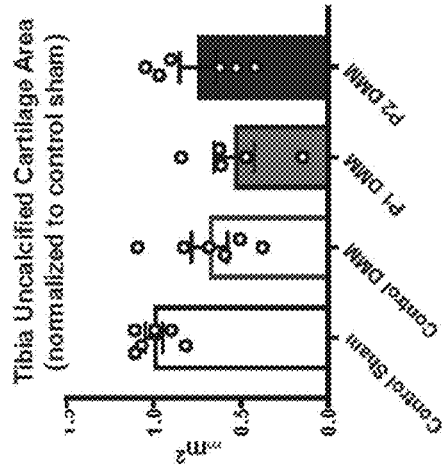
Figure 16B:
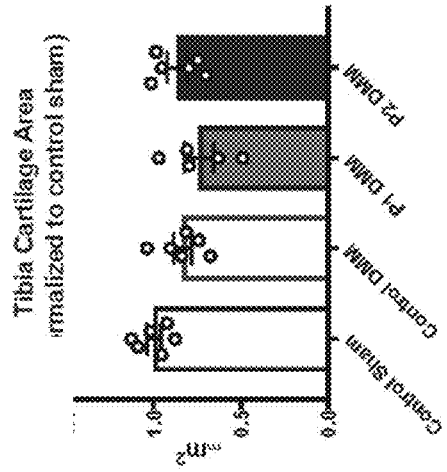
Figure 16E:
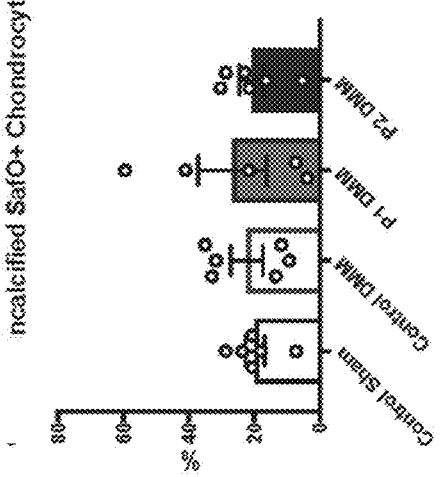
Figure 17A:
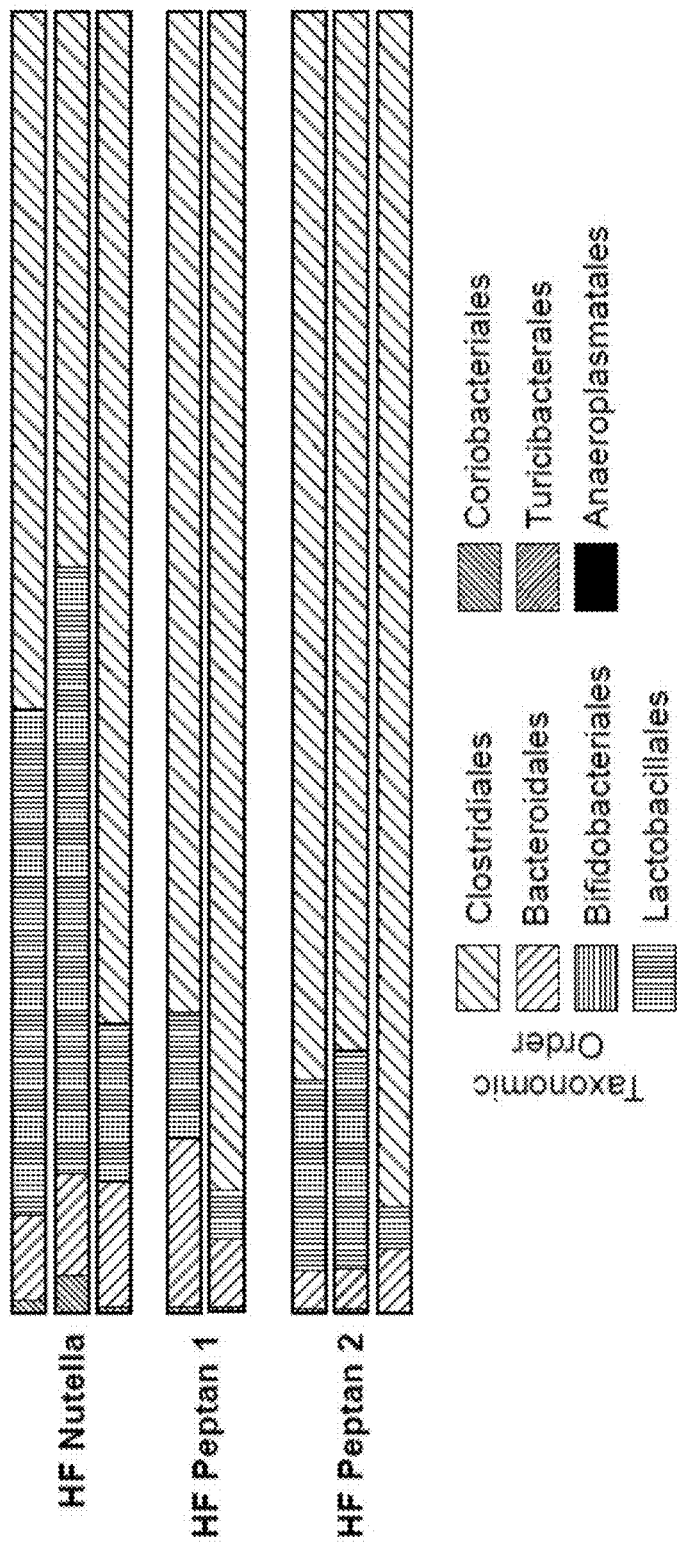
Figure 17F:
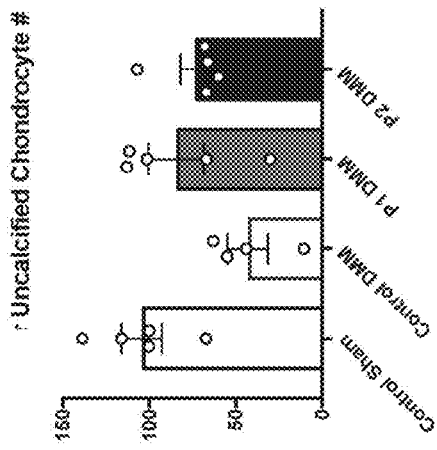
Figure 17E:
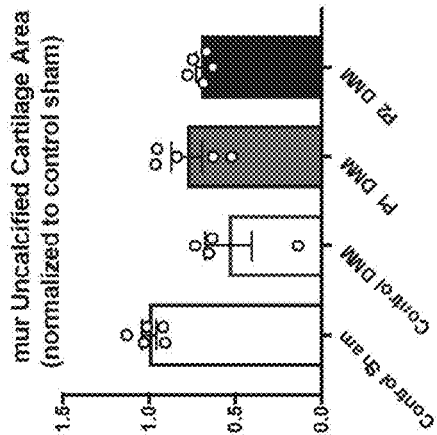
Figure 17H:
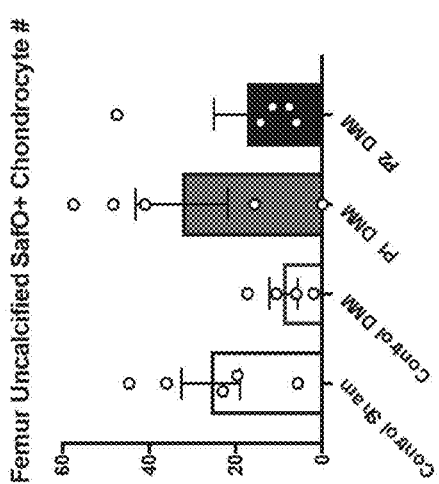
Figure 17G:
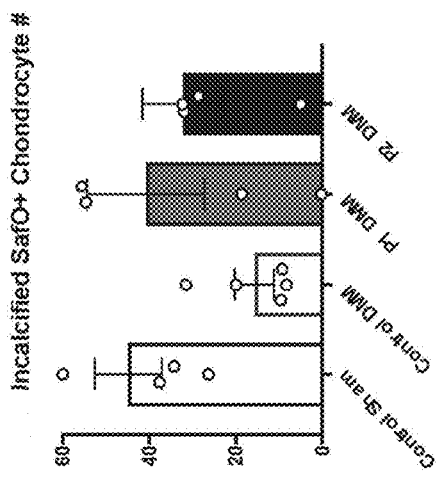
Figure 18:
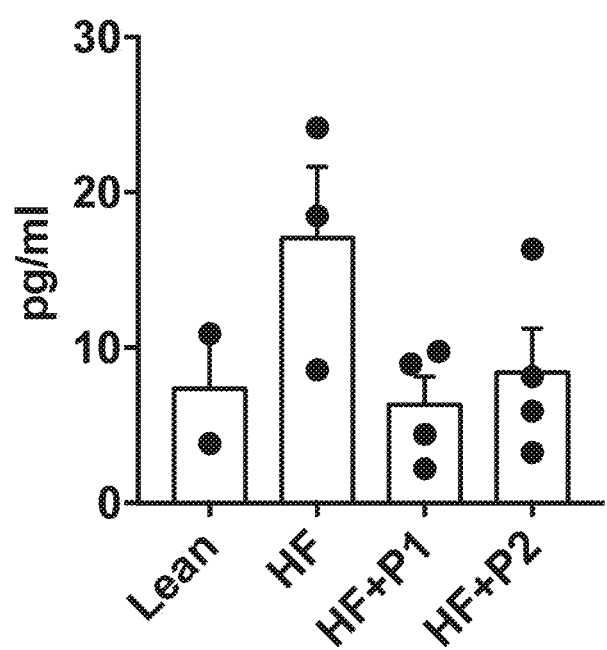
FIG. 18: Obesity-related increases in serum TNF-alpha are corrected by hCol1 and hCol2. Mice fed high fat (HF) diet for 3 months were supplemented daily with hCol1 (HF+P1), hCol2 (HF+P2) or vehicle (Nutella) (HF) for 12 weeks. A group of mice were fed the lean diet as a control. Serum was collected from all mice and an ELISA assay was performed to quantify levels of circulating TNF-alpha. The measured serum TNF-alpha levels in the indicated mice groups are shown.

Complimenting these findings, similar experiments were performed to document the ability of hCol2 to influence joint cartilage architecture and impact the gut microbiome. Confirming valid delivery of daily bolus doses of hCol2, mice fed this supplement displayed a spike in circulating hydroxyproline that paralleled the effect seen with hCol1 supplementation (FIG. 12). This was associated with chondroprotection in posttraumatic OA, including an increase in number of Safranin O-positive chondrocytes in the uncalcified cartilage layer 3 weeks after injury induction of disease (FIG. 9). This was correlated with a reduction in synovial hyperplasia in the hCol2-supplemented mice that was similar to the effect seen in hCol1-supplemented animals at the same 3 week time point (FIG. 13). Associated with this reduction in synovial thickening was mitigation of TNF expression in the synovium based on immunohistochemistry and reduction in the transcript for Tnf based on qPCR analysis of joint capsule tissue (FIG. 14).

Figure 21:
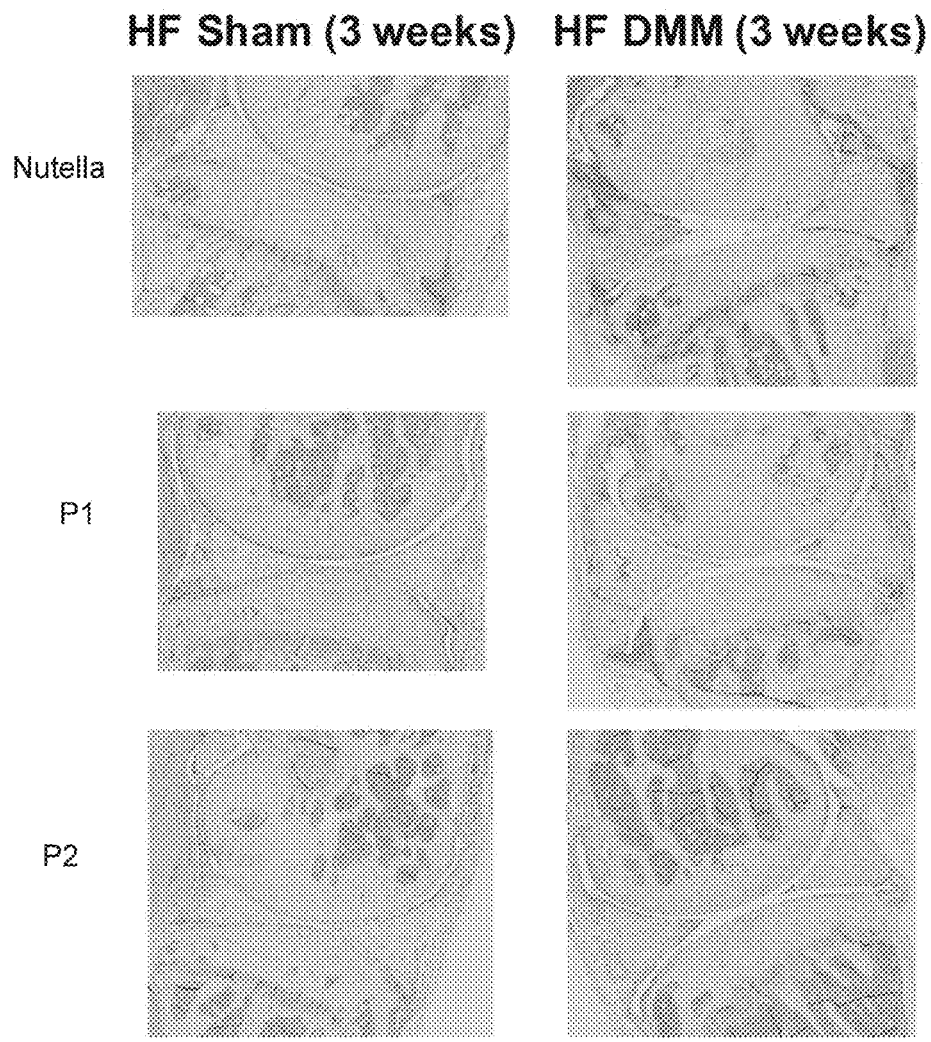
FIG. 21: hCol1 and hCol2 supplementation is associated with reduced synovial TNF expression in obese mice following traumatic injury. Mice were provided ad lib access to high fat diet for 3 months. Mice were continued on the diet after this period, but were supplemented daily with hCol1 (P1), hCol2 (P2) or vehicle (Nutella). After 1 week of supplementation, a surgical injury to the meniscus (DMM) was made, or an incision to the contralateral limb (Sham control), and knee joint tissues were harvested three weeks later. Representative images of TNF immunohistochemistry on the Sham and DMM joint tissues are shown.

Additional experiments were performed that aimed at quantifying cartilage preservation and synovial TNF expression in injured mice that were fed chow, lean or high fat diets. There were clear trends suggesting preservation of cartilage, chondrocyte number and chondrocyte production of matrix at 12 weeks post-injury in chow- and lean-fed mice and 3 weeks post-injury in high fat-fed mice (FIG. 15-17). TNF immunohistochemistry revealed a trend to reduced TNF expression in obese mice supplemented with either hCol1 or hCol2 at 3 weeks post-injury (FIG. 21). Furthermore, aligning with initial study of the gut microbiome in hCol1-fed mice shown in FIG. 10-11, supplementation of chow, lean and high-fat experimental diets with hCol1 or hCol2 had significant impact of the gut microbial community. In the chow diet, hCol 1 and 2 tended to have similar effects: Increases in the abundance of Bacteroidales, Bifidobacteriales, Lactobacillales, Turicibacterales, and Anaeroplasmatales. These increases were at the expense of the Clostridiales community in both hCol1 and hCol2 supplemented mice, but this effect was marginal, and Clostridiales was the dominant order all three groups (FIG. 15). In the lean diet, hCol 1 and 2 also tended to have a similar effect: Most striking was the loss of Bifidobacteriales and emergence of Anaeroplasmatales, and a minor decrease in Lactobacillales, Turicibacterales, and Anaeroplasmatales (FIG. 16). In the HF diet, hCol 1 and 2 again tended to induce the same effect: ablation of Coriobacteriales and reduction of Lactobacillales. Loss of the Lactobacillales community correlated with an increase in the abundance of the beneficial Clostridiales, which are known as butyrate producers (FIG. 17).

Overall, an increased microbial diversity was observed in the chow and HF diets supplemented with hCol1 and hCol2 (FIGS. 15, 17).

It was further observed in the HF diet, that hCol2 supplementation reduced the pro-inflammatory bacterial species *Peptococcaceae* rc4-4 sp., *Enterococcus* sp., *Lactobacillus* ND, *Erysipelotrichaceae* sp. and *Adlercreutzia* sp., and increased the anti-inflammatory bacterial species *Lachnospiraceae* sp., *Dehalobacterium* sp., *Mogibacteriaceae* sp., *Dorea* sp., *Clostridiales* ND, *Oscillospira* ND and *Bifidobacterium pseudolongum* (FIG. 19).

hCol 1 and 2 both had significant effects on the gut microbiome in each of the background diets tested, supporting their activity as prebiotic agents that could influence host biology through effects on the gut microbiome.

Anti-Inflammatory Effects of Oral Delivery of hCol1 or hCol2

Obesity-induced increases in circulating TNF-alpha were largely reversed upon hCol1 and hCol2 supplementation (FIG. 18), suggesting an anti-inflammatory effect that parallels the associated protection against osteoarthritis progression in this context and further supports the use of hCol1 and hCol2 as prebiotics.

Oral Delivery of hCol1 or hCol2 Improves Bone Health

Figure 20A:
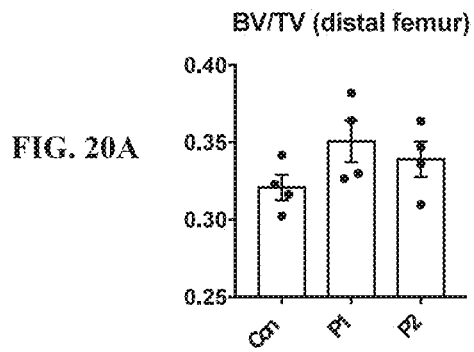
FIGS. 20A-20E: Effects of hCol1 and hCol2 on bone parameters. Non-obese, metabolically healthy mice were fed daily supplements of hCol1 (P1), hCol2 (P2) or vehicle (Nutella) (Con). After 12 weeks on supplement, MicroCT analysis was performed to examine femoral and vertebral bone parameters, and bone densitometry (DXA) was performed to determine whole body bone mineral density (BMD). Panels depict bone volume fraction (BV/TV, FIG. 20A), the density of trabecular connections (Conn-Density, FIG. 20B), and trabecular number (Tb.N., FIG. 20C) in distal femur, bone volume fraction (BV/TV) in the fourth lumbar vertebrae (L4) (FIG. 20D), and whole body bone mineral density (BMD) (FIG. 20E).
Figure 20B:
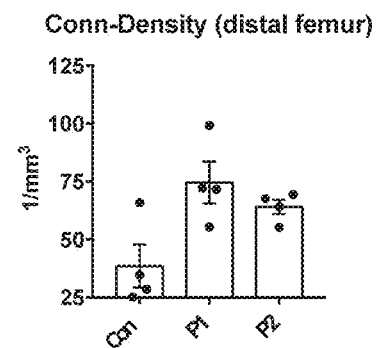
Figure 20C:
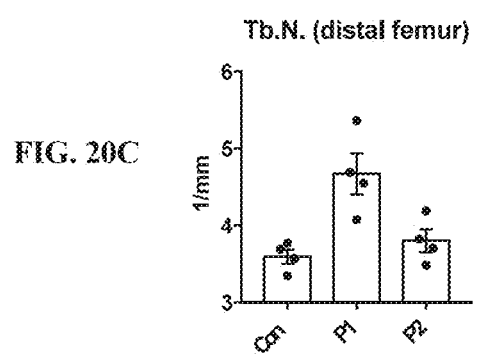
Figure 20D:
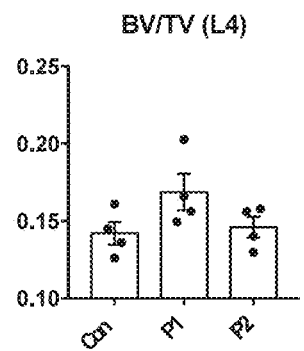
Figure 20E:
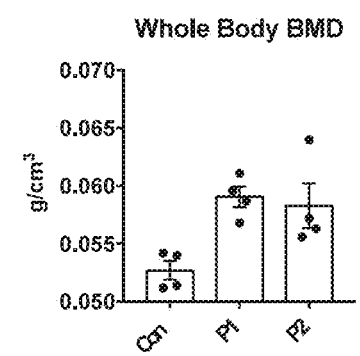

Non-obese, metabolically healthy mice were fed daily supplements of hCol1, hCol2 or vehicle control (Nutella). After 12 weeks on supplement, MicroCT analysis was performed to examine femoral and vertebral bone parameters, and bone densitometry (DEXA) was performed to determine whole body bone mineral density (BMD). hCol1 and hCol2 supplementation increased bone volume fraction (BV/TV), the density of trabecular connections (Conn-Density), and trabecular number (Tb.N.) (FIG. 20A-C). In addition, the bone volume fraction (BV/TV) in the fourth lumbar vertebrae (L4) was increased in mice supplemented with hCol1 (FIG. 20D). Lastly, DXA analysis of whole body bone mineral density revealed positive effects in mice supplemented with hCol1 or hCol2 (FIG. 20E). Overall, these data support improvement of bone quality by hCol1 and hCol2.

EXPERIMENTAL

Animals

All handling of mice and in vivo experimental procedures performed in studies reported here were reviewed and approved by the Institutional Animal Care and Use Committee (IACUC) at the University of Rochester (protocol number UCAR-2005-226R). Male C57BL/6J mice were purchased from Jackson Laboratories and were housed individually in micro-isolator cages on a 12 hour light/dark cycle. Male mice were used in this study due to a faster and more temporally predictable progression of degeneration. Mice had ad libitum access to standard chow and fresh water, and were supplemented with hCol1 of bovine origin and a mean molecular weight of 2500 Da (Rousselot) or of hCol2 of porcine origin of mean molecular weight 2700 Da using a method previously described to deliver daily doses of estradiol. (Ingberg et al. 2012 *General and comparative endocrinology* 175(1):188-93.)

Briefly, hCol1 and hCol2 were incorporated into Nutella such that 150 mg of the mixture would deliver either low dose (LD, 3.8 mg) or high dose (HD, 38 mg) hCol1 or a low dose (3.8 mg) hCol2 when completely consumed. The HD is the body weight adjusted mouse equivalent to the 7.4 g/day recommended human dose for hCol1. At the beginning of the experimental time line (FIG. 1C), 12 week old mice were presented with an autoclavable ceramic tile loaded with a 150 mg aliquot of Nutella vehicle, LD hCol1, HD hCol1, or hCol2 (FIG. 1A). These experimental supplements were provided daily at the same time (in the morning), and once trained, the mice consumed the entire provided amount within 2 minutes (FIG. 1B). Modeling the daily consumption regimen suggested for lifelong joint health in humans, mice were fed the supplements daily during the entire experimental protocol until collection of experimental endpoints.

To initiate PTOA, we either employed a method developed and routinely used by our group known as meniscal-ligamentous injury (MLI), (Mooney et al. 2011 *Arthritis research & therapy* 13(6):R198; Sampson et al. 2011 *J Orthop Res.* 29(8):1145-51; Sampson et al. 2011 *Sci Transl Med.* 3(101):101ra93; Hamada et al. 2014 *Methods Mol Biol.* 1130:61-72) or a destabilization of the medial meniscus (DMM) model of injury that is widely used in the preclinical OA field. (Glasson et al. 2007 *Osteoarthritis Cartilage* 15(9):1061-9.) Briefly, mice in the experimental protocol (at 17 weeks of age) were anesthetized via intraperitoneal injection of 60 mg/kg ketamine and 4 mg/kg xylazine. For the MLI model, after creating a 3 mm incision over the anteromedial aspect of the right knee joint, the medial collateral ligament of the right knee was transected and a segment of the anterior horn of the medial meniscus was excised. This injury leads to detectable PTOA joint changes by 4 weeks post-injury and progresses over 4 months, similar to that seen in the DMM model of posttraumatic OA. (Sampson et al. 2011 *J Orthop Res.* 29(8):1145-51; Glasson et al. 2007 *Osteoarthritis Cartilage* 15(9):1061-9.) For the DMM procedure, similar steps were carried out to access the joint, and the medial meniscotibial ligament was transected to destabilize the medial meniscus. In both cases (MLI and DMM), the contralateral limb provided a sham control, with the surgery consisting of only the incision (no joint structures were manipulated). Mice were provided buprenorphine analgesia (0.5 mg/kg) at the time of surgery and every 12 hours for 3 days.

Tissue Fixation and Histology Preparation

A previously established systematic approach to preparation, sectioning and visualizing mouse knee joint articular cartilage was employed for all tissue-based assays. ((Sampson et al. 2011 *J Orthop Res.* 29(8):1145-51)

At the time of harvest (3 or 12 weeks post-MLI), mice were sacrificed using an AMVA-approved method and the knee joints were dissected with the femur and tibia intact to maintain joint structure. Tissues were fixed in 4% paraformaldehyde at 4° C. for 72 hours, decalcified in 5% formic acid for 10 days, processed using a microwave processor, and embedded in paraffin. Tissue blocks were then serially sectioned in the midsagittal plane through the medial compartment of the joint. A series of 5 μm thick sections were cut at three distinct levels within the medial compartment, mounted on positively-charged glass slides, baked at 60° C. overnight, de-paraffinized in xylene, and rehydrated in decreasing concentrations of ethanol. To support study of tissue structure via histomorphometry and to accommodate OARSI and Synovial scoring methods, mounted sections were stained with either Toluidine Blue/Fast Green (0.04%/0.02%), Alcian Blue Hematoxylin/Orange G or Safranin O/Fast Green (1%/0.02%) using optimized protocols established by the Histology, Biochemistry and Molecular Imaging Core in the Center for Musculoskeletal Research at the University of Rochester. Unstained sections were used for the various molecular and cellular analyses described below.

Cartilage Histomorphometry

Two different approaches were used to quantify cartilage content. An automated method to quantify tissue architecture in murine allograft healing was modified and utilized to determine total cartilage area (uncalcified plus calcified) using Toluidine Blue/Fast Green-stained sections. (Zhang et al. 2016 *Bone Res.* 4:15037.)

After scanning to high resolution digital files using an Olympus VS120 Virtual Slide Microscope/Slide Scanner system, histologic images were analyzed using a software-based application that was developed to automatically distinguish between bone and cartilage based on the contrasting stain differential between these tissues (Toluidine Blue-stained cartilage and Fast Green-stained subchondral bone). Experimental image files were serially analyzed to quantify total cartilage area on the tibial plateau and femoral condyle, with the application returning information about each area separately. To compliment this, also performed was manual histomorphometry using the OsteoMetrics System as previously published. (Mooney et al. 2011 *Arthritis research & therapy* 13(6):R198; Sampson et al. 2011 *J Orthop Res.* 29(8):1145-51.)

Briefly, Safranin O/Fast Green stained sections were individually viewed using an Olympus BH2 light microscope interfaced with the OsteoMetrics System via a digital camera. OsteoMeasureXP software facilitated quantification of uncalcified cartilage, calcified cartilage and chondrocyte populations. Articular cartilage areas examined on the tibial plateau and femoral condyle were defined to be between the anterior and posterior horns of the meniscus, using a region of interest of defined size for all sections that were analyzed.

OARSI and Synovial Scoring

Regarding cartilage, semi-quantitative histopathologic grading was performed using a scoring system that has been established by the OARSI histopathology initiative as the standard method for grading of mouse cartilage degeneration. (Glasson et al. 2010 *Osteoarthritis Cartilage* 18 Suppl 3:S17-23.)

Based on this system, cartilage grading was carried out using Alcian Blue Hematoxylin/Orange G-stained joint sections using the following scale: 0=normal cartilage, 0.5=loss of proteoglycan stain without cartilage damage, 1=mild superficial fibrillation, 2=fibrillation and/or clefting extending below the superficial zone, 3=mild (<25%) loss of cartilage, 4=moderate (25-50%) loss of cartilage, 5=severe (50-75%) loss of non-calcified cartilage, and 6=eburnation with >75% loss of cartilage. Synovial scores were also obtained from each joint section, with the score reporting on the degree of synovial hyperplasia (i.e., thickness and cellularity of the synovial membrane) as previously performed. (Hamada et al. 2015 *Arthritis & rheumatology*. doi: 10.1002/art.39561.)

Briefly, a subjective scoring system of 0 to 2 was employed: 0=a synovial lining that is several (2-3) cell layers thick or <10 μm thick (normal), 1=synovial thickening with a lining cell layer between 5 and 10 cells thick or between 10 μm and 20 μm thick, and 2=severe thickening of the synovial lining >10 cells and/or >20 μm thick. OARSI and synovial scoring was performed by four blinded observers (QAD, EMS, RAM and MJZ) and observer agreement for each score was evaluated in pairs via calculation of a weighted kappa coefficient, using Fleiss-Cohen weights. (Sampson et al. 2011 *J Orthop Res.* 29(8):1145-51.)

The average pairwise coefficient was 0.90, indicative of strong agreement between the observers. The four scores (OARSI and synovium) for each section were averaged and the data from each group of mice were combined.

Molecular Analysis of Tissues

Mouse knee joint sections evaluated by immunohistochemistry were treated as follows: Endogenous peroxidases were quenched with BLOXALL (Vector) for 10 minutes followed by treatment with 3% hydrogen peroxide for 20 min, and a 1:20 dilution of normal goat serum for 30 min. Slides were incubated overnight at 4° C. with a rabbit anti-mouse TNF polyclonal (1:200; Abcam #ab6671) or a rabbit anti-human Ki-67 monoclonal antibody (1:200; Abcam #ab66155). For TNF detection, slides were then rinsed with phosphate-buffered saline containing 0.5% Tween 20, and incubated for 30 minutes at room temperature with a biotinylated goat anti-rabbit IgG (1:200; Vector). Antibody binding to TNF was detected following application of ABC reagent from Vectastain Elite ABC Kit (Vector) for 30 minutes, with a 5 minute application of ImmPACT DAB Peroxidase (HRP) Substrate (Vector) for 5 minutes.

to sacrifice for tissue harvest, mice were anesthetized via intraperitoneal injection of ketamine (60 mg/kg) and xylazine (4 mg/kg), and scans were collected and analyzed using a previously described standard method (Ackert-Bicknell et al. 2012 Bone 50(5): 1188-95).

qRTPCR Analysis of Synovial TNF Expression

At sacrifice, synovial capsules were harvested from experimental joints with the aid of surgical loops. Recovered synovial tissue was stored at −80° C. until extraction of total mRNA. mRNA was isolated from individual capsules using the Qiagen RNeasy Fibrous Tissue mini kit (Qiagen) using the manufacturer's instructions. One µg of total RNA was used to synthesize cDNA using the iScript cDNA Synthesis Kit (BioRad). The abundance of mouse β-actin, Tnf, Il1β, Mmp13 and Prg4 was then assessed by qRTPCR using SYBR Green Real Time PCR Master Mix (Qiagen). Reactions were carried out using a Rotor Gene 6000 PCR machine. Forward and reverse primer sequences for each of these gene transcripts are reported in Table 1.

TABLE 1 qRTPCR Primer Sequences

| Transcript | Forward Primer | Reverse Primer |
| --- | --- | --- |
| Tnf | 5'-CTCTTCTGTCTACTGAACTTCGGG-3' (SEQ ID NO: 1) | 5'-GAGAAGATGATCTGAGTGTGAGGG-3' (SEQ ID NO: 2) |
| Il1β | 5'-CACAGCAGCACATCAACAAG-3' (SEQ ID NO: 3) | 5'-GTGCTCATGTCCTCATCCTG-3' (SEQ ID NO: 4) |
| Mmp13 | 5'-AAGATGTGGAGTGCCTGATG-3' (SEQ ID NO: 5) | 5'-AAGGCCTTCTCCACTTCAGA-3' (SEQ ID NO: 6) |
| Prg4 | 5'-AGTGCTGTCCTGATTTCAAGAG-3' (SEQ ID NO: 7) | 5'-GGTGATTTGGGTGAGCGTTTGGTA-3' (SEQ ID NO: 8) |
| β-actin | 5'-TGTTACCAACTGGGACGACA-3' (SEQ ID NO: 9) | 5'-CTGGGTCATCTTTTCACGGT-3' (SEQ ID NO: 10) |

Nuclei were counterstained for 20 seconds with Mayer's Hematoxylin (Biocare Medical). For detection of Ki-67, after overnight incubation with primary antibody, slides were rinsed with phosphate-buffered saline and incubated for 30 minutes at room temperature with Alexa Fluor 488-conjugated goat anti-rabbit IgG (1:250; Invitrogen #ab150077). Apoptotic chondrocytes were identified using the TUNEL In Situ Cell Death Detection Kit (Roche, #11684795910) as instructed by the manufacturer. In the case of Ki-67 and TUNEL, nuclei were counterstained with DAPI and experimental fluorescence was imaged using a Zeiss Axioskop 40 BF/DF/Fluorescence Microscope with a SPOT RT3 Color/Slider Camera.

MicroCT Analysis

Prior to histologic processing, knee joints and lumbar vertebrae were evaluated via micro-CT using a Scanco vivaCT 40 scanner with 55-kVp source (Scanco). Tissue samples were scanned at a resolution of 12 µm, with a slice increment of 10 µm. Images from each group were reconstructed at identical thresholds to allow 3-dimensional structural rendering of each anatomical element and recovery of various structural parameters as previously described (Mooney et al. 2011 Arthritis research & therapy 13(6): R198).

Bone Densitometry (DEXA)

Whole body bone mineral density was determined via Dual Energy X-ray Absorptiometry (DEXA) scanning using a PIXImus2 Mouse Densitometer (General Electric). Prior Analysis of the Gut Microbiome Fecal pellets were freshly harvested from mice after scruffing and immediately frozen at −80° C. DNA was extracted using the ZR Fecal DNA Extraction Kit (Zymo Research) as directed by the manufacturer. 16S ribosomal DNA (rDNA) was amplified with Phusion High-Fidelity polymerase (Thermo Scientific, Waltham, Mass.) and dual indexed primers specific to the V3-V4 hypervariable regions (319F: 5' ACTCCTACGGGAGGCAGCAG 3' (SEQ ID NO:11); 806R: 3' ACTCCTACGGGAGGCAGCAG 5' (SEQ ID NO:12))[68]. Amplicons were pooled and paired-end sequenced on an Illumina MiSeq (Illumina, San Diego, Calif.) in the University of Rochester Genomics Research Center. Each sequencing run included: positive controls consisting of a 1:5 mixture of Staphylococcus aureus, Lactococcus lactis, Porphyromonas gingivalis, Streptococcus mutans, and Escherichia coli; and negative controls consisting of sterile saline. Raw data from the Illumina MiSeq was first converted into FASTQ format 2×300 paired end sequence files using the bcl2fastq program, version 1.8.4, provided by Illumina. Format conversion was performed without de-multiplexing and the EAMMS algorithm was disabled. All other settings were default. Sequence processing and microbial composition analysis were performed with the Quantitative Insights into Microbial Ecology (QIIME) software package (Caporaso et al. 2010 Nat Methods 7(5): 335-6.), version 1.9.1. Reads were multiplexed using a configuration described previously (Fadrosh et al. 2014

Microbiome 2(1):6.). Briefly, for both reads in a pair, the first 12 bases were a barcode, which was followed by a primer, then a heterogeneity spacer, and then the target 16S rRNA sequence. Using a custom Python script, the barcodes from each read pair were removed, concatenated together, and stored in a separate file. Read pairs were assembled using fastq-join from the ea-utils package, requiring at least 40 bases of overlap and allowing a maximum of 10% mismatched bases. Read pairs that could not be assembled were discarded. The concatenated barcode sequences were prepended to the corresponding assembled reads, and the resulting sequences were converted from FASTQ to FASTA and QUAL files for QIIME analysis. Barcodes, forward primer, spacer, and reverse primer sequences were removed during de-multiplexing. Reads containing more than four mismatches to the known primer sequences or more than three mismatches to all barcode sequences were excluded from subsequent processing and analysis. Assembled reads were truncated at the beginning of the first 30 base window with a mean Phred quality score of less than 20 or at the first ambiguous base, whichever came first. Resulting sequences shorter than 300 bases or containing a homopolymer longer than six bases were discarded. Operational taxonomic units (OTU) were picked using the reference-based USEARCH (version 5.2) (Edgar et al. 2011 Bioinformatics 27(16):2194-200.) pipeline in QIIME, using the May 2013 release of the GreenGenes 99% OTU database as a closed reference (DeSantis et al. 2006 Applied and environmental microbiology 72(7):5069-72; McDonald et al. 2012 ISME J. 6(3):610-8. An indexed word length of 128 and otherwise default parameters were used with USEARCH. Chimera detection was performed de novo with UCHIME, using default parameters (Edgar et al. 2011 Bioinformatics 27(16):2194-200.). OTU clusters with less than four sequences were removed, and representative sequences used to make taxonomic assignments for each cluster were selected on the basis of abundance. The RDP Naïve Bayesian Classifier was used for taxonomic classification with the GreenGenes reference database, using a minimum confidence threshold of 0.85 and otherwise default parameters (Wang et al. 2007 Applied and environmental microbiology 73(16):5261-7.).

Statistical Analyses

For all histomorphometry-based analysis of cartilage architecture, including cartilage area and chondrocyte population studies, one-way ANOVA with a Tukey's multiple comparisons post-test was performed. After confirming blinded observer agreement via calculation of weighted kappa coefficients, OARSI and synovial scoring studies were analyzed using a Kruskal-Wallis Test with a Dunn's multiple comparisons post-test. These analyses and all graphing of the data were carried out using Graphpad Prism software. Differences between groups were considered significant when a p-value <0.05 was achieved.

STATEMENTS

Preferred statements (features) and embodiments of the compositions, combinations, dosage forms, and kits, and methods and uses thereof described herein are set herein below. Each statement and embodiment so defined may be combined with any other statement and/or embodiment, unless clearly indicated to the contrary. In particular, any feature indicated as being preferred or advantageous may be combined with any other features or statements indicated as being preferred or advantageous.

1. A composition for use in treating a disease or disorder or providing a health benefit, wherein the composition comprises hydrolyzed collagen peptides.

2. The composition for use according to statement 1, wherein the use is for treating a disease or disorder in skin, joint or bone or providing a health benefit to skin, joint or bone.

3. The composition for use according to statement 1 or 2, wherein the use is for treating inflammation, preferably wherein the disease is osteoarthritis, or a related disease or disorder.

4. The composition for use according to statement 3, wherein the inflammation is related to synovial hyperplasia.

5. The composition for use according to any of statements 1-4, wherein the hydrolyzed collagen peptides comprise type 1 hydrolyzed collagen peptides (hCol1) and/or wherein the hydrolyzed collagen peptides comprise type 2 hydrolyzed collagen peptides (hCol2).

6. The composition for use according to any one of statements 1-5, wherein the hCol1 has a mean molecular weight between about 300 Da and about 7500 Da and/or wherein the hCol2 has a mean molecular weight between about 300 Da and about 7500 Da.

7. The composition for use according to statement 6, wherein the hCol1 and/or the hCol12 originates from bovine, porcine or fish collagen.

8. The composition for use according to any one of statements 1-7, suitable for oral administration.

9. The composition for use according to statement 8, suitable for daily, thrice weekly, twice weekly, or weekly administration.

10. A combination for use in treating a disease or disorder or providing a health benefit, wherein the combination comprises the composition of any of statements 1-9 and microbes from the phylum Tenericutes and/or the order Anaeroplasmatales and/or the genus *Bifidobacteria* in the same composition as the hydrolyzed collagen, or wherein the microbes are present in a separate composition.

11. The combination for use according to statement 10, wherein the amount of microbes from the phylum Tenericutes and/or the order Anaeroplasmatales and/or the genus *Bifidobacteria* are present in an amount effective for treating osteoarthritis or a related disease or disorder.

12. The combination for use according to statement 10, wherein the amount of microbes from the phylum Tenericutes and/or the order Anaeroplasmatales and/or the genus *Bifidobacteria* are present in an amount effective for treating inflammation related to synovial hyperplasia.

13. A composition comprising hydrolyzed collagen peptides and microbes from the phylum Tenericutes and/or the order Anaeroplasmatales and/or the genus *Bifidobacteria*.

14. The composition according to statement 13, wherein the hydrolyzed collagen peptides are hCol1 and/or hCol2.

15. A unit dosage form comprising a composition according to any of statements 1-9, 13 and 14, wherein the unit dosage form is a tablet, capsule, powder or liquid.

16. A unit dosage form comprising a combination according to any of statements 10-12, wherein the unit dosage form is a tablet, capsule, powder or liquid.

17. The unit dosage form according to statement 15 or 16, comprises from about 0.8 grams to about 15 grams of hydrolyzed collagen peptides and/or from about $10^7$ CFU to about $10^{12}$ CFU of microbes from the phylum Tenericutes and/or the order Anaeroplasmatales and/or the genus *Bifidobacteria*.

18. The unit dosage form according to any of statements 15-17, wherein the hCol1 has a mean molecular weight between about 300 Da and about 7500 Da and/or wherein the hCol2 has a mean molecular weight between about 300 Da and about 7500 Da.

19. The unit dosage form according to statement 18, wherein the hCol1 and/or the hCol12 originates from bovine, porcine or fish collagen.

20. A package or kit comprising a composition comprising hydrolyzed collagen peptides and a composition comprising microbes from the phylum Tenericutes and/or the order Anaeroplasmatales and/or the genus *Bifidobacteria,* or a composition comprising both hydrolyzed collagen peptides and microbes from the phylum Tenericutes and/or the order Anaeroplasmatales and/or the genus *Bifidobacteria.*

21. The package or kit according to statement 20, wherein the hydrolyzed collagen peptides are hCol1 and/or hCol2.

22. The package or kit according to statement 21, wherein the hCol1 has a mean molecular weight between about 300 Da and about 7500 Da and/or wherein the hCol2 has a mean molecular weight between about 300 Da and about 7500 Da.

23. The package or kit according to statement 21 or 22, wherein the hCol1 and/or the hCol12 originates form porcine, bovine or fish collagen.

24. Use of a composition comprising hydrolyzed collagen peptides for improving the gut microbiome.

25. The use according to statement 24, wherein the hydrolyzed collagen peptides are hCol1 and/or hCol2.

26. The use according to statement 25, wherein hCol1 has a mean molecular weight between about 300 Da and about 7500 Da and/or wherein the hCol2 has a mean molecular weight between about 300 Da and about 7500 Da.

27. The use according to statement 25 or 26, wherein the hCol1 and/or the hCol2 originates form porcine, bovine or fish collagen.

28. Use of a composition comprising hydrolyzed collagen peptides as a prebiotic.

29. The use according to statement 28, wherein the hydrolyzed collagen peptides are hCol1 and/or hCol2.

30. The use according to statement 29, wherein hCol1 has a mean molecular weight between about 300 Da and about 7500 Da and/or wherein the hCol2 has a mean molecular weight between about 300 Da and about 7500 Da.

31. The use according to statement 29 or 30, wherein the hCol1 and/or the hCol12 originates form porcine, bovine or fish collagen.

32. A method for treating osteoarthritis, or a related disease or disorder, comprising: administering to a subject in need thereof a composition comprising hydrolyzed collagen peptides in an amount effective to treat osteoarthritis, or a related disease or disorder thereof.

33. The method according to statement 32, wherein the hydrolyzed collagen peptides comprise hCol1 and/or hCol2.

34. The method according to statement 33 or 34, further comprising administering to a subject in need thereof a composition comprising microbes from the phylum Tenericutes and/or the order Anaeroplasmatales and/or the genus *Bifidobacteria* in an amount effective to treat osteoarthritis, or a related disease or disorder thereof.

35. The method according to any of statements 32-34, wherein the hydrolyzed collagen peptides are administered daily, thrice weekly, twice weekly, or weekly.

36. The method according to statement 34 or 35, wherein the microbes from the phylum Tenericutes and/or the order Anaeroplasmatales and/or the genus *Bifidobacteria* are administered daily, thrice weekly, twice weekly, or weekly.

37. The method according to any of statements 32-36, wherein administration is performed via oral administration.

38. The method according to any of statements 32-37, wherein the hydrolyzed collagen peptides are characterized by a mean molecular weight of about 300 Da to about 7500 Da.

39. The method according to any of statements 32-38, wherein the hydrolyzed collagen peptides are characterized by a mean molecular weight of about 1000 Da to about 5000 Da.

40. The method according to any of statements 32-39, wherein the hydrolyzed collagen peptides are characterized by a mean molecular weight of about 2000 Da to about 3000 Da.

41. A method for treating a disease or disorder in the skin, joint or bone, comprising: administering to a subject in need thereof a composition comprising hydrolyzed collagen peptides in an amount effective to treat the disease or disorder in the skin, joint or bone, or a related disease or disorder thereof.

42. The method according to statement 41, wherein the hydrolyzed collagen peptides comprise hCol1 and/or hCol2.

43. The method according to statement 41 or 42, further comprising administering to a subject in need thereof a composition comprising microbes from the phylum Tenericutes and/or the order Anaeroplasmatales and/or the genus *Bifidobacteria* in an amount effective to treat osteoarthritis, or a related disease or disorder thereof.

44. The method according to any of statements 41-43, wherein the hydrolyzed collagen peptides are administered daily, thrice weekly, twice weekly, or weekly.

45. The method according to statement 43 or 44, wherein the microbes from the phylum Tenericutes and/or the order Anaeroplasmatales and/or the genus *Bifidobacteria* are administered daily, thrice weekly, twice weekly, or weekly.

46. The method according to any of statements 41-45, wherein administration is performed via oral administration.

47. The method according to any of statements 41-46, wherein the hydrolyzed collagen peptides are characterized by a mean molecular weight of about 300 Da to about 7500 Da.

48. The method according to any of statements 41-47, wherein the hydrolyzed collagen peptides are characterized by a mean molecular weight of about 1000 Da to about 5000 Da.

49. The method according to any of statements 41-48, wherein the hydrolyzed collagen peptides are characterized by a mean molecular weight of about 2000 Da to about 3000 Da.

50. A method for improving joint health, skin health, joint health or bone health, comprising:
administering to a subject in need thereof hydrolyzed collagen peptides and microbes from the phylum Tenericutes and/or the order Anaeroplasmatales and/or the genus *Bifidobacteria,* in a single composition or in separate compositions, in amounts effective improving joint health, skin health, joint health or bone health.

51. The method according to statement 50, wherein the hydrolyzed collagen peptides comprise hCol1 and/or hCol2.

52. The method according to statement 50 or 51, wherein administration is daily, thrice weekly, twice weekly, or weekly.

53. The method according to any of statements 50-52, wherein administration is performed via oral administration.

54. The method according to any of statements 50-53, wherein the hydrolyzed collagen peptides are characterized by a mean molecular weight of about 300 Da to about 7500 Da.

55. The method according to any of statements 50-54, wherein the hydrolyzed collagen peptides are characterized by a mean molecular weight of about 1000 Da to about 5000 Da.

56. The method according to any of statements 50-55, wherein the hydrolyzed collagen peptides are characterized by a mean molecular weight of about 2000 Da to about 3000 Da.

57. A method for providing a prebiotic material to a subject, comprising administering to a subject in need thereof a composition comprising an effective amount of hydrolyzed collagen peptides.

58. The method according to statement 57, wherein the hydrolyzed collagen peptides comprise hCol1 and/or hCol2.

59. The method according to statement 57 or 58, further comprising administering to a subject in need thereof a composition comprising microbes from the phylum Tenericutes and/or the order Anaeroplasmatales and/or the genus *Bifidobacteria* in an amount effective to treat osteoarthritis, or a related disease or disorder thereof.

60. The method according to any of statements 57-59, wherein the hydrolyzed collagen peptides are administered daily, thrice weekly, twice weekly, or weekly.

61. The method according to statement 59 or 60, wherein the microbes from the phylum Tenericutes and/or the order Anaeroplasmatales and/or the genus *Bifidobacteria* are administered daily, thrice weekly, twice weekly, or weekly.

62. The method according to any of statements 57-61, wherein administration is performed via oral administration.

63. The method according to any of statements 57-62, wherein the hydrolyzed collagen peptides are characterized by a mean molecular weight of about 300 Da to about 7500 Da.

64. The method according to any of statements 57-63, wherein the hydrolyzed collagen peptides are characterized by a mean molecular weight of about 1000 Da to about 5000 Da.

65. The method according to any of statements 57-64, wherein the hydrolyzed collagen peptides are characterized by a mean molecular weight of about 2000 Da to about 3000 Da.

66. A method for providing a chondroprotective effect, comprising: administering to a subject in need thereof a composition comprising an effective amount of hydrolyzed collagen peptides.

67. The method according to statement 66, wherein the hydrolyzed collagen peptides comprise hCol1 and/or hCol2.

68. The method according to statement 66 or 67, further comprising administering to a subject in need thereof a composition comprising microbes from the phylum Tenericutes and/or the order Anaeroplasmatales and/or the genus *Bifidobacteria* in an amount effective to treat osteoarthritis, or a related disease or disorder thereof.

69. The method according to any of statements 66-68, wherein the hydrolyzed collagen peptides are administered daily, thrice weekly, twice weekly, or weekly.

70. The method according to statement 68 or 69, wherein the microbes from the phylum Tenericutes and/or the order Anaeroplasmatales and/or the genus *Bifidobacteria* are administered daily, thrice weekly, twice weekly, or weekly.

71. The method according to any of statements 66-70, wherein administration is performed via oral administration.

72. The method according to any of statements 66-71, wherein the hydrolyzed collagen peptides are characterized by a mean molecular weight of about 300 Da to about 7500 Da.

73. The method according to any of statements 66-72, wherein the hydrolyzed collagen peptides are characterized by a mean molecular weight of about 1000 Da to about 5000 Da.

74. The method according to any of statements 66-73, wherein the hydrolyzed collagen peptides are characterized by a mean molecular weight of about 2000 Da to about 3000 Da.

75. A method for improving gut microbiome and/or for treating a disease or condition related thereto, comprising:
administering to a subject in need thereof a composition comprising hydrolyzed collagen peptides in an amount effective to improve gut microbiome and/or to treat a disease or disorder related thereto.

76. The method according to statement 75, wherein the hydrolyzed collagen peptides comprise hCol1 and/or hCol2.

77. The method according to statement 75 or 76, further comprising administering to a subject in need thereof a composition comprising microbes from the phylum Tenericutes and/or the order Anaeroplasmatales and/or the genus *Bifidobacteria* in an amount effective to treat osteoarthritis, or a related disease or disorder thereof.

78. The method according to any of statements 75-77, wherein the hydrolyzed collagen peptides are administered daily, thrice weekly, twice weekly, or weekly.

79. The method according to statement 77 or 78, wherein the microbes from the phylum Tenericutes and/or the order Anaeroplasmatales and/or the genus *Bifidobacteria* are administered daily, thrice weekly, twice weekly, or weekly.

80. The method according to any of statements 77-79, wherein administration is performed via oral administration.

81. The method according to any of statements 77-80, wherein the hydrolyzed collagen peptides are characterized by a mean molecular weight of about 300 Da to about 7500 Da.

82. The method according to any of statements 77-81, wherein the hydrolyzed collagen peptides are characterized by a mean molecular weight of about 1000 Da to about 5000 Da.

83. The method according to any of statements 77-82, wherein the hydrolyzed collagen peptides are characterized by a mean molecular weight of about 2000 Da to about 3000 Da.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples disclosed herein are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance that can be adapted to the practice of this invention in its various embodiments and equivalents thereof.

---

The invention claimed is:

1. A method of administering a prebiotic to a subject comprising administering to the subject a prebiotic composition comprising hydrolyzed collagen peptides, wherein the hydrolyzed collagen peptides are type 1 hydrolyzed collagen peptides (hCol1) originating from bovine, or type 2 hydrolyzed collagen peptides (hCol2) originating from porcine, wherein the hCol1 have a mean molecular weight between about 1800 Da and about 3500 Da and the hCol2 have a mean molecular weight between about 1300 Da and about 3000 Da.

2. The method of claim 1, wherein the gut microbiome in the subject is modulated.

3. The method according to claim 1, wherein microbial diversity in the gut is increased.

4. The method according to claim 1, wherein the composition comprises at least 90% or at least 95% by weight hydrolyzed collagen peptides, based on the dry mass of the composition.

5. The method according to claim 1, wherein said composition is formulated in a food or feed product, or a food or feed ingredient for oral administration.

6. The method according to claim 1, wherein said composition is formulated as a dietary supplement for oral administration.

7. The method according to claim 1, wherein said composition is administered to a subject each day for at least 7 days or for at least 14 days.

8. The method according to claim 1, wherein said composition is administered to the subject at a daily dosage of between 0.5 g and 15 g.

9. A method of preventing or treating joint inflammation in a subject comprising administering to the subject a composition comprising hydrolyzed collagen peptides, wherein the hydrolyzed collagen peptides are type 1 hydrolyzed collagen peptides (hCol1) originating from bovine, or type 2 hydrolyzed collagen peptides (hCol2) originating from porcine, wherein the hCol1 have a mean molecular weight between about 1800 Da and about 3500 Da and the hCol2 have a mean molecular weight between about 1300 Da and about 3000 Da.

10. The method according to claim 9, wherein the joint inflammation is synovial inflammation.

11. The method according to claim 9, wherein the composition comprises at least 90% or at least 95% by weight hydrolyzed collagen peptides, based on the dry mass of the composition.

12. A method for preventing or treating osteoarthritis in a subject, comprising administering to the subject a composition comprising hydrolyzed collagen peptides, wherein the hydrolyzed collagen peptides are type 2 hydrolyzed collagen peptides (hCol2) that originate from porcine collagen from cartilage, wherein the hCol2 have a mean molecular weight between about 1300 Da and about 3000 Da.

13. The method according to claim 12, wherein said osteoarthritis is posttraumatic osteoarthritis or obesity-induced osteoarthritis.

14. The method according to claim 12, wherein said composition comprises at least 90% or at least 95% by weight hydrolyzed collagen peptides, based on the dry mass of the composition.

15. A method of administering a chondroprotective agent to a subject comprising administering to the subject a composition comprising hydrolyzed collagen peptides, wherein the hydrolyzed collagen peptides are type 2 hydrolyzed collagen peptides (hCol2) originating from porcine, wherein the hCol2 have a mean molecular weight between about 1300 Da and about 3000 Da.

16. The method according to claim 15, wherein the composition comprises at least 90% or at least 95% by weight hCol2, based on the dry mass of the composition.

17. The method according to claim 15, wherein the hCol12 originates from porcine collagen from cartilage.

* * * * *